(12) United States Patent
Tidmarsh

(10) Patent No.: US 7,560,230 B2
(45) Date of Patent: Jul. 14, 2009

(54) METHOD FOR DETERMINING SUSCEPTIBILITY OF TUMOR TO TREATMENT WITH ANTI-NEOPLASTIC AGENT

(75) Inventor: George Tidmarsh, Portola Valley, CA (US)

(73) Assignee: Threshold Pharmaceuticals, Inc., Redwood City, CA (US)

( * ) Notice: Subject to any disclaimer, the term of this patent is extended or adjusted under 35 U.S.C. 154(b) by 227 days.

(21) Appl. No.: 10/546,612

(22) PCT Filed: Mar. 4, 2004

(86) PCT No.: PCT/US2004/006897

§ 371 (c)(1),
(2), (4) Date: Aug. 18, 2005

(87) PCT Pub. No.: WO2004/081181

PCT Pub. Date: Sep. 23, 2004

(65) Prior Publication Data

US 2006/0172305 A1    Aug. 3, 2006

Related U.S. Application Data

(60) Provisional application No. 60/453,083, filed on Mar. 7, 2003.

(51) Int. Cl.
*C12Q 1/68* (2006.01)
*G01N 33/53* (2006.01)

(52) U.S. Cl. ............................ 435/6; 435/7.1; 435/91.2; 530/350; 530/387.1; 536/23.5; 536/24.3

(58) Field of Classification Search ...................... 435/6, 435/7.1, 91.2; 530/387.1, 350; 536/24.3, 536/23.5

See application file for complete search history.

(56) References Cited

U.S. PATENT DOCUMENTS

| 3,694,428 | A | 9/1972 | Hardegger et al. |
| 3,940,383 | A | 2/1976 | Fujiwara et al. |
| 5,622,936 | A | 4/1997 | Wiessler et al. |
| 6,489,302 | B1 | 12/2002 | Wiessler et al. |
| 7,001,888 | B2 | 2/2006 | Tidmarsh et al. |

FOREIGN PATENT DOCUMENTS

| WO | WO 99/18125 A1 | 4/1999 |
| WO | WO 99/20316 A1 | 4/1999 |
| WO | WO 9918125 A1 * | 4/1999 |
| WO | WO 00/52476 A1 | 9/2000 |
| WO | WO 02/058741 A2 | 8/2002 |
| WO | WO 03/082301 A1 | 10/2003 |

OTHER PUBLICATIONS

Wu et al. (Genomics. Dec. 2002; 80 (6): 553-557).*
Nielsen et al. (Diabetes. 1999; 48: 2324-2332).*
Elsner et al. (Diabetologica. 2002; 45: 1542-1549).*
Kunkel et al. (Oral Oncol. 2007; 43: 796-803).*
Maher et al. (Pancreas. Mar. 2005; 30 (2): e34-e39).*
Airley et al. (Clin. Cancer Res. 2001; 7: 928-934).*
Medina et al. (Endocrinol. 2003; 144: 4527-4535).*
Seino et al. (J. Clin. Endocrinol. Metab. 1993; 76: 75-78).*
Veyhl et al. (Proc. Natl. Acad. Sci. USA. 1998; 95: 2914-2919).*
Kato et al. (Anticancer Res. Jul.-Aug. 2003; 23 (4): 3263-3272).*
Higashi et al. (Eur. J. Nucl. Med. Dec. 2000; 27 (12): 1778-1785).*
Yen et al. (J. Nucl. Med. Jan 2004; 45 (1): 22-29).*
Higashi et al. (J. Nucl. Med. Oct. 1998; 39 (10): 1727-1735).*
Reske et al. (J. Nucl. Med. Sep. 1997; 38 (9): 1344-1348).*
Bell et al., "Molecular Biology of Mammalian Glucose Transporters", *Diabetes Care*, 13:198-208, (1990).
Burant et al., "Fructose Transporter in Human Spermatozoa and Small Intestine Is GLUT5", *J. Biol. Chem.*, 267:14523-6, (1992).
Cantuaria et al., "Antitumor Activity of a Novel Glyco-Nitric Oxide Conjugate in Ovarian Carcinoma", *Cancer Res.*, 88:381-88, (2000).
Elsner et al., "Relative importance of transport and alkylation for pancreatic beta-cell toxicity of streptozotocin", *Diabetologia*, 43:1528-33, (2000).
Hosokawa et al., "Differential Sensitivity of GLUT1- and GLUT2-Expressing β Cells to Streptozotocin",*Biochem. Biophys. Res. Commun.*, 289:1114-17, (2001).
Joost et al., "The extended GLUT-family of sugar/polyol transport facilitators: nomenclature, sequence characteristics, and potential function of its novel members", *Mol. Membr. Biol.*, 18:247-56, (2001).
Medina et al., "Glucose transporters: expression, regulation and cancer", *Biol. Res.*, 35:9-26, (2002).
Niculescu-Duv Az, "Glufosfamide", *Curr. Opin. Investig. Drugs*, 3:1527-32, (2002).
Panayotova-Heiermann et al., "Sugar Binding to Na+/ Glucose Cotransporters Is Determined by the Carboxyl-terminal Half of the Protein", *J. Biol. Chem.*, 271:10029-34, (1996).
Ramirez et al., "Glyco-S-Nitrosothiols, A Novel Class of No Donor Compounds", *Bioorg. Med. Chem. Lett.*, 6:2575-80, (1996).
Schnedl et al., "STZ Transport and Cytotoxicity", *Diabetes*, 43:1326-33, (1994).
Smith, "Facilitative glucose transporter expression in human cancer tissue", *Br. J. Biomed. Sci.*, 56:285-92, (1999).
Veyhl et al., "Transport of the new chemotherapeutic agent β-D-glucosylisophosphoramide mustard (D-19575) into tumor cells is mediated by the Na+-D-glucose cotransporter SAAT1", *Proc. Natl. Acad. Sci.*, 95:2914-9, (1998).
Wang et al., "GLUT2 in Pancreatic Islets", *Diabetes*, 47:50-56, (1998).
Wang et al., "Glucose Transporter 2 Expression: Prevention of Streptozotocin-Induced Reduction in Beta-Cells With 5-Thio-D-Glucose", *Exp. Clin. Endocrinol. Diabetes*, 103:83-97 Supp 2., (1995).
Wang et. al., "Expression of GLUT1 protein and its relationship with uptake of FDG in non-small cell lung tissues", *Clin. J. Lung. Cancer*, 5(3):174-76, (2002) (Chinese langueage article with English Abstract).

* cited by examiner

*Primary Examiner*—Stephen L Rawlings
(74) *Attorney, Agent, or Firm*—Townsend and Townsend and Crew LLP

(57) ABSTRACT

The level of one or more glucose transporters in a sample containing cancer cells is measured and compared to a reference value to determine whether the cancer is susceptible to treatment with an anti-cancer agent comprising glucose or glucose analog that is transported into the cancer by a glucose transporter.

17 Claims, No Drawings

METHOD FOR DETERMINING SUSCEPTIBILITY OF TUMOR TO TREATMENT WITH ANTI-NEOPLASTIC AGENT

CROSS-REFERENCE TO RELATED PATENT APPLICATIONS

This application claims benefit of U.S. provisional application No. 60/453,083, filed on Mar. 7, 2003, the entire contents of which are incorporated herein by reference.

REFERENCE TO A SEQUENCE LISTING

This application includes a sequence listing in a text file entitled SEQLIS021305003800US.txt, created on Oct. 6, 2008, and containing 96794 bytes, a paper copy of which is appended hereto.

1. Field of Invention

The invention relates to methods of determining the susceptibility of a tumor to treatment with anti-neoplastic agents, and finds application in biology and medicine.

2. Background of the Invention

The term "cancer" generally refers to one of a group of more than 100 diseases caused by the uncontrolled growth and spread of abnormal cells that can take the form of solid tumors, lymphomas, and non-solid cancers such as leukemia. Physicians treating patients with cancer have a diverse arsenal of drug and non-drug therapies available. Identification of the appropriate therapy for a particular patient can be problematic, however, because although certain therapies can be matched to certain cancer types, patients' responses to a given therapy are not uniform.

A number of promising anti-cancer agents contain a glucose or glucose-like moiety and so may be a substrate for glucose transporters, membrane proteins that facilitate cell uptake of glucose. Examples include the anti-cancer drugs streptozotocin (STZ), glucofosfamide, and 2gluSNAP, and additional glucose or glucose-analog-containing drugs are being developed. The glucose-like moieties of these drugs mediate transport into cancer cells and thereby take advantage of the fact that many cancer cells exhibit, relative to normal cells, enhanced glucose metabolism thought to be due, in part, to an increase in the numbers of glucose transporters (see Medina et al., 2002, *Biol Res*. 35:9-26). However, not all patients (or cancers) respond to treatment with drugs such as streptozotocin, glucofosfamide, and 2gluSNAP. Methods to help predict which patients are most likely to benefit from specific treatment with specific anti-cancer agents and classes of agents would allow the physician to treat cancer more effectively and provide considerable benefit to patients. The present invention provides such methods.

SUMMARY OF THE INVENTION

The present invention has multiple aspects but generally provides methods and reagents for screening cancer patients to determine whether the cancer from which they suffer is susceptible to treatment with a glucose or glucose analog-containing anti-cancer agent.

In one aspect, the present invention provides a means to correlate the level of one or more glucose transporters in cancer cells with the susceptibility of said cells to an anti-cancer agent that is transported by said transporters, such as an anti-neoplastic agent containing glucose or a glucose analog. In one embodiment, the agent comprises a glucose moiety; in other embodiments, the agent contains a 2-deoxyglucose or a fructose moiety.

In one embodiment, the invention provides a method for determining whether a cancer is susceptible to treatment with an anti-neoplastic agent by (a) obtaining a sample of the cancer; (b) measuring the level of at least one glucose transporter in the sample; (c) comparing the level with a predetermined value, and (d) determining that, if the measured level is larger than the predetermined value, the cancer is susceptible to treatment with the anti-neoplastic agent. In a related aspect, the present invention provides a method for determining whether a human cancer is susceptible to treatment with an anti-cancer agent that contains glucose or a glucose analog and is transported by a glucose transporter, said method comprising: obtaining a sample of said cancer; measuring an amount of glucose transporter in said sample; comparing said amount in said sample to a predetermined value; and determining that, if said amount is larger than the predetermined value, then said cancer is susceptible to said anti-cancer agent and can be treated therewith, or, if said amount is smaller than said predetermined value, then said cancer is not susceptible or has a reduced susceptibility to said anti-cancer agent.

In one embodiment, the level in the cancer sample of more than one glucose transporter is measured. In an embodiment, the level of class I and/or a class II and/or a class III GLUT glucose transporter is measured. A variety of methods may be used to measure the level of glucose transporter in the sample. One method is an immunological assay. Another suitable method involves amplification of an RNA or cDNA. In one embodiment, said human cancer sample, which can be, for example, a sample of fresh, frozen, fixed, or fixed and paraffin-embedded tumor cells, is treated to isolate total protein from said sample, and the isolate is contacted with antibodies specific for one or more of said glucose transporters, the levels of which in said isolate are determined by detecting the complex formed between the antibody and said glucose transporter. In other embodiments, the level or amount of glucose transporter in the sample is determined by detecting glucose transporter protein with a reagent other than an antibody, for example by measuring glucose uptake in a fresh tissue sample, or by detecting messenger RNA from one or more of the glucose transporter genes, or by otherwise measuring the activity of a glucose transporter or its corresponding gene.

In one embodiment of this method, the GLUT2 level in a cancer sample is measured. In another embodiment of this method, the anti-cancer agent is streptozotocin treatment. In another embodiment, the cancer is a pancreatic cancer or islet cell carcinoma. In a preferred embodiment, the GLUT2 level is measured, the anti-cancer agent is streptozotocin, glucofosfamide, or a gluSNAP compound, and the cancer is a pancreatic cancer or islet cell carcinoma.

In another aspect, the present invention provides kits useful in the practice of the invention. In one embodiment, the kits comprise diagnostic screening reagents and instructions for the use thereof in the present method. In another embodiment, the kits further comprise an anti-neoplastic therapeutic agent that comprises glucose or glucose analog.

These and other aspects and embodiments of the invention are described in more detail in the detailed description, example, and claims that follow.

DETAILED DESCRIPTION OF THE INVENTION

1. Introduction

The present invention provides methods, reagents and devices useful in assessing whether a cancer is susceptible to treatment with an anti-cancer agent or the degree of susceptibility of a cancer to an anti-cancer agent. In one aspect the anti-cancer agent is a drug that is transported by a glucose transporter, such as a drug comprising a glucose or glucose analog moiety that is a substrate for the glucose transporter. As used herein, a determination that a cancer is "susceptible" to treatment with a drug means that there is a greater likelihood that the drug will be therapeutically efficacious against the tumor compared to the likelihood of efficacy for a tumor determined to be not "susceptible" to the agent. Determining that a cancer is susceptible to treatment with a drug or drug class therefore provides a method for determining a chemotherapeutic regimen for treatment of the patient.

In some methods of the invention, a cancer sample is obtained from a patient and tested to determine the level(s) of one or more glucose transporters; cancers expressing high levels of glucose transporters are determined to be susceptible to chemotherapy with anti-cancer agents that contain a glucose or glucose moiety and that are transported by a glucose transporter. Conversely, cancers expressing low levels of glucose transporters are determined not to be susceptible (or to be less susceptible) to such chemotherapy. The pre-therapy screening in accordance with the methods of the present invention allows the physician to treat cancer more effectively, as the physician is provided with a means for determining whether treatment with an anti-cancer agent will be effective, and if not, then to treat the cancer with a compound that may be more effective, and if so, then treating with that agent.

The term "glucose transporter" is used in the medical literature in two related, but slightly different, senses. In the first sense, glucose transporters are proteins that transport compounds (whether glucose, glucose analogs, other sugars such as fructose or inositol, or non-sugars such as ascorbic acids) across a cell membrane and are members of the glucose transporter "family" based on structural similarity (e.g., homology to other glucose transport proteins). However, some "glucose transporters" are believed to have a primary substrate other than glucose. For example, the glucose transporter GLUT5 is primarily a transporter of fructose, and is reported to transport glucose itself with low affinity. Similarly, the primary substrate for the glucose transporter HMIT is myo-inositol (a sugar alcohol). As used herein, the term "glucose transporter," unless otherwise specified, includes transporters of fructose and inositol. In one aspect, the invention contemplates measuring the level of any glucose transporter to assess the susceptibility of a tumor to an anti-cancer agent transported into a tumor cell by a glucose transporter (including, but not limited to, a glucose transporter selected from the groups of GLUT1-12, HMIT and SGLT1-6 transporters). In a preferred embodiment, the invention contemplates measuring the level of a glucose transporter that transports glucose with a higher affinity than fructose, inositol, H+-myoinositol or non-sugars such as ascorbic acids to assess the susceptibility of a tumor to an anti-cancer agent comprising a glucose or glucose analog moiety transported into a tumor cell by a glucose transporter.

In a preferred embodiment of the invention, levels in the cancer sample of one or more glucose transporters are determined and compared to a reference value(s). A high transporter level in the cancer sample, relative to the reference value, indicates the tumor is susceptible to treatment with members of the class of anti-neoplastic agents that contain a glucose or glucose analog moiety.

Accordingly, in one embodiment, the present invention encompasses a method for determining whether a cancer is susceptible to treatment with an anti-neoplastic agent comprising glucose or a glucose analog that is transported into a cancer cell by a glucose transporter, said method comprising the steps of: (a) obtaining a sample of said cancer; (b) measuring an amount of or the activity of a glucose transporter in said sample; (c) comparing said amount or activity measured in step (b) with a predetermined amount or activity; and (d) determining that, if said measured amount or activity is larger than said predetermined amount or activity, then said cancer is susceptible to said treatment, and if said measured amount is less than said predetermined amount or activity, then said cancer is not or is less susceptible to said treatment.

In one embodiment, the present invention encompasses a method for determining whether a patient is susceptible to treatment with an anti-neoplastic agent comprising glucose or a glucose analog that is transported into a cancer cell by a glucose transporter, said method comprising the steps of: (a) diagnosing the patient as having a cancer; (b) obtaining a sample of said cancer from said patient; (c) measuring an amount or activity of glucose transporter in said sample; (d) comparing said amount or activity measured in step (c) with a predetermined amount or activity; and (e) determining that, if said measured amount or activity is larger than said predetermined amount or activity, then said patient is susceptible to said treatment, and if said measured amount or activity is less than said predetermined amount or activity, then said patient is not susceptible to said treatment.

In one embodiment, the present invention encompasses a method for treating a cancer patient with an anti-neoplastic agent comprising glucose or a glucose analog that is transported into a cancer cell by a glucose transporter comprising the steps of: (a) obtaining a sample of said cancer from said patient; (b) measuring an amount or activity of glucose transporter in said sample; (c) comparing said amount or activity measured in step (b) with a predetermined amount or activity; (d) determining that, if said measured amount or activity is larger than said predetermined amount or activity, then said cancer is susceptible to said treatment, and if said measured amount or activity is less than said predetermined amount, then said cancer is not susceptible to said treatment; and if said measured amount or activity is larger than said predetermined amount or activity, (e) treating the cancer patient with the anti-neoplastic agent.

In one embodiment, the present invention encompasses a method for treating a patient with an anti-neoplastic agent comprising glucose or a glucose analog that is transported into a cancer cell by a glucose transporter comprising the steps of: (a) diagnosing the patient as having a cancer; (b) obtaining a sample of said cancer from said patient; (c) measuring an amount or activity of glucose transporter in said sample; (d) comparing said amount or activity measured in step (c) with a predetermined amount or activity; (e) determining that, if said measured amount or activity is larger than said predetermined amount or activity, then said cancer is susceptible to said treatment, and if said measured amount or activity is less than said predetermined amount or activity, then said cancer is not susceptible to said treatment; and if said measured amount or activity is larger than said predetermined amount or activity, (f) treating the patient with the anti-neoplastic agent.

2. "Anti-Cancer Agents" and "Anti-Neoplastic Agents"

Anti-cancer agents are compounds that prevent or impede the growth and/or spread of cancer cells in a patient. Administration of anti-cancer agents may result in delay or slowing of disease progression, amelioration or palliation of the disease state, remission (whether partial or total), and/or prolong survival (compared to expected survival if not receiving treatment). Anti-cancer agents presently in use or under development include, but are not limited to, alkylators, anthracyclines, antibiotics, metabolic poisons, radionucleotides, metal poisons, enzyme inhibitors, aromatase inhibitors, biphosphonates, cyclo-oxygenase inhibitors, estrogen receptor modulators, folate antagonists, inorganic arsenates, microtubule inhibitors, modifiers, nitrosoureas, nucleoside analogs, orthoclase inhibitors, platinum-containing compounds, retinoid, topoisomerase 1 inhibitors, topoisomerase 2 inhibitors, and tyrosine kinase inhibitors.

Of primary interest in the context of the present invention are anti-cancer agents transported into the cancer cell by a glucose transporter. In this context, the term "anti-neoplastic agent" is used to refer to such anti-cancer agents and thus distinguish them from anti-cancer agents not transported into the cancer cell by a glucose transporter (such as, for example, cisplatin, Bevacizumab, Pemetrexed, and the like). Anti-neoplastic agents include molecules that comprise a glucose or glucose analog moiety that facilitates or otherwise allows transport into the cell by a glucose transporter. In one embodiment, the glucose analog is itself the anti-neoplastic agent. An example of such an agent is 2-deoxyglucose (2-DG). Other examples include 2-fluoro-2-deoxyglucose (2-FDG), and radioactively labeled 2-FDG compounds such as 2-$^{18}$FDG. In another embodiment, a glucose or glucose-like moiety is conjugated to another moiety, such as a cytotoxic compound, which may be an anti-cancer agent in its own right (i.e., when not conjugated to the glucose or glucose-like moiety) such as those listed above. For example, the glucose or glucose analog moiety can serve merely as a targeting molecule that brings the cytotoxic agent attached thereon into the cell. Anti-neoplastic agents that comprise a glucose or glucose analog conjugated to a toxic moiety are described in PCT publication WO 03/082301. In one embodiment, neither the glucose-like moiety nor the other moiety is toxic when administered in a non-conjugated form. In an alternative embodiment, both the glucose-like moiety and the other moiety are toxic when administered independently.

For anti-neoplastic agents comprising a moiety conjugated to a glucose or glucose analog, any linkage that is compatible with both the glucose or glucose analog portion and the non-glucose portion may be used; for example, any of the linkages described in WO 03/082301 or in U.S. Pat. No. 5,622,936. The anti-neoplastic agent can be attached to the glucose or glucose analog at any functional site, for example, on the 1 position, 2 position, 3 position, or 4 position of glucose or glucose analogs.

Glucose analogs that are, or are a portion of, an anti-neoplastic agent for which the screening methods of the invention are useful are known in the art and include, but are not limited to, glucose derivatives such as D-(+)-2-deoxyglucose, D-(+)-2-amino-2-deoxy-glucose or N-acetyl D-(+)-2-amino-2-deoxyglucose; D-mannose and mannose derivatives; D-glucose and D-glucose derivatives, including but not limited to D-3-amino-3-deoxy-glucose and D-2-amino-2-deoxy-glucose; and D-galactose and galactose derivatives including but not limited to D-2-deoxy-D-galasctose, D-4-amino-4-deoxy-galactose and D-2-amino-2-deoxy-galactose. The glucose or glucose moiety thus can differ from D-glucose or a derivative such as 2-DG and 2-glucosamine in that it is an epimer thereof. In addition, the glucose or glucose analog moiety can be a fluorinated derivative of any of the foregoing compounds. Moreover, the oxygen in the ring of any of the foregoing compounds can be substituted with an isostere selected from the group consisting of S, sulfone, and the like. For example, the glucose analog can be 5-thio-D-glucose or a derivative thereof. The term "glucose analog" also includes glucose derivatives, including, but not limited to, derivatives having (C1-C12)acyl groups or (C1-C12)akyl groups attached via —O— or —NH— groups at the 3- and 4-positions of the glucose molecules. Additionally, the glucose derivative may have a solubility or partitioning effector or component attached at the 1-, 3-, or 4-positions.

In some embodiments, the glucose analog is fructose, psicose, sorbose, tagatose, allose, altrose, gulose, idose, talose, inositol (e.g., myo-, scillo-, muco-, and chiro inositol) or other sugar alcohol that is a substrate for a glucose transporter, or a derivative thereof that is a substrate for a glucose transporter, such as those listed in Table 1.

A number of anti-neoplastic agents that comprise a glucose or glucose analog are known, and others are being tested or developed for future clinical use. For illustration and not limitation, examples of such anti-neoplastic agents include streptozotocin, glucofosfamide, glycol-S-nitrosothiols (including 2gluSNAP), single proton-emitting radio tracers (including 2-O-(3'-iodobenzyl-D-glucose and N-(4'-iodionbenzyl)-D-glucosamine, 2-deoxy-D-glucose (2-DG) and 2-DG conjugates described in WO 03/082301, conjugates described in WO 02/058741, conjugates described in WO 99/20316, conjugates described in U.S. Pat. No. 6,489,302, and conjugates described in U.S. Pat. No. 5,622,396, and their derivatives and analogs.

Streptozotocin [2-deoxy-2-(3-methyl-3-nitroso-ureido)-D-glucose; N-methylnitrosocarbamoyl-D-glucosamine; STZ; Zanosar™] is an anti-mitotic alkylating agent in which a cytotoxic N-nitrosourea group is attached to the 2 position of glucosamine. Streptozotocin has been approved by the FDA to treat pancreatic islet cell cancer and carcinoid tumors. In contrast to other nitrosourea analogs, streptozotocin selectively targets pancreatic β-cells, due to the presence of a glucose moiety on the compound, which appears to mediate uptake into cells expressing GLUT2 (see, Schnedl et al., November 1994, *Diabetes* 43:1326-33; Elsner et al., December 2000, *Diabetologia* 43:1528-33; Hosokawa et al., December 2001, *Biochem. Biophys. Res. Commun.* 289:1114-17; Wang et al., January 1998, *Diabetes* 47:50-56; and Wang et al., 1995, *Exp. Clin. Endocrinol. Diabetes* 103 Suppl. 2:83-97). See, e.g., U.S. Pat. Nos. 3,694,428 and 3,940,383.

The anti-neoplastic agent glucofosfamide (beta-D-glucosyl-ifosfamide mustard; glc-IPM) contains a cytotoxic agent ifosfamide coupled to glucose via an ester linkage at the oxygen atom at the 1-position of glucose (see U.S. Pat. No. 5,622,936 and U.S. Pat. No. 6,489,302). Glucofosfamide has been tested for the treatment of patients with pancreatic cancer receiving first line treatment and in patients with non-small cell lung cancer receiving second line chemotherapy, as well as glioblastoma, breast cancer, and colon caner patients. See Niculescu-Duvaz, 2002, *Curr. Opin. Investig. Drug* 3:1527-32. Briasoulis et al., 2000, *J. Clin. Oncol.* 18:3535-44, reports that cellular uptake of glucofosfamide is mediated by a Na+-dependent glucose transporter.

A glycol-S-nitrosothiol compound can be described as a cytotoxic agent linked to a sugar, and has been reported as targeting tumor cells that over-express GLUT1 preferentially (see Ramirez et al., 1996, *Bioorg. Med. Chem. Lett.* 6:2575-80; and Cantuaria et al., 2000, *Cancer* 88:381-88). An exemplary glycol-S-nitrosothiol, 2gluSNAP, has a structure in which a nitric oxide donating cytotoxic moiety (S-nitroso-N-acetyl-penicillamine) is linked to 2-deoxyglucoamine at the 2 position via an amide bond. These compounds have been reported to target tumor cells that overexpress GLUT1 (see Ramirez et al., supra, and Cantuaria et al., supra).

Other anti-neoplastic agents to which the screening methods of the present invention may be applied are compounds that contain a glucose moiety linked to a single photon-emitting moiety via a heterocyclic, hydrocarbon, or aromatic groups as described in PCT publication WO 99/20316. These compounds include, for example, 2-O-(3'-iodobenzyl)-D-glucose and N-(4'-iodobenzyl)-D-glucosainine. Other examples of anti-neoplastic agents that can be attached to glucose or glucose analogs described above include, for example, Yttrium-90, Iodine-125, Iodine-131, phosphate-32, hydoxyurea, triapine, 5-HP, camptothecin and analogs thereof, carboplat and analogs thereof, DOTA and other radiomethal ion chelators, methotrexate and analogs, mitoxantrone and related anthraquinone structures, small kinase inhibitors, dacarazine or procarbazine, and mitomycin.

Compounds other than glucose and glucose analogs are transported by one or more glucose transporters. For example, ascorbic acids have also been reported to be transported into the cell by glucose transporters in the form of dehydroascorbic acids. See Vera et al., 1004, *Blood* 84:1628-34 and Agus et al., 1997, *J. Clin. Invest.* 100:2842-48. Proton/myoinositol co-transporter (HMIT), a member of the facilitative glucose transporter class, was found to be selective for myo-, scillo-, muco-, and chiro-inositol. Transport was with high affinity (Km=100 uM) and was increased by low pH with a maximal rate reached at pH=5.0.

The anti-neoplastic agents described herein are used for the treatment of cancer as primary, single-agent treatment, as well as in treatment in combination with radiation, surgery, or other anti-cancer agents, and combinations of such therapies.

3. Glucose Transporters

As noted above, in one aspect of the invention, levels of one or more glucose transporters are determined in a cancer sample. Accordingly, an appreciation of the nature and types of glucose transporters will provide the practitioner with guidance concerning the invention.

Glucose transporters include members of the facilitative glucose transporter protein family (GLUT/SLC2A), sodium-dependent glucose co-transporters (SGLT/SLC5A), the H+/myo-inositol co-transporter (HMIT1), and human or mammalian homologs and orthologs of the aforementioned. Exemplary glucose transporters, for illustration and not limitation, include those listed in Table 1.

TABLE 1

| Glucose Transporter | Nucleic Acid Sequence Accession No.* | Protein Sequence Accession No.* | Class | Selected Tissues Reported to Express Transporter | Primary References |
|---|---|---|---|---|---|
| GLUT1 | NM_006516 | P11166 (SEQ ID NO:1) | I | All tissues (abundant in erythrocytes and brain) | 1, 2 |
| GLUT2 | NM_000340 | P11168 (SEQ ID NO:2) | I | Liver, pancreas, pancreatic islet cells, retina, intestine, kidney | 2, 3 |
| GLUT3 | NM_006931 | P11169 (SEQ ID NO:3) | I | Brain | 2, 4 |
| GLUT4 | NM_001042 | P14672 (SEQ ID NO:4) | I | Heart, muscle, fat, brain | 5, 6 |
| GLUT5 | BC001692 | P22732 (SEQ ID NO:5) | II | Intestine, testes, kidney, erythrocytes | 7, 8 |
| GLUT6 | NM_017585 | Q9UGQ3 (SEQ ID NO:6) | III | Brain, spleen, leucocytes | 9, 10 |
| GLUT7 | | | II | Unknown | 11 |
| GLUT8 | NM_014580 | Q9NY64 (SEQ ID NO:7) | III | Testis, brain, blastocyst | 10, 12, 13, 14, 29 |
| GLUT9 | BC018897 | Q9NRM0 (SEQ ID NO:8) | II | Liver, kidney | 15 |
| GLUT10 | NM_030777 | O95528 (SEQ ID NO:9) | III | Liver, pancreas | 16, 17 |
| GLUT11 | NM_030807 | Q9BYW1 (SEQ ID NO:10) | II | Heart, muscle | 18, 19, 20 |
| GLUT12 | NM_145176 | NP_660159 (SEQ ID NO:11) | III | Heart, prostate, muscle, small intestine, fat | 21 |
| HMIT | NM_052885 | NP_443117 (SEQ ID NO:12) | III | Brain | 22 |
| GLUT14 | NM_153449 | AAL89709 (SEQ ID NO:13) | I | Testis | 28 |
| | AF481879 | AAL89710 (SEQ ID NO:14) | | | |
| SGLT1 | NM_000343 | P13866 (SEQ ID NO:15) | | Small intestine, kidney, heart, liver, lung | 23 |
| SGLT2 | NM_003041.1 | P31639 (SEQ ID NO:16) | | Ubiquitous (primarily kidney) | 24, 25 |
| SGLT3 | AJ133127** | Q9NY91 (SEQ ID NO:17) | | Small intestine, skeletal muscle (based on pig SGLT3) | 26 |
| SGLT5 | NM_152351 | | | | 27 |

*Reference to specific sequences is provided for illustration and is not intended to limit the invention in any fashion. For example, there may be additional or alternative sequences corresponding to the transporters listed in column 1, including, but not limited to, polymorphic sequences and other variants.
**EMBL sequence accession number.
1. Mueckler et al. 1985, Science 229:941-5;
2. Gould et al. 1991, Biochem. 30:5139-45;
3. Fukumoto et al. 1988, PNAS 85:5434-8;
4. Kayano et al. 1988, J. of Biol. Chem. 263:15245-8;
5. Fukumoto et al. 1989, J. of Biol. Chem. 264:7776-9;
6. James et al. 1989, Nature 338:83-7;
7. Kayano et al. 1990, J. of Biol. Chem. 265:13276-82;
8. Davidson et al. 1992, Am. J. of Physiol. 262:C795-C800;
9. Doege et al. 2000a, Biochem. J. 350:771-6;
10. Lisiuski et al., 2001, Biochem. J. 358:517-22;
11. Joost & Thorens, 2001, Mol. Membrane Biol. 18:247-56;
12. Carayannopoulos et al. 2000, PNAS 97:7313-8;
13. Doege et al. 2000b, J. of Biol. Chem. 275:16275-80;
14. Ibberson et al. 2000, J. of Biol. Chem. 275:4607-12;

TABLE 1-continued

| Glucose Transporter | Nucleic Acid Sequence Accession No.* | Protein Sequence Accession No.* | Class | Selected Tissues Reported to Express Transporter | Primary References |
|---|---|---|---|---|---|

15. Phay et al. 2000, Surgery 128:946-51;
16. Dawson et al. 2001, Mol. Genetics and Metabol. 74:186-99;
17. McVie-Wylie et al. 2001, Genomics 72:113-7;
18. Doege et al. 2001, Biochem.l J. 359:443-9;
19. Wu et al. 2002, Mol. Genetics and Metabol. 76:37-45;
20. Sasaki et al. 2001, Biochem. and Biophys. Res. Comm. 289:1218-24;
21. Rogers et at 2002, Am. J. of Physiol. 282:E733-8;
22. Udry et al. 2001, EMBO J. 20:4467-7;
23. Hediger et al. 1989, PNAS, 86(5):5748-52;
24. Wells et al., 1992, Am. J. Physiol. 263(3):F459-65;
25. Kanai et al., 1994, J Clin Invest. 93(1):397-404;
26. Diez-Sampedro, 2003, PNAS, 100(20):11753-8;
27. Wood & Trayhurn, 2003, British J. Nutr. 89:3-9; 28. Wu etal., 2002, Genomics 80:553-7; 29. U.S. patent application No. 20030228592.

3.1 GLUTs

In some embodiments, the glucose transporter is a facilitative $Na^+$ independent sugar transporter or facilitative glucose transporter. "Facilitative glucose transporter" or "facilitative $Na^+$ independent sugar transporter" or "GLUT" refers to glucose transporters that utilize the diffusion gradient of their substrates such as glucose across plasma membranes to transport the substrates. Facilitative glucose transporters include, but are not limited to, GLUT1, GLU2, GLUT3, GLUT4, GLUT6, GLUT7, GLUT8, GLUT9, GLUT10, GLUT11, GLUT12, and H+-coupled myo-inositol transporter HMIT1. GLUT14 is 94.5% identical to GLUT3 and is also included in the GLUT family.

Facilitative glucose transporters generally possess 12 membrane-spanning helices. The transmembrane domain of the protein may contain a water-filled pathway through which the substrate moves and, in some cases, the exoplasmic domain of the protein can contain a large loop bearing an N-linked oliogosaccharide moiety. The loop can be formed between any of two consecutive transmembrane helices, for example, between the first and the second transmembrane helices, or between the ninth and the tenth transmembrane helices.

In some embodiments, the glucose transporter comprises one or more "glucose transporter signatures." "Glucose transporter signature" as used herein refers to conserved residues on two or more glucose transporters that have been implicated in the function of the protein as transporters. In some embodiments, the glucose transporter signature is the presence of seven glycine residues in transmembrane helices 1, 2, 4, 5, 7, 8, and 10. In some embodiments, the glucose transporter signature is one or more charged residues on the cytoplasmic surface of the protein that are conserved among the known GLUTs. See Joost et al., 2001, *Mol. Membrane Biol.* 18:247-256. In some embodiments, the glucose transporter signature is one or more of the following: tryptophan at helix 6, tryptophan at helix 11, tyrosine at helix 4, and tyrosine in helix 7. In some embodiments, the glucose transporter is a PXXPR motif after helix 6. In other embodiments, the glucose transporter does not comprise such a PXXPR motif In some embodiments, the glucose transporter signature is a tryptophan residue immediately following a conserved GXXPXP motif at helix 10 (corresponding to tryptophan 388 in GLUT1 when the sequence is aligned with GLUT1). In some embodiments, the glucose transporter signature is a tryptophan residue in helix 10 (corresponding to tryptophan 412 in GLUT1 when the sequence is aligned with GLUT1). These tryptophan residues have been shown to be important for binding of the ligands cytochalasin B and forskolin, and confer cytochalasin B or forskolin sensitivity to the glucose transporters. Garcia et al., 1992, *J. Biol. Chem.* 267:7770-76; Schurmann et al., 1993, *Biochem. J.* 290:497-501. Thus, some embodiments of the present invention encompass the assay of glucose transporters that are sensitive to cytochalasin B or forskolin treatment. In some embodiments, the glucose transporter has low binding affinity to cytochalasin B or forskolin. In some embodiments, the glucose transporter has high binding affinity to cytochalasin B or forskolin.

Glucose transporters assayed in the practice of the present invention have different affinities to glucose or glucose analogs. Accordingly, in some embodiments, the glucose transporter displays high affinity for glucose. As used in this context, for GLUTs, "high affinity" means a $K_M$ less than 5 mM using the *Xenopus* oocytes assay described in Burant et al., 1992, *J. Biol. Chem.* 267:14523-26; and for SGLTs "high affinity" means a $K_{0.5}$ less than 1 mM, preferably less than 0.5 mM, measured using the two-microelectrode clamp assay described in Panayotova-Heiermann et al., 1996, *J. Biol. Chem.* 271:10029-34. In other embodiments, the glucose transporter displays a low affinity for glucose. In some embodiments, the glucose/glucose analog-binding affinity of the glucose transporter varies in different tissues or under different physiological conditions, for example in a diseased state such as cancer.

Based on sequence similarities and characteristic elements, the set of known GLUT proteins can be divided into three smaller subsets, namely class I (GLUT1-4), class II (GLUT5, GLUT7, GLUT9, and GLUT11), and class III (GLUT6, 8, 10, 12, and HMIT1). See Joost et al., 2001, *Mol. Membr. Biol.* 18:247-56. Abnormal and/or over-expression of GLUTs is observed in some tumor tissues (see the review Smith, 1999, *Br. J. Biomed. Sci.* 564:285-92; Bell et al., 1990, *Diabetes Care* 13:198-206).

3.1.1 Class I GLUTs

Class I glucose transporters may comprise sequence motifs (a glucose transporter signature) such as a glutamine at helix 5 (corresponding to Q161 in GLUT1 when the sequence is aligned with GLUT1). In some embodiments, the glucose transporter comprises a STSIF motif in extracellular loop 7 (i.e., the loop between transmembrane helix 7 and transmembrane helix 8). In some embodiments, the glucose transporter comprises a QLS-motif at helix 7. Class I glucose transporters are reported to be expressed in various solid tumors such as breast cancer, renal cell carcinoma, brain tumors, gastrointestinal malignomas, and cervical carcinomas.

In some embodiments of the invention, levels of a Class I glucose transporter are measured.

In some embodiments of the invention, GLUT1 levels are measured. GLUT1 has been reported to be over-expressed in a variety of malignant tissues, including tumors of the bladder, breast, cervical, colorectal, gastric, esophageal, head and neck, leiomyosarcomas, lung, ovarian, pancreatic, penile, thyroid, uterous, vascular, and juvenile hemangiomas. Medina et al., 2002, *Biol. Res.* 35:9-26. Expression of GLUT1 has also been shown to correlate with tumor hypoxia. Airley et al, 2001, *Clin. Cancer Res.* 7:928-34; Chen et al. 2001, *J. Biol. Chem.* 12:9519-25.

In some embodiments of the invention, GLUT2 levels are measured. GLUT2 has been reported to be over-expressed in gastric cancer.

In some embodiments of the invention, GLUT3 levels are measured. GLUT3 has been reported to be over-expressed in brain cancer, lung cancer, breast cancer, gastric cancer, head and neck cancer, meningiomas, and ovarian cancer. GLUT3 has high affinity for glucose and is thought to be responsible for transport of glucose in tissues where the demand for glucose as a fuel is considerable, such as in the brain.

In some embodiments, GLUT4 levels are measured. GLUT4 has been reported to be over-expressed in breast cancer, gastric cancer, lung cancer, and pancreatic cancer.

In some embodiments, GLUT14 levels are measured. GLUT14 has two alternatively spliced forms: the shorter form of GLUT14 is a 497-amino-acid protein that is 94.5% identical to GLUT3. The long form is a 520 amino acid protein that differs from the short form only at the N-terminus. Both isoforms are reported to be specifically expressed in testis.

3.1.2 Class II GLUTs

In some embodiments, the glucose transporter is a class II GLUT. Ea some embodiments, the glucose transporter lacks a tryptophan residue following the conserved GXXPXP motif in helix 10 (corresponding to tryptophan 388 in GLUT1 when the sequence is aligned with GLUT1) that has been shown to confer cytochalasin B sensitivity to the glucose transporters. Class H glucose transporters are not sensitive to inhibition by cytochalasin B (see Joost et al., 2001, *Mol. Mem. Biol.* 18:247-56).

In some embodiments of the invention, levels of a Class II glucose transporter are measured.

In one embodiment of the invention, GLUT5 levels are determined. GLUT5 has been reported to be over-expressed in lung cancer and breast cancer.

In one embodiment of the invention, GLUT7 levels are determined.

In one embodiment of the invention, GLUT9 levels are determined. An alternatively spliced form of GLUT9 was recently identified that differs from GLUT9 only at the N-terminus. Auguatin et al., 2004, Jan. 22, *J. Biol. Chem.*

In some embodiment of the invention, GLUT11 levels are determined. Two splice variants have been described for GLUT11, a long form (503 amino acids) and a short form (493 amino acids). Doege et al., 2001, *Biol. J.* 359:443-49; Sasaki et al., 2001, *Biochem. Biophys. Res. Comm.* 289:1218-24. The short form GLUT11 has been reported to mediate low affinity glucose transport, and has been shown to be expressed predominantly in heart and skeletal muscle. The long form of GLUT11 has been reported to be expressed in liver, lung, trachea and brain, and was shown to increase fructose transport. Thus, in some embodiments of the present invention, the glucose transporter is the long form of GLUT11. In other embodiments, the glucose transporter is the short form of GLUT11. In yet other embodiments, the glucose transporter is a derivative, variant, or close homologue of GLUT11.

3.1.3 Class III GLUTs

In some embodiments, the glucose transporter is a class III GLUT. Motifs found in some Class III GLUTS include a glycosylation site on loop 9 (i.e., the loop between transmembrane helix 9 and transmembrane helix 10) and targeting motifs.

In some embodiments of the invention, levels of a Class III glucose transporter are determined.

In one embodiment of the invention, GLUT6 levels are determined. GLUT6 is reported to be predominantly expressed in brain, spleen and peripheral leukocytes.

In one embodiment of the invention, GLUT8 levels are determined. GLUT 8 is expressed in breast cancer cells.

In one embodiment of the invention, GLUT10 levels are determined.

In one embodiment of the invention, GLUT12 levels are determined. GLUT12 has been found to be expressed in breast tumors. See Rogers et al., 2003, *Cancer Letters,* 93:225-33; Rogers et al., 2002, *Am. J. Physiol. Endocrinol. Metab.* 282(3):E733-8.

In one embodiment of the invention, HMIT1 levels are determined.

3.2 SGLTs

In some embodiments, the glucose transporter is a $Na^+$-dependent glucose co-transporter. "Na+-dependent glucose transporter" or "$Na^+$/glucose co-transporter" refers to a glucose transporter that actively transports glucose or glucose analogs in an energy-dependent manner. Some $Na^+$-dependent glucose transporters utilize the movement of $Na^+$ down an electrochemical gradient to drive the uptake of glucose or glucose analogs. $Na^+$-dependent glucose transporters include, but are not limited to, SGLT1, SGLT2, SGLT3, SGLT4, SGLT5, and SGLT6. See Table 1; also see Coady et al., 2002, "Identification of a novel Na+/myo-inositol cotransporter." *J Biol Chem.* 277:35219-24. In some embodiments, the glucose transporter is a high affinity, low capacity $Na^+$-dependent glucose transporter. In some embodiments, the glucose transporter is a low affinity, high capacity Na+-dependent glucose transporter.

In some embodiments, the Na+-dependent glucose transporter encompasses 14 transmembrane helices. In some embodiments, the glucose transporter further comprises an N-linked glycosylation site between helix 6 and 7 that has been shown to be conserved among several known SGLTs. See Wright, *Am. J. Physiol. Renal Physiol.* 2001, 280(1):F10-8.

In one embodiment of the invention, SGLT1 levels are determined. SGLT1 has a high glucose affinity with a reported $Na^+$/glucose binding ratio of 2:1. SGLT1 has been reported to be expressed in several intestinal tumor cell lines and primary lung cancers. Bissonette et al., 1996, *Am. J. Physiol.*, 270:G833-G843; Delezay et al., 1995, *J. Cell Physiol.* 163:120-128; Ishikawa et al., 2001, *Jpn. J. Cancer Res.* 92:874-79.

In one embodiment of the invention, SGLT2 levels are determined. SGLT2 is a low affinity, high capacity transporter with a reported $Na^+$/glucose binding rate of 1:1.

In one embodiment of the invention, SGLT3 levels are determined. SGLT3 (formerly named SAAT1) has been reported to mediate transport of the chemotherapeutic agent β-D-glucosyllisophosphoramide mustard (D-19575) into tumor cells. Vehyl et al., 1998, *Proc. Natl. Acad. Sci. USA,* 95:2914-19. Recently, it has been proposed that SGLT3 is not a Na+/glucose cotransporter but instead a glucose sensor in the plasma membrane of cholinergic neurons, skeletal muscle, and other tissues (Diez-Sampedro et al., 2003, "A glucose sensor hiding in a family of transporters" *Proc. Natl. Acad. Sci. USA* 100:11753-8). Accordingly, in some embodiments of this invention, the glucose transporter for which a level is determined is not, or does not include, SGLT3.

In one embodiment of the invention, SGLT4 levels are determined.

In one embodiment of the invention, SGLT5 levels are determined.

In one embodiment of the invention, SGLT6 levels are determined.

It will be apparent that the level of a glucose transporter other than a transporter described in Table 1 may be measured in the practice of the invention. For example, derivatives, isoforms, variants, mutants, and homologs of any of the glucose transporters listed in Table 1, including homologs in other mammals, may be measured or their levels or activities measured. Further, the methods of the invention are applicable to glucose transporters that may be discovered in the future, such as a transporter with structure or sequence characteristic of known transporters (including, for example, a glucose transporter with at least 28%, at least 30%, at least 50%, at least 60%, at least 80%, at least 90% amino acid sequence similarity to a glucose transporter listed in Table 1).

4. Determining Susceptibility of a Cancer to Treatment with an Anti-Neoplastic Agent In one aspect, the methods of the present invention involve measuring the level of glucose transporter in a cancer sample from a patient. The level is compared to a reference value to determine whether the cancer, by virtue of expressing a high level of one or more transporters, is susceptible to treatment with an anti-neoplastic agent. As is explained in more detail below, in various aspects of the invention, levels of a single transporter in the cancer sample are measured, levels of multiple different transporters in the cancer sample are independently measured (i.e., a distinct value is determined for the level of each transporter) and/or two or more different transporters in the cancer sample are measured in a combined measurement (e.g., by assaying with a probe that recognizes more than one transporter or by assaying with multiple probes).

The word "level," as used herein, is intended to encompass any measurement reflective of the number of glucose transporters in the cancer sample and, in various embodiments, may be quantitative, semi-quantitative or relative (e.g., merely determined to be "greater than" or "less than" another similarly measured level). This number can be inferred from a wide variety of different measurements. For example, the number can be inferred from the amount of glucose transporter protein, the abundance of messenger RNA, or from glucose transporter activity in the sample. A number of assays that can be employed in the methods of the invention are described below and others will be apparent to the practitioner guided by this disclosure.

In some embodiments, the measurement of glucose transporters in the sample is normalized as an amount (or number) per cell, per gram tissue, per $mm^3$ tissue, or the like. As is known in the art, the transporter level in a cancer sample also can be normalized by reference to the abundance of a second protein in the sample, and the level of transporters expressed as a ratio of the amount of transporter protein to second protein. An advantage of such a method is that by selecting a protein that is expressed at a relatively constant level under different conditions, it is possible to minimize any effects of general inhibition of protein synthesis, cell apoptosis, or loss of materials during the assay process. Suitable "second proteins" include, without limitation, structural proteins, such as actin, tubulin, and glyceraldehyde-3-phosphate dehydrogenase. Comparable normalization can be used when transporter RNA levels are measured (e.g., by comparing transporter RNA levels with ribosomal RNAs or mRNA encoding a structural protein). In one aspect, glucose-6-phosphatase activity in the tumor is also measured and the glucose transporter level is expressed as a ratio of transporter (protein, RNA or activity) to glucose-6-phosphatase (G6Pase) protein, RNA or activity. A high ratio is indicative of increased susceptibility to treatment with an anti-neoplastic agent. Glucose and some glucose analogs are phosphorylated upon entry into a cell, resulting in accumulation and, in the case of certain analogs, increased toxicity due to accumulation of the phosphorylated forms in the cell. Expression and activity assays for glucose-6-phosphatase are known (see, e.g., Schmoll et al., 2001, *Cancer Letters*, 167:85-90; Taketa et al., 1998, *Cancer Res*. 48:467-74) In some embodiments, the ratio of the glucose transporter level over the glucose-6-phosphatase level is determined. The higher the ratio, the more susceptible the cancer of the patient to the treatment with an anti-neoplastic agent comprising glucose or a glucose analog.

In another embodiment, the transporter level in the cancer sample is expressed as a ratio of transporter level in the cancer sample to the transporter level in a matching non-tumor tissue from the same patient. A "matching non-tumor tissue" refers to a sample of non-cancerous tissue, preferably, a matching non-tumor or non-malignant sample is derived from the same organ as the organ from which the tumor sample is derived. Most preferably, the matching non-tumor sample is derived from the same organ tissue layer from which the tumor sample is derived. Also, it is preferable to take a matching non-tumor tissue sample at the same time a tumor sample is biopsied. For example, when obtaining tissues from a pancreatic tumor for purposes of the present invention, the practitioner can also obtain non-malignant pancreatic tissue from a location removed from the tumor. Then, glucose transporter levels are measured in each sample, and if the measured level in the tumor sample exceeds the level in the normal sample, then the tumor is determined to be susceptible to treatment with a glucose transporter anti-cancer agent.

In a related embodiment, the transporter level in the cancer sample is expressed as a ratio of transporter level in cancerous (transformed) cells in a cancer sample to the transporter level in non-cancerous cells from the same sample. This ratio can be conveniently determined, because when a cancer sample is obtained from a subject (e.g., by biopsy), the sample frequently also contains non-cancerous cells which can be identified by observation or using histological methods, or by detection of the absence of a cancer-specific molecular marker.

Although transporter levels are most often determined in a single cancer sample from a subject (and optionally a single non-cancer sample); in some embodiments, several biological samples of the cancerous and/or normal tissue are obtained from a single subject to obtain a mean value for the subject.

4.1. Reference Values

The level of expression of glucose transporters in the cancer sample is compared to a reference value to determine relative susceptibility to treatment with an anti-neoplastic agent. For a given transporter, it will be appreciated that the reference value for determining susceptibility to treatment may differ for different cancers. A variety of methods can be employed to determine the reference value for a particular transporter.

In one embodiment of the method, a reference value for a cancer type is determined by assessing transporter level(s) in cancer samples from a number of different patients, herein referred to as the "survey population." Generally, the patients in the survey population and the subject from whom the cancer sample is obtained all have the same type of cancer. For example, in one embodiment, pancreatic cancer samples from 10, 50, 100, 200, 500, or 1000 or more patients are analyzed for GLUT2 levels. Classification of cancer by "type" will be within the skill of, and at the discretion of, the practitioner. Usually the cancer "type" is based on the tissue of origin (e.g., pancreatic cancer, breast cancer, for example) but can also be based on stage, metastasis, degree of hypoxia, presence of prognostic markers, and the like. Another parameter for classifying cancer by type is the demonstrated effect of an anti-cancer agent or class of anti-cancer agents (including anti-neoplastic agents or a specific anti-neoplastic agent) in patients with the cancer "type". As used in this context, "effect" includes response (or lack thereof) to treatment with anti-cancer agent(s), length of increased survival of treated patients, and the like. In addition to being matched for cancer type, the survey population and subject also can be matched according to patient characteristics such as sex, age and ethnicity, and other criteria.

Transporter levels in the survey population (i.e., herein referred to as the "survey values") will form a distribution, which may be unimodal, bimodal or multimodal. In one embodiment of the invention, this distribution is used to determine the appropriate reference value, with, as previously discussed, cancers that express a level of transporter higher than the reference value being identified as susceptible to treatment with a neoplastic agent. The reference value can be a single cut-off value, such as a median or mean of the distribution of survey values in which patient samples with transporter values above the mean or median are identified as susceptible to treatment with an anti-neoplastic agent. In a related embodiment, the reference value is a percentile of the distribution of survey values, such as the $60^{th}$ percentile, the $75^{th}$ percentile, the $90^{th}$ percentile and the like. Alternatively, the reference value is a range, for example, where the distribution of survey values is divided into equal (or unequal) portions, such as quadrants, and each quadrant is correlated with a level of susceptibility to treatment (e.g., with the lowest quadrant correlated with least susceptibility and the highest quadrant correlated with the highest susceptibility). In some cases, the distribution of survey values is bimodal (with a low range and a high range). In such cases, cancer samples that have a glucose transporter level within or greater than the higher range are identified as originating from cancers susceptible to treatment with an anti-neoplastic agent. In some cases the distribution of survey values is multimodal (with a low range and more than one higher range). In such cases, cancer samples that have a glucose transporter level greater than the low range, and preferably within the higher of the higher ranges are identified as originating from cancers susceptible to treatment with an anti-neoplastic agent.

In some cases, the reference value may be zero or near zero, such as when a cancer type (for purposes of discussion, referred to herein as cancers of "tissue x") includes some tumors that do not express the specified glucose transporter or transporters and other tumors that do express the transporter or transporters. In such a case, any detectable expression of the transporter(s) is sufficient to indicate the patient is a candidate for treatment with an anti-neoplastic agent.

It will be appreciated that, so long as the units of the survey values (and thus the reference value) are the same as or similar to the units used to express transporter levels in the cancer sample (or, alternatively, the survey values and cancer sample levels can be otherwise compared), the particular method of describing transporter levels is not critical, but will depend on the nature of the cancer, the assay methods used, and the preference of the practitioner.

In another embodiment, the survey population is composed of subjects not having a cancer (e.g., healthy individuals), and a reference value for a cancer type is determined by assessing transporter level(s) in normal (non-malignant) samples from a matching tissue of subjects not diagnosed as having cancer (e.g., healthy subjects) who constitute a "survey population." The normal samples are matched to the cancer type in that they are derived from the same organ as the organ from which the tumor sample is derived, and preferably from the same tissue layer. The reference value is a value greater than the median or average of the normal values, and preferably is a value that is greater than that of 75% of the normal samples, often greater than that of 90% of the normal samples, sometimes greater than 95% or even greater than 99%.

Accordingly, the reference value may be determined using routine methods, e.g., collecting cancer samples (or normal samples) and determining transporter levels. Determination of particular threshold levels for assessing susceptibility of a tumor to treatment, selection of appropriate ranges, patient categories, cancer types, and the like are well within the skill of medical professionals guided by this disclosure. It will be understood that standard statistical methods may be employed by the practitioner in making such determinations. See, e.g., Principles of Biostatistics by Marcello Pagano et al. (Brook Cole; 2000); Fundamentals of Biostatistics by Bernard Rosner (Duxbury Press, 5th Ed, 1999); Biostatistics: a Foundation for Analysis in the Health Science by Wayne W. Daniels (John Wiley & Sons, 3rd Ed.; 1983); and Clinical Epidemiology and Biostatistics by Knapp and Miller (William and Wilkins, Harual Publishing Co. Malvern, Pa. 1992).

As is discussed in greater detail below, transporter levels may be determined for a single transporter. Alternatively, levels of several different transporters can be determined (e.g., simultaneously and/or in total without distinction as to the level of each). In a different embodiment, all of the transporters in the sample are assayed for the ability of the cell to transport a compound (such as a specified anti-neoplastic agent or a compound that should be transported by the same transporter that transports the specified anti-neoplastic agent).

4.2. Assays

Methods of determining glucose transporter levels in a biological sample are known in the art, and such assays are further described herein solely for illustration and convenience of the practitioner. Suitable methods include, for example, assays for the transporter proteins, assays for transporter RNAs and assays for transporter activity.

Assay methods are described below and in the Examples. The assays employ, unless otherwise indicated, conventional techniques of molecular biology (including recombinant techniques), microbiology, cell biology, biochemistry, nucleic acid chemistry, and immunology, all of which are within the skill of the ordinarily skilled artisan. Such techniques are explained fully in the literature, such as, MOLECULAR CLONING: A LABORATORY MANUAL, second edition (Sambrook et al., 1989) and MOLECULAR CLONING: A LABORATORY MANUAL, third edition (Sambrook and Russel, 2001) (the two previous citations being jointly referred to herein as "Sambrook"); CURRENT PROTOCOLS IN MOLECULAR BIOLOGY (F. M. Ausubel et al., eds., 1987, including supplements and revisions through 2003); PCR: THE POLYMERASE CHAIN REACTION (Mullis et al., eds., 1994); Harlow and Lane, 1988, ANTIBODIES, A LABORATORY MANUAL, Cold Spring Harbor Publications, New York, and Harlow and Lane, 1999, USING ANTIBODIES: A LABORATORY MANUAL Cold Spring Harbor Laboratory Press, Cold Spring Harbor, N.Y. (jointly referred to herein as "Harlow and Lane"), METHODS IN CELL BIOLOGY VOLUME 37: ANTIBODIES IN CELL BIOLOGY, Asai, ed. Academic Press, Inc. New York (1993); BASIC AND CLINICAL IMMUNOLOGY 7th Edition, Stites & Terr, eds. (1991); Hames et al., ed., NUCLEIC ACID HYBRIDIZATION, A PRACTICAL APPROACH IRL Press, (1985); and Beaucage et al., eds., CURRENT PROTOCOLS IN NUCLEIC ACID CHEMISTRY, 2000, John Wiley & Sons, Inc., New York).

The selection of a particular assay method for a given patient is, in view of this disclosure, within the skill of the practitioner, and can depend on a number of factors, including the type and stage of the cancer, whether a resection has been performed, the availability of cancer samples, and their type, which can be, for example, tissue specimens or extracts or cells or cell lysates or extracts or supernatants from the same, as well as the convenience of the practitioner and the availability and cost of reagents.

4.2.1 Biological Samples

Levels of glucose transporters in a cancer sample or in non-cancerous tissue can be determined by obtaining a biological sample from a subject and detecting the presence or amount of glucose transporter protein, MRNA, transporter activity, and other markers for transporter expression. For convenience, the term "cancer sample" is used to refer to the material (either cellular or cell derived) in which glucose transporters are measured. Generally, the cancer sample is from a human. Transporter levels can be measured in tissue specimens, tissue extracts, cells, cell lysates, cell extracts, body fluids, supernatants from preneoplastic cell lysates, or supernatant from neoplastic lysates using methods known in the art.

The cancer sample can be obtained from, and the methods of the present invention applied to, any cancer, including but not limited to leukemia, breast cancer, skin cancer, bone cancer, prostate cancer, liver cancer, lung cancer, brain cancer; cancer of the larynx, gallbladder, rectum, parathyroid, thyroid, adrenal, neural tissue, head and neck, colon, stomach, bronchi, and kidneys; basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, islet cell carcinoma, primary brain tumor, acute and chronic lymphocytic and granulocytic tumors, hairy-cell tumor, adenoma, hyperplasia, medullary carcinoma, pheochromocytoma, mucosal neuromas, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, and epidermoid carcinomas.

Methods of obtaining tissue samples are well known in the art and will vary according to the type and location of a tumor and preferences of the physician. In one embodiment, the sample is obtained from surgically excised tissue. Tissue samples and cellular samples can also be obtained without invasive surgery, for example by punctuating the chest wall or the abdominal wall or from masses of breast, thyroid or other sites with a fine needle and withdrawing cellular material (fine needle aspiration biopsy).

In another embodiment, the biological samples are bodily fluids that may contain cancer cells, which can be, for example, blood, breast exudate (e.g., nipple aspirate fluid), fecal suspensions, sputum, mucous, urine, lymph, cytosols, ascites, pleural effusions, amniotic fluid, or bladder washes.

The biological samples obtained can be used in fresh, frozen, or fixed (e.g., paraffin-embedded) form, depending on the nature of the sample, the assay used, and the convenience of the practitioner. Although fresh, frozen and fixed materials are suitable for various RNA and protein assays, generally, fresh tissues will be preferred for ex vivo measurements of activity.

Fixed tissue samples can also be employed. Tissue obtained by biopsy is often fixed, usually by formalin, formaldehyde, or gluteraldehyde, for example, or by alcohol immersion. Fixed biological samples are often dehydrated and embedded in paraffin or other solid supports, as is known in the art. See the reference Plenat et al., 2001, *Ann. Pathol.* 21:29-47. Non-embedded, fixed tissue, as well as fixed and embedded tissue, can be used in the present methods. Solid supports for embedding fixed tissue can be removed with organic solvents to enable subsequent rehydration of preserved tissue.

In some cases, the assay for transporter levels includes a step of cell or tissue culture. Culture methods are well known in the art. For example, cells from a biopsy can be disaggregated using enzymes (such as collagenase and hyaluronidase) and or physical disruption (e.g., repeated passage through a 25-gauge needle) to dissociate the cells, collected by centrifugation, and resuspended in desired buffer or culture medium for culture, immediate analysis, or further processing.

4.2.2 Protein-Based Detection

In one aspect of the invention, the level of glucose transporter is determined by measuring transporter protein. Most conveniently, this is done using an immunoassay (such as, without limitation, Western analysis, flow cytometry, EIA, ELISA, RIA, competition immunoassay, dual antibody sandwich assay, immunochemical, immunocytochemical and immunohistochemical methods, agglutination assay, and immunoprecipitation).

Antibodies for use in immunoassays are readily obtainable. Antibodies specific for glucose transporter proteins (including monoclonal and polyclonal antibodies, Fab and F(ab')$_2$ fragments, and recombinantly produced equivalents) can be prepared using routine methods. See, for example, Harlow and Lane, supra; Kohler and Milstein, 1975, *Nature* 256:495.

Antibodies can be generated by using a purified transporter protein, or portion thereof (whether purified from tissue or recombinantly expressed) as immunogen. Alternatively, a synthetic peptide or polypeptide sequence can be used to generate or select antibodies of interest. See, Huse et al., 1989, *Science* 246:1275-81; and Ward et al., 1989, *Nature* 341:544-46. For some assays it may be preferable to use an antibody that binds an extracellular region of a transporter(s), and such specificity can be obtained by using an extracellular epitope in generation or selection of the antibody. Likewise, antibodies can be selected that recognize an epitope found in more than one transporter (e.g., a conserved sequence) to allow simultaneous assays for multiple transporters. Table 1 provides accession numbers for DNA and protein sequences of selected transporter proteins and genes, which may be used to express or synthesize antigen.

Monoclonal and polyclonal antibodies for glucose transporters have been described in the scientific literature (see, Bukhard et al., 2004, *Oral Oncology*, 40:28-35 [anti-SGLT1]; Hasper et al., 1988, *J. Biol. Chem.* 263:398-403 [describing rabbit antiserum raised against a 13-amino acid peptide corresponding to the C-terminal of GLUT1]; Rogers et al., 2003, *Am. J. Physiol. Endocrinol. Metab.* 282:E733-738 [describing a rabbit polyclonal anti-GLUT12 antibody, R1396, raised to the unique 16 C-terminal amino acids of human GLUT12] and are widely available from commercial vendors [e.g. Research Diagnostics Inc., Alpha Diagnostics, Inc., East Acres Biologicals, DAKO, Hamburg, Germany, Chemicon International, Inc., Temecula, Calif., (see Table 2).

TABLE 2

Characteristics of Exemplary Commercially Available Antibodies

Rabbit anti-SGLT-1 (Antigen: Synthetic peptide corresponding to amino acids 402-420 of the putative extracellular loop of SGLT-1 of rabbit small intestine)
Rabbit anti-GLUT-1 [MYH antibody, advantageous because it detects extracellular region] (Antigen: 15 amino acid synthetic peptide corresponding to the exofacial loop of the human GLUT-1 (Thr-Trp-Asn-His-Arg-Tyr-Gly-Glu-Ser-Ile-Pro-Ser-Thr-Tbr-Leu)) (SEQ ID NO:18)
Rabbit anti- GLUT-2 (Antigen: Synthetic peptide (40-55 amino acid) corresponding to the exoplasmic loop between helices 1 and 2 of GLUT2)
Rabbit anti-GLUT-3 (Antigen: A 12 amino acid synthetic peptide corresponding to the carboxy terminus of human GLUT 3 (SIEPAKFETTTNV)) (SEQ ID NO:19)
Rabbit anti-GLUT-A (Antigen: Synthetic peptide corresponding to the C-terminus (amino acids 498-510) of mouse Glut-4)
Rabbit anti-GLUT-5 (Antigen: A 12 amino acid synthetic peptide specific for the carboxy terminus of the human GLUT 5 sequence (ELKELPPVTSEQ)) (SEQ ID NO:20)
Rabbit anti-GLUT-8 (Antigen: An 11 amino acid sequence near the C-terminus of mouse Glut-8).

There are a variety of protein-based approaches for detecting glucose transporter levels. For example, transporter proteins from a sample can be purified (e.g., by chromatography or electrophoresis) or enriched (e.g., by cell fractionation) and measured by Western analysis, or competitive or non-competitive immunoassays (such as ELISA or other sandwich assays) can be used, with or without such purification or enrichment of the transporter. Further guidance regarding the methodology and steps of a variety of antibody assays is provided, for example, in U.S. Pat. No. 4,376,110 to Greene; "Immunometric Assays Using Monoclonal Antibodies," in ANTIBODIES: A LABORATORY MANUAL, COLD SPRING HARBOR LABORATORY, CHAP. 14 (1988); Bolton and Hunter, "Radioimmunoassay and Related Methods," in HANDBOOK OF EXPERIMENTAL IMMUNOLOGY (D. M. Weir, ed.), Vol. 1, chap. 26, Blackwell Scientific Publications, 1986; Nakamura, et al., "Enzyme Immunoassays: Heterogeneous and Homogenous Systems," in HANDBOOK OF EXPERIMENTAL IMMUNOLOGY (D. M. Weir, ed.), Vol. 1, chap. 27, Blackwell Scientific Publications, 1986; and Coligan, supra.

For example, Western blot (immunoblot) analysis can be used to detect and quantify the presence of transporters in the sample. Western blots are useful for detecting glucose transporters in homogenized tissue samples and body fluid samples. Western blot techniques are routinely used in the art to determine protein levels in a sample. See Sambrook, supra. Generally, samples are homogenized and cells are lysed using a detergent such as TRITON-X. The material is then separated by gel electrophoresis, transferred to a suitable solid support (such as a nitrocellulose filter, a nylon filter, or derivatized nylon filter), and incubated with antibodies that specifically bind the transporter. These antibodies may be directly labeled or alternatively may be subsequently detected using labeled antibodies (e.g., labeled sheep anti-mouse antibodies) that specifically bind to the anti-transporter antibodies.

In another approach, immunohistological or immunocytological methods are used for assay of glucose transporter levels. Tissue sample preparation procedures are known in the art (see, e.g., Harlow, supra) and described in the Examples. Typically, tissue obtained by biopsy is fixed and embedded in paraffin or other solid supports, or placed on a solid support without embedding. Frozen sections may also be used. See Plenat et al., 2001, *Ann. Pathol.* 21(1):29-47. Further treatment of the tissue section prior to, during, or following the immunostaining may be carried out; for example, epitope retrieval methods, such as heating the tissue sample in citrate buffer may be carried out. See, e.g., Leong et al., 1996, *Appl. Immunohistochem.* 4:201. Following the optional blocking step, the tissue section is exposed to primary antibody (such as those described above, preferably those that bind to extracellular epitopes) for a sufficient period of time and under suitable conditions such that the primary antibody binds to the glucose transporter in the tissue sample. Appropriate conditions for achieving this can be determined by routine experimentation. The extent of binding of antibody to the sample can be assayed either directly or indirectly. For example, in one embodiment, a primary or secondary antibody is fluorescently labeled, and immunofluorescence microscopy is used to detect binding.

In another approach, anti-glucose transporter antibody is allowed to bind directly to cells (e.g., cells expressing transporters) and the antibody determined directly (e.g., using a fluorescent tag or an enzyme-labeled primary antibody) or indirectly (e.g., using a labeled secondary antibody). An example of such a binding assay is flow cytometry such as fluorescence activated cell analysis (see, e.g., Salih et al., 2000, *J. Immunology* 165:2903-10). Tumor tissue samples can first be dissociated prior to the FACS analysis. Specifically, tumors are exercised and minced in buffer. A tumor cell suspension is obtained by adding enzymes (such as collagenase and hyaluronidase) to dissociate the cells. Cells are then washed in washing buffer and passed several times through a 25-gauge needle. After centrifugation, cells are resuspended in a buffered solution. In an embodiment, the flow cytometry results are displayed as cell number vs. staining intensity (e.g,. number of transporters) and the distribution for the sample compared to those of a survey population.

Quantification of the expression of glucose transporters can be performed using any suitable method that is compatible with the assay. For example, for Western blot analysis, the intensity of the bands can be scanned and quantified. For immunohistochemistry analysis of tumor biopsy, the biopsy sections can be given a score according to the intensity of the glucose transporter staining, for example, 0 for no staining, 1 for light staining, 2 for medium staining, and 3 for heavy staining. In some embodiments, it is possible to distinguish membrane staining from cytoplasmic staining. In those embodiments, the membrane staining may be scored. For methods of quantitation, also see, for example, Raleigh et al., 2001, "Semiquantitative immunohistochemical analysis for hypoxia in human tumors" *Int. J. Radiat. Oncol. Biol. Phys.*, 2001 Feb. 1, 49(2):569-74 and Hatanaka et al., 2001, "Quantitative immunohistochemical evaluation of HER2/neu expression with HercepTest™ in breast carcinoma by image analysis" *Pathol. Int.* 51:33-6.

As discussed above, in some embodiments, the level of a reference protein, one relatively indifferent to cancer status, is also measured. Suitable reference proteins include actin, tubulin, and glyceralaldehyde-3-phosphate dehydrogenase. When a reference protein is employed, the glucose transporter level is "normalized" to the reference protein level by dividing the former by the latter. The resulting ratio is compared to a predetermined ratio as described herein.

4.2.3 RNA-Based Detection

In another embodiment, levels of glucose transporters are determined by measuring transporter mRNA levels. Assays for the messenger RNA levels of one or more glucose transporters in a sample include Northern analysis, polymerase chain reaction (PCR), including quantitative PCR, ligase chain reaction (LCR), RNase protection, in situ hybridization, serial analysis of gene expression (SAGE), differential display (DD) analysis, RNA arbitrarily primed (RAP)-PCR, restriction endonucleolytic analysis of differentially expressed sequences (READS), amplified restriction fragment-length polymorphism (AFLP), total gene expression analysis (TOGA), and use of internal standard competitive template primers (CTs) in a quantitative multiplex RT-PCR method [StaRT-(PCR)], high density cDNA filter hybridization (HDFCA) analysis, suppression subtractive hybridization (SSH), differential screening (DS), high-density cDNA or oligonucleotide arrays. For review, see, Ahmed, 2002, "Molecular techniques for studying gene expression in carcinogenesis" *J. Environ. Sci. Health Part C Environ. Carcinog. Ecotoxicol. Rev.* 20:77-116. Also see: Lipshutz et al. *Nat. Genet.* 1999, 21:20-4; U.S. Pat. Nos. 5,445,934; 5,578,832; 5,556,752; and 5,510,270; Schena et al., 1995, *Science* 270:467-70 (high density cDNA arrays); Lynn et al., 1983, *Proc. Natl. Acad. Sci.* 80:2656; Zinn et al., 1983, *Cell* 34:865; and Sambrook and Ausubel, supra (ribonuclease protection assays).

Methods for isolating RNA from tissues are well known (see, e.g., Ausubel, supra; Rapley et al., "RNA Isolation and Characterization Protocols" 1998. Humana Press, Inc. Totowa, N.J.; Farrell et al., "RNA Methodologies" 1993. Academic Press, Inc. San Diego, Calif.). RNA for amplification also can be isolated from fixed and/or paraffin-embedded tissue sections. See Stanta et al., "RNA Extracted from Paraffin-Embedded Human Tissues is Amenable to Analysis by PCR Amplification" *BioTechniques* 11 (3):304-308. 1991; Finke et al., "An Improved Strategy and a Useful Housekeeping Gene for RNA Analysis from Fonmalin-Fixed, Paraffin-Embedded Tissues by PCR" *BioTechniques* 14 (3):448-453. 1993; De Andres et al., "Improved Method for mRNA Extraction from Paraffin-Embedded Tissues. *BioTechniques* 18 (1): 42-43. 1995"; Rupp et al., "Purification and Analysis of RNA from Paraffin-Embedded Tissues". *BioTechniques* 6 (1):56-60. 1988; Sorg et al., "Detection of Boma Disease Virus RNA in Formalin-Fixed, Paraffin-embedded Brain Tissues by Nested PCR". *Journal of Clinical Microbiology* 33 (4):821-823. 1995; Werner et al., "Effect of formalin tissue fixation and processing on immunohistochemistry" *American Journal of Surgical Pathlology* 24 (7):1016-1019. 2000. See also, U.S. Pat. No 6,602,670, and publications cited in the specification and in the "references cited" section of that patent.

For illustration, in one embodiment, the level of glucose transporter is determined using quantative PCR. Quantative PCR refers to methods that are able to quantitate the amount of cDNA derived from reverse transcription of mRNA in cells from a tissue sample. The mRNA in the cells obtained from a tissue sample can be reverse transcribed by methods known in the art, including, for example, Sambrook, supra, and Ausubel, supra. Quantative PCR is carried out, for example, by amplifying RNA according to standard PCR methods using a primer which is modified to allow capture of the resulting product onto a solid surface. For example, the 5' or 3' primer can be biotinylated at the 5' terminus or 3' terminus, respectively, to allow capture of the resulting product onto avidin-coated microplates. The product attached to the solid surface is then quantitated, for example, by hybridizing to an oligonucleotide probe having a quantifiable label attached thereto. A "quantifiable label" can be, for example, a radioactive atom or group. The level of transporter mRNA expression is then assessed by determining the level of radioactivity in the sample. Alternatively, a "quantifiable label" is a group or moiety such as digoxigenin. In that embodiment, the PCR product is quantitated by addition of 1) an anti-digoxigenin antibody that is coupled with alkaline phosphatase and 2) a colorigenic substrate for alkaline phosphatase, followed by absorptometry. Optionally, the result can be normalized with respect to a cDNA standard curve.

A variety of so-called "real time amplification" methods or "real time quantitative PCP" methods can also be utilized to determine the quantity of glucose transporter mRNA present in a sample. Such methods involve measuring the amount of amplification product formed during an amplification process. Fluorogenic nuclease assays are one specific example of a real time quantitation methodology that can be used to detect and quantitate glucose transporter transcripts. In general, such assays continuously measure PCR product accumulation using a dual-labeled fluorogenic oligonucleotide probe, an approach frequently referred to in the literature simply as the "TaqMan" method. The probe used in such assays is typically a short (ca. 20-25 bases) polynucleotide that is labeled with two different fluorescent dyes. The 5' terminus of the probe is typically attached to a reporter dye and the 3' terminus is attached to a quenching dye, although the dyes can be attached at other locations on the probe as well. For measuring a glucose transporter transcript, the probe is designed to have at least substantial sequence complementarity with a probe binding site on a glucose transporter transcript. Upstream and downstream PCR primers that bind to regions that flank glucose transporter coding sequences are also added to the reaction mixture for use in amplifying the glucose transporter polynucleotide. When the probe is intact, energy transfer between the two fluorophors occurs and the quencher quenches emission from the reporter. During the primer extension phase of PCR, the probe is cleaved by the 5' nuclease activity of a nucleic acid polymerase such as Taq polymerase, thereby releasing the reporter dye from the polynucleotide-quencher complex and resulting in an increase of reporter emission intensity that can be measured by an appropriate detection system.

In one embodiment, in situ hybridization is used to detect glucose transporter sequences in a sample. In situ hybridization assays are well known and are generally described in Angerer et al., METHODS ENZYMOL. 152: 649-660 (1987). For example, in situ hybridization can be performed as described in Ruglowski et al., 2003, *Am. J. Clin. Pathol.* 120:691-698. Paraffin embedded tissue samples can be used. Briefly, the slides are pretreated with proteinase K and acetylation agents, and incubated with $^{33}$P-labeled sense and anti-sense cRNA riboprobes of glucose transporter RNAs. After incubation, the slides are washed in washing buffer, digested with RNase A, washed again, and subject to dehydration. After dehydration, slides are coated with silver emulsion and exposed for a certain amount of time (for example 8-10 days). The intensity of the silver stain can be examined using methods known in the art, for example by darkfield microscopy. Digitized images can also be examined. In situ hybridization methods are also described in Harris, 1996, *Anal. Biochem.* 243:249-256; Singer et al., 1986, *Biotechniques* 4:230-250; Haase et al, 1984, METHODS IN VIROLOGY, vol. VII, pp. 189-226; and NUCLEIC ACID HYBRIDIZATION: A PRACTICAL APPROACH (Hames et al., eds., 1987).

Quantitation of the expression of glucose transporters can be performed using any method that is compatible for the method of the assay.

Probes and primers useful for detection of glucose transporter protein RNAs are readily obtainable or can be prepared using routine methods based on the nucleotide sequences of glucose transporters. Primers useful for amplification-based detection can be readily designed based on knowledge of the target sequence (sequence to be detected). Particularly suitable primers for some assays have a $T_M$ close to 60° C., are between 100 and 600 bp in length and are specific for the region to be amplified (which can be determined by BLAST analysis of GenBank and the prospective primers, for example using software such as Oligo 6 (Molecular Biology Insights, Inc. Preferably, primers span an intron/exon splice junction so that amplification of desired RNA/cDNA can be easily separated from that of contaminating genomic DNA. It is well known that primers should be selected that do not form duplexes within themselves or with the other primer of the pair (if present) used for amplification. Probes and primers are described in the literature; see for example, Helmke et al., 2004, *Oral Oncology*, 40:28-35 (SGLT1, SGLT2); U.S. Patent Application No. 20030228592 (GLUT8); Rogers, 2003, *Cancer Letters* 193:225-33 (GLUT12, GLUT4); Brukhard et al., 2004, *Oral Oncology* 40:28-35 (SGLT1 and SGLT2); and Auguatin et al., Jan. 22, 2004, *J. Biol. Chem.* (GLUT9). Many other primers and probes are described in the scientific literature. Other probes and primers, for illustration and not limitation, are shown in Table 3. Other probes can be made by routine methods, for example, they can be amplified using primers listed in Table 3.

TABLE 3

| Gene | Primer Name | Primer Sequence | Primer Length (bp) | Tm (° C.) | CG % | Product size (bp) |
|---|---|---|---|---|---|---|
| GLUT1 | F_1_(1231 -> 1252) | TGACCATCGCGGTAGCACTGC (SEQ ID NO:21) | 21 | 61.7 | 61.9 | 759 |
| GLUT1 | R_2_(1969 <= 1990) | TCCACCCTCAGGCATGGAACC (SEQ ID NO:22) | 21 | 61.2 | 61.9 | |
| GLUT1 | F_4_(1341 -> 1362) | TGGTTCATCGTGGCTGAACTC (SEQ ID NO:23) | 21 | 57 | 52.4 | 1017 |
| GLUT1 | R_1_(2337 <= 2358) | TGAGTTTGCAGGCTCCCACAG (SEQ ID NO:24) | 21 | 59.5 | 57.1 | |
| GLUT1 | F_2_(1192 -> 1213) | TCATAGGCCTCGCTGGCATGG (SEQ ID NO:25) | 21 | 61.3 | 61.9 | 1171 |
| GLUT1 | R_3_(2342 <= 2363) | AGCAGTGAGTTTGCAGGCTCC (SEQ ID NO:26) | 21 | 59.8 | 57.1 | |
| GLUT2 | F_3_(980 -> 1001) | TGTCTGGTGTGCGAGCCATCC (SEQ ID NO:27) | 21 | 61.5 | 61.9 | 2295 |
| GLUT2 | R_3_(3254 <= 3275) | GATCAGTGCTCCAGTTGGTGG (SEQ ID NO:28) | 21 | 57.9 | 57.1 | |
| GLUT2 | F_2_(1232 -> 1253) | TGATGCTGCATGTGGCTCAGC (SEQ ID NO:29) | 21 | 60.3 | 57.1 | 2044 |
| GLUT2 | R_1_(3255 <= 3276) | TGATCAGTGCTCCAGTTGGTG (SEQ ID NO:30) | 21 | 56.9 | 52.4 | |
| GLUT2 | F_3_(980 -> 1001) | TGTCTGGTGTGCGAGCCATCC (SEQ ID NO:31) | 21 | 61.5 | 61.9 | 868 |
| GLUT2 | R_2_(1827 <= 1848) | ACAGCAGCTTTTGGCCTGTGG (SEQ ID NO:32) | 21 | 60.6 | 57.1 | |
| GLUT3 | F_1_(1451 -> 1472) | AGTGGCCGGCTGCTCCAAGTG (SEQ ID NO:33) | 21 | 64.2 | 66.7 | 2254 |
| GLUT3 | R_3_(3684 <= 3705) | AGACGGAGTCTCGCCCTGTGG (SEQ ID NO:34) | 21 | 62.5 | 66.7 | |
| GLUT3 | F_4_(1589 -> 1610) | AGTCCCTGAGACCCGTGGCAG (SEQ ID NO:35) | 21 | 62.7 | 66.7 | 700 |
| GLUT3 | R_1_(2268 <= 2289) | ACAAACCTGCACATTCGGCAC (SEQ ID NO:36) | 21 | 58.6 | 52.4 | |
| GLUT4 | F_2_(762 -> 783) | TGGGCCTCACAGTGCTACCTG (SEQ ID NO:37) | 21 | 60.9 | 61.9 | 379 |

TABLE 3-continued

| Gene | Primer Name | Primer Sequence | Primer Length (bp) | Tm (° C.) | CG % | Product size (bp) |
|---|---|---|---|---|---|---|
| GLUT4 | R_2_(1420 <= 1441) | AAGTTGCTCGTCCAGTTGGAG (SEQ ID NO:38) | 21 | 57 | 52.4 | |
| GLUT4 | F_3_(720 -> 741) | TGGAGTCCCTCCTGGGCACTG (SEQ ID NO:39) | 21 | 62.7 | 66.7 | 664 |
| GLUT4 | R_3_(1363 <= 1384) | TGGCTGAAGAGCTCGGCCACG (SEQ ID NO:40) | 21 | 63.6 | 66.7 | |
| GLUT4 | F_3_(720 -> 741) | TGGAGTCCCTCCTGGGCACTG (SEQ ID NO:41) | 21 | 62.7 | 66.7 | 721 |
| GLUT4 | R_2_(1420 <= 1441) | AAGTTGCTCGTCCAGTTGGAG (SEQ ID NO:42) | 21 | 57 | 52.4 | |
| GLUT5 | F_1_(102 -> 123) | TGCCCTGGCAACCCTGATAGC (SEQ ID NO:43) | 21 | 61.7 | 61.9 | 1071 |
| GLUT5 | R_2_(1152 <= 1173) | TATGGCATCCAGGACACTGTG (SEQ ID NO:44) | 21 | 56.5 | 52.4 | |
| GLUT5 | F_2_(619 -> 640) | GATGGCTGGCCGATCCTGCTG (SEQ ID NO:45) | 21 | 62.7 | 66.7 | 1229 |
| GLUT5 | R_1_(1827 <= 1848) | AGCCACGTTACCAGGAGCCAC (SEQ ID NO:46) | 21 | 61.3 | 61.9 | |
| GLUT5 | F_3_(148 -> 169) | GGGTACAACGTGGCTGCTGTC (SEQ ID NO:47) | 21 | 60.5 | 61.9 | 1025 |
| GLUT5 | R_2_(1152 <= 1173) | TATGGCATCCAGGACACTGTG (SEQ ID NO:48) | 21 | 56.5 | 52.4 | |
| GLUT6 | F_1_(482 -> 503) | ACAGCTGCCTGCATCCCGGTG (SEQ ID NO:49) | 21 | 64.2 | 66.7 | 991 |
| GLUT6 | R_7_(1452 <= 1473) | TGAACACCAGGCTCACCAAGC (SEQ ID NO:50) | 21 | 59.7 | 57.1 | |
| GLUT6 | F_2_(762 -> 783) | TCGATGTCCACTGGGAGTTCG (SEQ ID NO:51) | 21 | 58.3 | 57.1 | 980 |
| GLUT6 | R_1_(1721 <= 1742) | AGCAGTGCTACCTGTCCCGAG (SEQ ID NO:52) | 21 | 60.5 | 61.9 | |
| GLUT6 | F_3_(266 -> 287) | ACCAAATCCCAGGCATCCTGG (SEQ ID NO:53) | 21 | 59.5 | 57.1 | 1485 |
| GLUT6 | R_4_(1730 <= 1751) | TGGCTGGACAGCAGTGCTACC (SEQ ID NO:54) | 21 | 61.3 | 61.9 | |
| GLUT8 | F_1_(956 -> 977) | TCCAGGTGCTGTTCACAGGTG (SEQ ID NO:55) | 21 | 59.4 | 57.1 | 775 |
| GLUT8 | R_4_(1710 <= 1731) | ACCGCAGGTCTGCAAAGCTCG (SEQ ID NO:56) | 21 | 62 | 61.9 | |
| GLUT8 | F_2_(944 -> 965) | TCGTGGGTGTCATCCAGGTGC (SEQ ID NO:57) | 21 | 61.3 | 61.9 | 588 |
| GLUT8 | R_5_(1511 <= 1532) | AGCTTGGAGTCACAGGCTTGC (SEQ ID NO:58) | 21 | 59.8 | 57.1 | |
| GLUT8 | F_1_(956 -> 977) | TCCAGGTGCTGTTCACAGCTG (SEQ ID NO:59) | 21 | 59.4 | 57.1 | 416 |
| GLUT8 | R_3_(1351 <= 1372) | TCCATAGGGCCTGAGGACCTC (SEQ ID NO:60) | 21 | 59.7 | 61.9 | |
| GLUT9 | F_2_(3 -> 24) | TGGCTCTAGGGCTGGCACCAG (SEQ ID NO:61) | 21 | 63.2 | 66.7 | 668 |
| GLUT9 | R_2_(650 <= 671) | AGCCACGGATCTCCTTGGGTG (SEQ ID NO:62) | 21 | 61 | 61.9 | |

TABLE 3-continued

| Gene | Primer Name | Primer Sequence | Primer Length (bp) | Tm (° C.) | CG % | Product size (bp) |
|---|---|---|---|---|---|---|
| GLUT9 | F_1_(422 -> 443) | TCGCCATCGGTGGACTTGTGG (SEQ ID NO:63) | 21 | 61.4 | 61.9 | 612 |
| GLUT9 | R_1_(1013 <= 1034) | TCACGGTGACCACGTGCCAGC (SEQ ID NO:64) | 21 | 63.8 | 66.7 | |
| GLUT10 | F_1_(1068 -> 1089) | ACTCAGGCCCAAGCTGTCTGG (SEQ ID NO:65) | 21 | 61.3 | 61.9 | 1256 |
| GLUT10 | R_1_(2303 <= 2324) | TGGTTGCATGCGCCTGTAGTC (SEQ ID NO:66) | 21 | 59.9 | 57.1 | |
| GLUT10 | F_4_(1642 -> 1663) | ACGGTTCACCCTGAGCTTTGG (SEQ ID NO:67) | 21 | 59.5 | 57.1 | 1591 |
| GLUT10 | R_2_(3212 <= 3233) | TGGCAAAGCCAGCTCCAGCAC (SEQ ID NO:68) | 21 | 62.7 | 61.9 | |
| GLUT11 | F_1_(701 -> 722) | TCTTTACGGCTCTGGGGATCG (SEQ ID NO:69) | 21 | 58.2 | 57.1 | 561 |
| GLUT11 | R_4_(1241 <= 1262) | AGCAGGTCATCAGGCTGTACC (SEQ ID NO:70) | 21 | 58.6 | 57.1 | |
| GLUT11 | F_2_(211 -> 232) | TCCTTACGGCCTCGGACGCAG (SEQ ID NO:71) | 21 | 62.8 | 66.7 | 951 |
| GLUT11 | R_3_(1141 <= 1162) | AGTCCCGATGATCGCGTACTG (SEQ ID NO:72) | 21 | 58.2 | 57.1 | |
| GLUT11 | F_3_(749 -> 770) | AGCTCCTAGGTGGCCCTCAGG (SEQ ID NO:73) | 21 | 62.4 | 66.7 | 657 |
| GLUT11 | R_6_(1385 <= 1406) | ACAGCTCTGTGGCCAGGATCC (SEQ ID NO:74) | 21 | 61.1 | 61.9 | |
| GLUT11 | F_5_(450 -> 471) | TGGAGCACTGCTTGCAGGTCC (SEQ ID NO:75) | 21 | 61.9 | 61.9 | 615 |
| GLUT11 | R_7_(1044 <= 1065) | TCCATGGCACTGCCCAGAACC (SEQ ID NO:76) | 21 | 61.9 | 61.9 | |
| GLUT12 | F_1_(541 -> 562) | ACGCATTGCCATAGGGGTCTC (SEQ ID NO:77) | 21 | 59.2 | 57.1 | 1061 |
| GLUT12 | R_2_(1581 <= 1602) | TCTCGCTGAGCACCAGCCAGG (SEQ ID NO:78) | 21 | 63.3 | 66.7 | |
| GLUT12 | F_4_(1091 -> 1112) | TCCACTGGGGTTGGAGTCGTC (SEQ ID NO:79) | 21 | 60.5 | 61.9 | 1384 |
| GLUT12 | R_1_(2454 <= 2475) | TGGGCAGTTGTCCACACTGTG (SEQ ID NO:80) | 21 | 59.7 | 57.1 | |
| GLUT12 | F_4_(1091 -> 1112) | TCCACTGGGGTTGGAGTCGTC (SEQ ID NO:81) | 21 | 60.5 | 61.9 | 511 |
| GLUT12 | R_2_(1581 <= 1602) | TCTCGCTGAGCACCAGCCAGG (SEQ ID NO:82) | 21 | 63.3 | 66.7 | |
| SGLT1 | F_1_(1083 -> 1104) | AGGTTGGCTGTACCAACATCG (SEQ ID NO:83) | 21 | 57.1 | 52.4 | 477 |
| SGLT1 | R_1_(1539 <= 1560) | AGTTGCTGGGCTCCATGCAGC (SEQ ID NO:84) | 21 | 62.5 | 61.9 | |
| SGLT1 | F_4_(209 -> 230) | TGGTGGCCGATTGGAGCCTCC (SEQ ID NO:85) | 21 | 63.7 | 66.7 | 1143 |
| SGLTI | R_2_(1331 <= 1352) | TGCTGACTGCACAATGGGCAC (SEQ ID NO:86) | 21 | 60.5 | 57.1 | |
| SGLT1 | F_3_(1122 -> 1143) | TGGAGCTCATGCCCAATGGAC (SEQ ID NO:87) | 21 | 59.6 | 57.1 | 964 |

TABLE 3-continued

| Gene | Primer Name | Primer Sequence | Primer Length (bp) | Tm (° C.) | CG % | Product size (bp) |
|---|---|---|---|---|---|---|
| SGLT1 | R_3_(2065 <= 2086) | TCCCTTCAACACCACAGGACG (SEQ ID NO:88) | 21 | 58.9 | 57.1 | |
| SGLT2 | F_2_(175 -> 196) | TGGGCGGCTACTTCCTGGCAG (SEQ ID NO:89) | 21 | 63.5 | 66.7 | 909 |
| SGLT2 | R_4_(1063 <= 1084) | ACACGCGCCTGCACACCTCAG (SEQ ID NO:90) | 21 | 64.2 | 66.7 | |
| SGLT2 | F_3_(394 -> 415) | TGCCACAGTACCTGCGCAAGC (SEQ ID NO:91) | 21 | 62.3 | 61.9 | 758 |
| SGLT2 | R_1_(1131 <= 1152) | ACCGTTGGGCATGAGCTTCAC (SEQ ID NO:92) | 21 | 60 | 57.1 | |
| SGLT2 | F_4_(894 -> 915) | TGCAGCGACCAGGTCATCGTG (SEQ ID NO:93) | 21 | 61.5 | 61.9 | 449 |
| SGLT2 | R_7_(1322 <= 1343) | AGCCAGGCCACCGACACTACC (SEQ ID NO:94) | 21 | 63.2 | 66.7 | |
| SGLT5 | F_6_(643 -> 664) | TCGCAGCTTTTGACCAGATCG (SEQ ID NO:95) | 21 | 57.4 | 52.4 | 934 |
| SGLT5 | R_7_(1556 <= 1577) | TGCTCGTTGGCACGTCGCCAG (SEQ ID NO:96) | 21 | 64.2 | 66.7 | |
| SGLT5 | F_1_(843 -> 864) | TGCACCGACCAGGTCATCGTG (SEQ ID NO:97) | 21 | 61.3 | 61.9 | 597 |
| SGLT5 | R_1_(1419 <= 1440) | ACTCACGCCGATGAGTGCCAC (SEQ ID NO:98) | 21 | 61.5 | 61.9 | |
| SGLT5 | F_2_(739 -> 760) | TGCCACGTACAGACGCCATGC (SEQ ID NO:99) | 21 | 62 | 61.9 | 745 |
| SGLT5 | R_5_(1463 <= 1484) | AGTTGCCCGCTGTTGGAGTCC (SEQ ID NO:100) | 21 | 61.8 | 61.9 | |

4.2.4 Functional Assays

In one embodiment, the level of glucose transporters is determined by measuring glucose transporter activity, e.g., uptake of glucose or a glucose analog in vitro or in vivo. For example, the activity of a glucose transporter may be measured in vitro in a glucose uptake assay. Glucose uptake assays are known in the art (see e.g., Gnudi et al., 1997, *Mol. Endocrinol.* 11:67-76; see also PCT Publication WO 03/082301). In one version, for illustration, and not limitation, a glucose uptake assay measures uptake of a labeled hexose. Cells are obtained by dissociation of tumor tissue samples, as described above. Optionally cells are cultured, and optionally subcultured to confluence, and then detached and resuspended. The cells are then incubated in the presence or absence of cytochalasin B (for GLUTs) or phlorizin (for SGLTs) with radio-labeled (for example, $^{14}$C- or $^3$H- labeled) glucose or glucose analogs (such as 2-deoxyglucose). After incubation, the cells are washed and analyzed for radioactivity. Cytochalasin B inhibits Class I and Class III glucose transporters and so is useful for assessing activity of such transporters. Phlorizin inhibits SGLTs and so is useful for assessing activity of such transporters.

In some embodiments, the levels of SGLTs are measured, and the glucose analog a-methyl-D-glucoside (a-MDG) is used. The a-MDG can be transported in a sodium-dependent manner with apparent affinity ($K_{0.5}$) of 0.4 (SGLT1) and 2 mM (SGLT2 and SGLT3). In some embodiments, the glucose analogs are transferred only by one or a small number of specific glucose transporters, so that the uptake of glucose tracers directly correlates with the expression levels of those glucose transporters. For example, it has been reported that an increased glucose uptake of cervical cancer cells was related to an exclusive transmembranous over-expression of GLUT1. An increased glucose uptake in glucose uptake assays thus indicates an increased expression of GLUT1.

In some embodiments, the glucose analogs are transported by more than one glucose transporter. The amount of total glucose uptake will thus correlate with the overall level of glucose transporters expressed by the cells.

Another assay for assessing the expression level of glucose transporters is the cytochalasin B binding assay (see Ogura et al., 1999, *J. Endocrinology*, 160:443-452; Ozaki et al., 1996, *Mech Ageing Dev.* 88:149-158; and Gorga & Lienhard, 1981, *Biochem.* 20:5108-13). Briefly, membrane extracts are prepared from the tissue or cell sample and mixed with radio-labeled (such as $^3$H-labeled) cytochalasin B. At the end of the reaction, the membrane-bound and free cytochalasin B are separated (for example by filtration or by centrifugation). The membrane portion is counted for radioactivity. The level of cytochalasin B binding is correlated with the level of GLUTs.

In another embodiment, the level of glucose transporters is determined by measuring glucose uptake in vivo. A correlation between glucose transporter expression and glucose uptake is made in this method. For example, Kato et al., 2003,

*Anti-Cancer Res.* 23:3263-72, reported a correlation of 18-F-fluorodeoxyglucose accumulation with GLUT1 expression in esophageal squamous cell carcinoma. Glucose uptake assays are known in the art. See, e.g., Reske et al., 1997, *J. Nucl. Med.*, 38:1344-48. Generally, glucose uptake is assessed with nonmetabolizable glucose analogues, such as 2-fluorodeoxyglucose (2-FDG), 2-deoxyglucose (2-DG), and 3-O-methylglucose. Glucose transporter activity can be determined, for example, by positron emission tomography using a fluorescently labeled glucose analog.

5. Selection of Anti-Neoplastic Agents

Certain anti-neoplastic agents are preferentially transported by certain glucose transporters. For example, the drug streptozotocin is transported into pancreatic cancer cells by the GLUT2 transporter. Detection of a high level of GLUT2 transporter in a cancer tissue provides, in accordance with the methods of the invention, a basis for predicting that the tumor is susceptible to treatment with streptozotocin. In general, the higher the level of a particular transporter the more susceptible the tumor to treatment with an anti-neoplastic agent transported by the particular transporter.

Thus, in some embodiments, the amount of a glucose transporter is determined before an anti-neoplastic agent is selected for the treatment. Once the glucose transporter level is found to be larger than a predetermined amount, a determination of that the cancer is susceptible to the treatment of a particular anti-neoplastic agent is then made. The choice of the anti-neoplastic agent can be based on a number of factors, including, but not limited to, statistical analysis or substrate specificity of the glucose transporter.

In some embodiments, the glucose transporter is known to specifically transport a certain anti-neoplastic agent. A correlation is then immediately made between the larger amount of the glucose transporter and the susceptibility to that anti-neoplastic agent. For example, glucofosfamide, also known as glufosfamide, has been reported to be transported by SGLT1. A larger amount of SGLT1 than a predetermined amount is then indicative, in accordance with the methods of the invention, that the cancer is susceptible to treatment with glucofosfamide. In another embodiment, the glucose transporter is known to transport a certain class of anti-neoplastic agents. For example, GLUT2 is known to transport glucose analogs with a non-modified 2-position.

In some embodiments, the anti-neoplastic agent is preselected, and the level of a glucose transporter for which the agent is a substrate is determined to see whether a patient has a cancer of a type that is susceptible to such treatment. If the cancer sample from the patient has a level of a glucose transporter higher than a reference value, the patient is treated with the anti-neoplastic agent.

An agent can be identified as a substrate of a particular transporter using art-known methods (as described below). Alternatively, a correlation between levels of a transporter and susceptibility to an agent can be established by identifying a population of patients for whom the agent has proven effective, and determining what transporters are expressed. A level or expression profile for a particular patient can then be compared with the reference profile for the population for whom the treatment has proved effective.

A variety of substrate assays may be used. For example, hexose uptake and competition assays carried out in primary cell cultures or in *Xenopus oocytes* has been routinely used to determine whether a glucose transporter transports a particular substrate. See, e.g., Garcia et al., 2003, *J. Neurochemistry*, 86:709; Burant et al., *J. Biol. Chem.*, 1992, 267:14523-6; and Veyhl et al., 1998, *Proc. Natl. Acad. Sci. USA* 95:2914-29.

Sense cRNAs from the glucose transporter can be prepared as described in Veyhl et al. and injected into defolliculated *Xenopus* oocytes. The oocytes are incubated in the presence or absence of cytochalasin B (for GLUTs) or phlorizin (for SGLTs) containing various radio-labeled ($^{14}C$, $^{3}H$, etc) glucose or glucose analogs to be tested. After incubation, radioactivity in the oocytes can be analyzed. For SGLTs, the electric properties of the glucose or glucose analog uptake can be analyzed by employing the two-microelectrode voltage-clamp techniques.

Other assays are done in primary cells, such as human carcinoma cells, that are known to express a particular glucose transporter. Cells are grown and subcultured to confluence and then detached and resuspended. The cells are then incubated in the presence or absence of cytochalasin B (for GLUTs) or phlorizin (for SGLTs) with various radio-labeled (for example, $^{14}C$- or $^{3}H$- labeled) glucose or glucose analogs to be tested. After incubation, the cells are washed and analyzed for radioactivity.

In a related aspect of the invention, an in vitro activity assay is used to determine the susceptibility of a particular tumor (or tumor type) to a particular anti-neoplastic agent. According to this method, cells from the tumor are incubated with the anti-neoplastic agent at a variety of concentrations bracketing the estimated in vivo concentration when the agent is administered to a human patient. After one of more time intervals (e.g., 10 m, 30 m, 1 h, and 3 h) the effect of the agent on cell growth and viability is determined and compared to controls in which no agent was added and/or controls in which different anti-neoplastic agents or different anti-cancer agents were added. A reduction in cell growth compared to controls (e.g., as assessed by measuring cell number or a surrogate such as DNA content) or a reduction in viability (e.g., as assessed by monitoring apoptosis in the culture) is an indication that the tumor is susceptible to the agent. In one embodiment, a panel of several (e.g., at least 2, at least 3, at least 4, at least 5 or at least 10) different agents are screened according to this method to identify the most promising candidates for administration to the patient.

6. Devices and Methods for Measuring Levels of Transporters Including Multiple Transporters A number of methods for determining levels of glucose transporters are described herein, and other methods will be apparent to one of skill in the relevant arts upon consideration of this disclosure. In some embodiments of the invention, only one of the assay methods is used for the determination of the glucose transporter levels. In other embodiments, two or more methods are used in combination to determine the glucose transporter levels. For example, samples showing high expression levels of glucose transporters by immunohistochemistry assays may be further processed to quantify the protein level by Western blot assays, if such information is useful to the practitioner. Similarly, samples showing high glucose uptake may be further examined for the protein or mRNA levels of glucose transporters.

In some embodiments, the expression level of only one glucose transporter is measured. In other embodiments, the expression levels of two or more glucose transporters are measured. The measurement of two or more glucose transporters can be done sequentially or simultaneously.

In some embodiments, the expression of more than one glucose transporters is measured. This is particularly relevant when multiple glucose transporters are expressed in the same tissue. The practitioner may (1) determine which transporters are expressed at a level higher than the reference value for that tissue by assaying for several transporters; (2) select anti-neoplastic agents based on the knowledge of which drugs are transported by which transporters.

For example, multiple glucose transporters, including GLUT1, GLUT4, GLUT5, GLUT8, GLUT12, and HMIT have all been shown to be expressed in adipocytes. The detection of multiple glucose transporters can be done by methods that allow the detection or measurement of multiple glucose transporters, either sequentially or simultaneously.

Methods of simultaneous measurement of the expression levels of more than one protein is known in the art and the further description provided herein is for illustrative purposes only. For example, microarray analysis can be applied at both the RNA and protein levels, including for the determination of levels of more than one transporter protein or RNA.

Methods for measuring levels of multiple RNA species expressed in a cell or tissue are well known and include high-density polynucleotide or oligonucleotide arrays (Lipshutz et al., *Nat. Genet.*, 1999, 21:20-4; U.S. Pat. Nos. 5,445,934; 5,578,832; 5,556,752; and 5,510,270), high density cDNA arrays (see, e.g., Schena et al., 1995, *Science* 270:467-7), dot and slot blots, dip sticks, pins, chips, or beads. All of these techniques and devices are well known in the art and are the basis of many commercially available diagnostic kits. These techniques can be easily adapted, guided by the present disclosure, to measuring levels of glucose transporters.

In some embodiments, the levels of the glucose transporter(s) are determined using a protein array. "Protein arrays" contain different capture agents immobilized at different positions on a solid support that allow independent interaction between each capture agent and its respective target protein. The capture agents can be any molecules that selectively bind to the target protein, such as antibodies, recombinant proteins, and small chemicals. Protein arrays may be used to determine quantities of specific proteins in a sample. See, Von Eggeling et al., 2000, *BioTechniques* 29:1066-70; Haab, *Proteomics*, 3:2116-22; Wiesner, 2003, *J. Lab. Medicine* 27:85-91; Kodadek 2002, *Trends Biochem. Sci.* 27:295-300.

In some embodiments of the invention, levels for only one, or a small number, of glucose transporters are measured. In some cases, for example, the patient's cancer is known to associate at some frequency with the over-expression of a particular glucose transporter. For example, GLUT1 over-expression has been reported to be associated with bladder cancer, breast cancer, cervical cancer, colorectal cancer, esophageal cancer, gastric cancer, head and neck cancer, leiomyosarcomas, ovarian cancer, and thyroid cancer. Accordingly, in one embodiment of the invention, the level of GLUT1 in a cancer sample from a subject with bladder cancer, breast cancer, cervical cancer, colorectal cancer, esophageal cancer, gastric cancer, head and neck cancer, leiomyosarcomas, ovarian cancer, or thyroid cancer is determined.

GLUT2 over-expression has been reported to be associated with pancreatic cancer or gastric cancer. Accordingly, in one embodiment of the invention, the level of GLUT2 in a cancer sample from a subject with pancreatic cancer or gastric cancer is determined. In one embodiment, the cancer is a pancreatic cancer, and the level of GLUT2 in the cancer sample is measured, and the anti-cancer agent is selected from the group consisting of streptozotocin, glucofosfamide, and a gluSNAP compound.

GLUT3 over-expression has been reported to be associated with brain cancer or lung cancer. Accordingly, in one embodiment of the invention, the level of GLUT3 in a cancer sample from a subject with brain cancer or lung cancer is determined.

In some embodiments, the correlation between the cancer and the glucose transporter over-expression will be unknown. In these embodiments, a correlation between the glucose transporter and different types of cancer is first established by methods such as expression profiling before the levels of a selected glucose transporter is determined in a patient. Alternatively, one may simply measure the total level of transporter in a cancer sample and administer the drug if the total level exceeds the reference level by the requisite amount selected for administration of the drug.

7. Kits and Devices

In one aspect the invention provides kits and devices for screening patient tumors to determine susceptibility to particular anti-neoplastic agents.

Kits of the invention comprise reagents for assessing expression of one or more glucose transporter genes, such as probes and/or primers for detection or amplification of glucose transporter gene products. In one embodiment, the probes are nucleic acid probes or primers that specifically bind to one or more polynucleotides transcribed from a glucose transporter gene. In one embodiment, the kit contains antibodies specific for one or a plurality (at least 2, preferably 3, often 4, sometime 5 or more) of different human glucose transporters. The kit of the invention may optionally comprise additional components useful for performing the methods of the invention, such as devices for use in dissociating cells or isolating proteins or nucleic acids from cells. In addition, the kits may contain calibration curves, a reference sample (or protein or nucleic acid) for comparison to a predetermined value, and/or reference values (e.g., in table format) as described herein.

The present invention also provides kits for determining the level or amount of glucose transporters in human tissue or body fluid samples. In one embodiment, the kits comprise diagnostic screening reagents and instructions for the use thereof in the present method.

The invention also provides devices useful for the screening methods of the invention. In one aspect, a device comprising immobilized probe(s) specific for one or more glucose transporter gene products (polynucleotides or proteins) is provided. The probes can bind polynucleotides (e.g., based on hybridization), polypeptides or cells expressing polypeptides.

In some embodiments, a device comprising a single immobilized probe is used for screening. In one embodiment, an array format is used in which a plurality (at least 2, usually at least 4 or more) of different probes is immobilized. The term "array" is used in its usual sense and means that each of a plurality of probes, immobilized on a substrate, has a defined location (address) on the substrate. The number of probes on the array can vary depending on the nature and use of the device. For example, a dipstick format array for detecting glucose transporters can have as few as 1 probe, although usually at least 2, or more than 2, distinct probes are present.

A variety of binding and hybridization formats are known, including oligonucleotide arrays, cDNA arrays, dip sticks, pins, chips, or beads, Southern, northern, dot and slot blots. Thus a device comprising a probe for a glucose transporter gene product immobilized on a solid substrate is provided by the invention. Any of a variety of solid supports can be used, which may be made from glass (e.g., glass slides), plastic (e.g., polypropylene, nylon), polyacrylamide, nitrocellulose, or other materials. One method for attaching the nucleic acids to a surface is by printing on glass plates, as is described generally by Schena et al., 1995, *Science* 270:467-470; Shalon et al., 1996, *Genome Res*. 6:639-645. Another method for making microarrays is by making high-density oligonucleotide arrays. See, Fodor et al., 1991, *Science* 251:767-73;

Lockhart et al., 1996, *Nature Biotech* 14:1675; and U.S. Pat. Nos. 5,578,832; 5,556,752; and 5,510,270.

Although arrays are known that include probes for glucose transporters (e.g., an array comprising probes for a substantial fraction of a genome) the devices of the present invention are directed to measuring glucose transporters. Thus, in embodiments, at least about 10%, and sometimes at least about 25%, at least about 50% or at least about 75% of the immobilized probes on a device or array specifically bind (e.g., hybridize to) glucose transport gene products. In one embodiment, the substrate comprises fewer than about 100 distinct probes, fewer than about 50 distinct probes, fewer than about 10 distinct probes, fewer than about 5 distinct probes or fewer than about 3 distinct probes. As used in this context, a probe is "distinct" from a second probe if the two probes do not specifically bind the same polypeptide or polynucleotide (i.e., such as cDNA probes for different genes).

In one embodiment, the probes are selected from monoclonal antibodies or other specific binding proteins (e.g., antibody derivatives or fragments) that specifically bind a glucose transporter protein or a cell expressing such a protein. Probes for polypeptides can also be immobilized in an array format, for example, in an ELISA format in multi-well plates.

8. EXAMPLES

The present invention has been described in detail in the preceding sections. Aspects of the invention are illustrated in the following examples. In each case, the level of glucose transporter level determined in the cancer sample is compared to a reference value to determine whether the tumor is susceptible to treatment with an anti-neoplastic agent comprising a glucose moiety.

Example 1

Western Assay for GLUT2 Levels in a Pancreatic Tumor

This example describes an antibody-based glucose transporter assay for determining the level of GLUT2 in a sample from a pancreatic cancer patient.

Human pancreatic islet cell cancer or carcinoid tumor cancer tissue is obtained from a patient undergoing surgery for treatment of cancer of the pancreas. In the operating room, the excised tissue is placed in a container, clearly marked and transported to the pathology department. After pathological evaluation to assess tumor pathological characteristics and to ensure that the sample contains tumor cells, a portion of the tumor is placed in a well-marked container and transported to the laboratory on dry ice, where it is stored at −70 degrees C. until used. In some instances, a needle aspirate biopsy is used to assess tumor presence and characteristics. All steps below apply to either type of sample.

The frozen sample is weighed and pulverized in a thermovac tissue pulverizer on dry ice, and the tissue powder is placed in a clean tube. The tissue powder is homogenized in buffer (50 mM Tris-HCl-sodium ethylene diamie tetraacetic acid (EDTA), 1% TRITON X-100, 10% glycereol, 10 mM sodium molybdate, 10 mM monothioglycerol, 10 ug/ml aprotinin, 10 ug/ml leupeptin, 0.5 mM phenylmethyl sulphonyl fluoride and 10 ug/ml pepstanin), using polytrone with the appropriate probe depending on the size of the tissue sample. The homogenization is carried out at 0-4 degrees C., with 30 second bursts and 1 minute cooling between bursts. The tissue homogenate is centrifuged at 10,000 g for 10 minutes to separate the nuclear fraction and cell debris from the cytosolic/membrane soluble fraction. The resulting pellet is discarded, and the supernatant, which contains mostly cytosolic and membrane-bound proteins, including GLUT2, is removed and stored frozen until testing.

Resolving gels (10%) are made by mixing 20 ml of acrylamide-bis (30%-0.8% wt/vol), 7.5 ml of 3 M Tris-HCl, pH 8.8, 31.56 ml of ddH$_2$O, and 0.6 ml of 10% SDS; the resulting mixture is degassed for 30 minutes. TEMED (35 ul) is added, and the mixture is again degassed for 30 minutes. Ammonium persulfate (APS) (0.33 ml of 10%) is added, and the mixture is immediately poured into a gel apparatus using 60 cc syringes. 1-Butanol (1 ml) is overlaid on top of the resolving gel to prevent drying, and the gel is allowed to polymerize for 1 hour. The layer of butanol is removed by washing with water, just prior to pouring the stacking gel (see below).

The stacking gel consists of 3.75 ml of acrylamide-bis (30%-8% wt/vol), 1.875 ml of 2M Tris-HCl, pH 6.8, 24 ml of ddH$_2$O, and 0.3 ml of 10% SDS; this gel mixture is prepared and degassed for 30 minutes. TEMED (25:1) is added to the mixture, and the mixture is again degassed for 30 minutes. Ammonium persulphate (0.3 ml; 10%) is added, and the stacking gel is poured into the gel apparatus and the combs placed appropriately. The stacking gel is allowed to polymerize for one hour. The combs are removed, and electrode buffer (25 mM Tris, 192 mM glycine, 4 mM sodium dodecylsulfate, pH 8.3) is added to the gel holder. Protein samples to be resolved are mixed with 5× sample buffer (2 g SDS, 1.0 ml of TRITON X100, 3.126 ml of 2M Tris-HCl, 10.8 ml of ddH$_2$O; adjusted to a final volume of 20 ml and pH 6.8, 100 mg of bromophenol blue, 1.0 ml of mercaptoethanol, and 4 ml of glycerol) to give a final concentration of 1× and are layered into the wells in the gel. Molecular weight (MW) markers (BIORAD) can be included in the gel (10 ul of MW markers to 0.150 ml of 1× sample buffer). The samples are layered onto the gel and electrophoresed for 12-17 hours at 17 mA and 500V at room temperature.

The gels are removed from the apparatus and placed in a BIORAD trans-blot apparatus, which is filled with transfer buffer (20% methanol, 192 mM glycine and 20 mM Tris, pH 8.3). The proteins in the gels are transferred to nitrocellulose membrane for three hours at 0-4 degrees C., with stirring, at 0.36 A and 100V. Nitrocellulose membranes are either placed between two filter papers and stored at room temperature or used immediately in the Western blot analysis.

Nonspecific protein binding sites on the nitrocellulose membranes are blocked by incubation in buffer TBST/5% fat-free milk (10 mM Tris, 150 mM sodium chloride adjusted to pH 8.0; then 0.5% Tween 20 is added) for 1 hour on a shaker at room temperature. Subsequently, the membranes are washed with TBST, and the primary anti-GLUT2 antibodies in the desired dilutions, 1:1000 or 1:2000 in TBST/5% milk) are added. The antibody-antigen interaction is carried out with gentle shaking at room temperature for 1 hour. The membranes are then washed 3 times with TBST for 5 minutes each time to remove unbound primary antibodies.

Secondary antibodies (immuno pure goat anti-rabbit IgG conjugated to peroxidase) are added to the nitrocellulose membrane (1:50,000 in TBST/milk). This incubation is carried out at room temperature for 40 minutes with gentle shaking. The membranes are then washed 4 times for 5 minutes each, with TBST. The membranes are then incubated in one part stable peroxide solution to one part of luminol/enhancer solution for 3-5 minutes (Pierce), as suggested by the manufacturer. The membranes are wrapped in Saran wrap and placed in a cassette. In a dark room, X-ray film is placed on the membrane for 1-30 seconds. The film is developed, and the bands are visualized and quantitation is performed. The level of GLUT2 protein in the sample is normalized to units per weight tumor and compared to a reference value to determine whether the tumor is susceptible to treatment with an anti-neoplastic agent comprising a glucose moiety.

Example 2

Immunohistochemical Assays for GLUT2 Protein Level in Pancreatic Cancer

In the illustrative method described below, the following buffers and solutions are employed: Phosphate Buffered Saline (PBS): 5 mM $Na_2PO_4$, 0.9 mM $KH_2PO_4$, 72 mM NaCl, 1.6 mM KCl, pH 7.4; PBS/TRITON X 100: PBS with TRITON X 100 at a 1:500 dilution; and Citrate Buffer: 18 ml of 0.1M citric acid and 82 ml of 0.1M sodium citrate.

Pancreatic cancer tissue samples are obtained as described in Example 1. Five-micron sections are cut and mounted onto silane-coated slides. The slides are allowed to dry overnight. Slides are heated at 65 degrees C. for 45 minutes to 1 hour, and then deparaffinized and rehydrated in xylene three times for 5 minutes each, 100% ethanol two times for 3 minutes each, and 95% ethanol two times for two minutes each. Endogenous peroxidases are blocked by incubating slides in 45 ml of methanol and 5 ml of 30% hydrogen peroxide for 20 minutes. Slides are rinsed with PBS/TRITON X-100 two times for two minutes each.

Antigen retrieval is performed by adding Citrate Buffer to the glass holder in which the slides are submerged and heating in the microwave for 15 minutes on high; then 5 minutes on 50% power; and then another 5 minutes at 50% power. Slides are then cooled to room temperature for approximately 30 minutes and are then rinsed in PBS/TRITON X-100 two times for two minutes each. Primary GLUT2 antibody is added at the appropriate dilution to each slide (diluted in PBS, 200 ul on each slide) and incubated for 1 hour at 37 C in a humidity chamber. The slides are washed two times for two minutes each with PBS 5% TRITON X-100. Biotinylated secondary antibody is applied to the slide for 30 minutes at room temperature. Slides are washed in PBS 5% TRITON X-100.

Streptavidin is then applied for 30 minutes at room temperature in a humidity chamber, and slides are then rinsed in PBS 5% TRITON X-100. Chromogen is added (2.5 ml PBS, ¼ tablet 3,3' diaminobenzidine tetrahydrochloride (DAB) and two drops of 0.8% hydrogen peroxide), and the slides are incubated for 10 minutes at room temperature in a humidity chamber. The slides are then rinsed in $ddH_2O$ for five minutes, counterstained in Gill's Hematoxylin for 1 minute, and washed in running water until clear. The cytoplasm is cleared with 0.25% acid alcohol (three dips). The slides are then washed under a gentle stream of running water and differentiated in 1% ammonia water for 10 seconds, followed by a wash in running water. The slides are then dehydrated by incubating in 95% ethanol two times for 8-10 dips each; 100% ethanol two times for 8-10 dips each; and xylene three times for 10-15 dips each; coverslips are applied with PERMOUNT for visualization with a light microscope. The slides can be photographed with KODAK ECTOCHROME speed 100 film and the level of staining determined.

Example 3

Immunohistochemical Assay of GLUT1

This example describes an antibody-based, immunohistochemical glucose transporter assay useful in determining the level of GLUT1 protein in a tumor specimen.

Tissue specimens are isolated by surgical resection or tumor biopsy using routine procedures in the course of treatment of cancer patients. Immediately upon isolation, the tissue specimens are placed in a clearly marked container and transported to the pathology department. After pathological evaluation to assess tumor pathological characteristics and to ensure that the sample contains tumor cells, a portion of the tissue specimen is placed in a well-marked container on dry ice and transported to the laboratory.

Specimens are immediately immersed in 10% formalin solution and processed according to the standard method as paraffin-embedded tissue blocks. At least three serial sections, each of four micron thickness, are cut from the paraffin-embedded fixed tissue blocks using a cryostat and mounted onto VECTABOND coated slides (Vector Laboratories, Burlingame, Calif.). The slides are allowed to dry overnight before they are heated at 56° C. for 30 minutes, and are then deparaffinized and rehydrated in xylene three times for 5 minutes each, 100% ethanol two times for 3 minutes each, and 95% ethanol two times for two minutes each.

Endogenous peroxidases are blocked by incubating slides in 0.3% hydrogen peroxide in methanol for 20 minutes. Slides are rinsed with PBS (5 mM $Na_2PO_4$, 0.9 mM $KH_2PO_4$, 72 mM NaCl, 1.6 mM KCl, pH 7.4) two times for two minutes each.

Antigen retrieval is performed by microwaving the slides in 10 mM citrate buffer, pH 6.0, for three cycles of 5 minutes. Slides are subsequently cooled to RT (22° C.) for approximately 30 minutes and are then rinsed in PBS two times for two minutes each. To block non-specific protein binding, the slides are immersed 2% normal goat serum in 1% BSA in PBS for 30 minutes at RT.

Primary anti-human GLUT1 antibody (Chemicon International, Inc., Temecula, Calif.) is added at 1:300 dilution to each slide (diluted in 0.1% BSA in PBS, 200 ul on each slide) and incubated for two hours at RT in a humidity chamber. The anti-GLUT1 antibody is an affinity-purified rabbit polyclonal antibody generated against a 15-amino acid synthetic peptide corresponding to the exofacial loop of the human GLUT-1 sequence.

For negative controls, non-tumor tissues are also isolated from healthy portions of the affected organ or healthy organs of the same patient. In addition, negative controls can include staining without the primary antibody, substitution of anti-glucose transporter antibody by non-immune rabbit IgG (20 ug/ml), and staining with primary antibodies pre-absorbed with the target antigen peptide. A positive control for the assay is staining observed in the vascular tissues and erythrocytes that are present in the tissue sections.

After incubation with primary antibody, the slides are washed two times for two minutes each with PBS. A standard peroxidase-labelled streptavidin-biotin detection method can be used to detect the primary antibody. Biotinylated secondary antibody is applied to the slide for 30 minutes at RT. Slides are washed in PBS. Streptavidin is then applied for 30 minutes at RT in a humidity chamber, and slides are then rinsed in PBS. Chromogen (2.5 ml PBS, ¼ tablet 3,3' diaminobenzidine tetrahydrochloride (DAB) and two drops of 0.8% hydrogen peroxide) is added, and the slides are incubated for 10 minutes at RT in a humidity chamber.

The slides are then rinsed in $ddH_2O$ for five minutes, counterstained in Gill's Hematoxylin for 1 minute, and washed in running water until clear. The cytoplasm is cleared with 0.25% acid alcohol (three dips). The slides are then washed under a gentle stream of running water and differentiated in 1% ammonia water for 10 seconds, followed by a wash in running water.

The slides are dehydrated by incubating in 95% ethanol two times for 8-10 dips each; 100% ethanol two times for 8-10 dips each; and xylene three times for 10-15 dips each; coverslips are applied with PERMOUNT for visualization with a light microscope. The slides can be photographed with KODAK ECTOCHROME speed 100 film.

A semi-quantitative estimate of the proportion of cells with membrane staining and intensity of staining is recorded. The proportional area occupied by immunoreactive protein can be calculated by using a computer-assisted image analysis system KS-300 (ZEISS) connected to a BX60 microscope (OLYMPUS) and a KY-F55B (JVC) color videocamera. Staining results are scored from 0 to 4 according to the intensity and positive rate of staining. Experiments are done in duplicate and average values are calculated.

Depending on the source of tissue specimen and reagents, this assay method will require titration of optimal parameters. Parameters to adjust include, but are not limited to, adhesion of tissue sections on slides, dilution of primary antibody, time and temperature of incubation with primary antibody, and stringency of washes after incubation with the primary antibody.

Example 4

Assay of GLUT8 mRNA Level

This example describes a glucose transporter assay useful in determining the level of GLUT8 mRNA in a tumor specimen.

Tissue specimens are isolated by surgical resection or tumor biopsy using routine procedures in the course of treatment of cancer patients. Immediately upon isolation, the tissue specimens are placed in a clearly marked container and transported to the pathology department. After pathological evaluation to assess tumor pathological characteristics and to ensure that the sample contains tumor cells, a portion of the tissue specimen is placed in a well-marked container and transported to the laboratory on dry ice.

Tissues specimens are homogenized in 4 M guanidine thiocyanate. Poly(A) RNAs are isolated using the DYNABEADS mRNA purification kit (Dynal Biotech) according to the manufacturer's recommendations.

1-5 ug of poly(A) RNA are separated by denaturing gel electrophoresis on 1% agarose gels containing 1% formaldehyde. The resolved RNA is blotted onto nylon membranes (HYBOND N$^+$, Amersham Pharmacia Biotech, Braunschweig, Germany) by capillary action.

The GLUT8 cDNA is radioactively labeled with the Klenow fragment of DNA polymerase I and [$\alpha$-$^{32}$P]dCTP by random oligonucleotide priming. The nylon membranes are hybridized at 42° C. in EXPRESSHYB hybridization solution (Clontech Laboratories, Palo Alto, Calif.).

The membrane is subsequently washed two times at 55° C. with 0.12 M NaCl, 0.012 M sodium citrate, 0.1% SDS before they are dried and exposed overnight on a phosphoimager plate (FUGI Photo Film). Experiments are done in duplicate and average values are calculated.

Example 5

Immunohistochemical Assays for GLUT12 Protein Levels

This example describes an antibody-based, immunohistochemical glucose transporter assay useful in determining the level of GLUT12 protein in a tumor specimen.

Tumor tissue samples are obtained and processed as described in Example 2 prior to the step of antibody binding. Slides are then incubated overnight at 4° C. in a 1:150 or 1:300 dilution of primary (R1396) anti-GLUT12 antibody diluted in 5% FBS/PBS (200 ul on each slide) in a humidity chamber. The rabbit polyclonal anti-GLUT12 antibody, R1396, was raised to the unique 16 C-terminal amino acids of human GLUT12 (Rogers et al., 2002, "Identification of a novel glucose transporter-like protein-GLUT-12" *Am. J. Physiol. Endocrinol. Metab.* 282:E733-E738].

After incubation with primary antibody, the slides are washed with 0.1% Tween-20 in PBS and then incubated for 1 h with biotinylated swine anti-rabbit IgG (Dako, Carpinteria, USA). A standard peroxidase-labelled streptavidin-biotin detection method can be used to detect the primary antibody. Biotinylated secondary antibody is applied to the slide for 30 minutes at RT. Slides are washed in PBS. Streptavidin is then applied for 30 minutes at RT in a humidity chamber, and slides are then rinsed in PBS. Chromogen is added (2.5 ml PBS, ¼ tablet 3,3' diaminobenzidine tetrahydrochloride (DAB) (Sigma, St. Louis, USA) and two drops of 0.8% hydrogen peroxide), and the slides are incubated for 10 minutes at RT in a humidity chamber.

The slides are then rinsed in ddH$_2$O for five minutes, counterstained in Gill's Hematoxylin for 1 minute, and washed in running water until clear. The cytoplasm is cleared with 0.25% acid alcohol (three dips). The slides are then washed under a gentle stream of running water and differentiated in 1% ammonia water for 10 seconds, followed by a wash in running water.

The slides are dehydrated by incubating in 95% ethanol two times for 8-10 dips each; 100% ethanol two times for 8-10 dips each; and xylene three times for 10-15 dips each; coverslips are applied with PERMOUNT for visualization with a light microscope. The slides can be photographed with KODAK ECTOCHROME speed 100 film.

A semi-quantitative estimate of the proportion of cells with membrane staining and intensity of staining is recorded. The criteria for assessing staining are based on those described by Southby et al. The proportional area occupied by immunoreactive protein can be calculated by using a computer-assisted image analysis system KS-300 (ZEISS) connected to a BX60 microscope (OLYMPUS) and a KY-F55B (JVC) color videocamera. Staining results are scored from 0 to 4 according to the intensity and positive rate of staining.

Example 6

FDG-PET Scan

Positron emission tomography (PET) with 18-F-fluorodeoxyglucose (FDG) are used as described in Manda et al., *Anti-cancer Res.* (2003) 23(4):3263-72 to determine the level of glucose transport in patients with thoracic esophageal SCC. The study is performed on patients who underwent pre-operative FDG-PET imaging. FDG-PET studies are performed using a SET 2400 W PET scanner (Schimazu Corporation, Kyoto, Japan) with a 59.5-cm transaxial field of view and a 20-cm axial field of view, which produces 63 image planes, spaced 3.125 mm apart. Transaxial and coronal FDG PET images are interpreted visually by nuclear physicians in conjunction with CT or MRI. Regions of interest are used to evaluate the FDG uptake in segments, with a 4×4 pixel square, including the area of highest activity but not covering the entire tumor.

Example 7

Immunohistochemical Assay

The following assay may be used to assay for glucose transporter expression. Sections of 3- to 4 mm thickness of the primary tumors are cut, deparaffinized in xylene, and rehydrated in descending grades (100-70%) of ethanol. Endogenous peroxidase activity is blocked with 3% hydrogen peroxide in methanol. After several washes in distilled water and phosphate-buffered saline, the sections are incubated with a 1:10 dilution of normal horse serum to minimize background staining. This is followed by incubation for 1 hr at room temperature with the primary antibody (Chemicon GLUT1 antibody). The peroxidase staining procedure utilizes ABC ELITE KITS (Vector Laboratories, Burlingame, Calif.). The immunostaining reactions are visualized using 3-amino-9-ethylcarbazole as the chromogen. The sections and/or cytospin preparations are stained with toluidine blue and mounted in PERMOUNT. Positive and negative control immunostains are also prepared.

The sections are reviewed by the pathologist. Two features of the immunoreaction will be recorded using a semi quantitative scale: the relative number of positive cells (0%, <10%, 10-50%, and >50%) and the intensity of the reaction (0-3). The pattern of immunostaining (membranous, cytoplasmic) is recorded separately. A tumor is considered to over-express glucose transporter if any neoplastic cells show cell membrane reactivity.

The quantitative measurement of glucose transporter immunostaining will be performed using computerized image analysis with the SAMBA 4000 Cell Image Analysis System (Image Products International, Inc., Chantilly, Va.) integrated with a WINDOWS based software. A strong staining tumor tissue section will be used as positive control. The primary antibody will be replaced by an isotype-matched irrelevant antibody to set the negative control threshold, averaging the results from ten fields.

Example 8

Activity-Based Glucose Transporter Assay for Cytochalasin B-Sensitive Glucose Transporters This example describes an activity-based glucose transporter assay useful in determining the level and activity of cytochalasin B-sensitive glucose transporters in a tumor specimen.

Tissue specimens are isolated by surgical resection or tumor biopsy according to routine procedures in the course of treatment of cancer patients. Immediately upon isolation, the tissue specimens are placed in a clearly marked container and transported to the pathology department. After pathological evaluation to assess tumor pathological characteristics and to ensure that the sample contains tumor cells, a portion of the tissue specimen is placed in a well-marked container and transported to the laboratory on ice.

A tumor cell suspension is obtained by adding enzymes to a final concentration of 0.02% DNase, 0.3% collagenase, and 0.4% hyaluronidase, and incubated for 2 hours at 37° C. Cells are washed three times in PBS and passed three times through a 25-gauge needle. After centrifugation, cells are resuspended in incubation buffer (15 mM HEPES, 135 mM NaCl, 5 mM KCl, 1.8 mM $CaCl_2$, 0.8 mM $MgCl_2$) and incubated in this medium for 30 minutes at RT. The uptake assay is then performed in 0.5 mL incubation buffer containing 0.5 mmol 2-deoxyglucose and 6 uL of 2-[1,2-$^3$H]deoxy-D-glucose (25-50 Ci/mmol; NEN Life Science Products, Boston, Mass.) at RT for 1 min. Glucose uptake is stopped by washing the cells with 10 mL of ice-cold PBS.

The cells are collected by centrifugation and washed twice with cold PBS. They are then lysed in 0.5 mL lysis buffer (10 mM Tris-HCl, pH 8.0, 0.2% SDS) and the incorporated radioactivity is assayed by liquid scintillation counting.

Experiments are done in duplicate and average values are calculated. 2-deoxyglucose uptake is calculated after subtraction of nonspecific uptake in parallel samples incubated in the presence of 10 μmol/L cytochalasin B, a potent inhibitor of glucose transporters. Results are normalized for cell number determined in parallel samples.

For negative controls, non-tumor tissues are also isolated from healthy organs of the same patient. An optional positive control can be glucose transport observed with tissues known to express high levels of GLUT4, such as human muscular and fat tissues, or cultured COS cells transfected with full-length GLUT4 cDNA.

Example 9

Flow-Cytometry-Based Glucose Transporter Assay for the Level of GLUT3

This example describes an antibody-based, flow-cytometry-based glucose transporter assay useful in determining the level of GLUT3 protein in a tumor specimen.

Tissue specimens are isolated by surgical resection or tumor biopsy. Immediately upon isolation, the tissue specimens are placed in a clearly marked container and transported to the pathology department. After pathological evaluation to assess tumor pathological characteristics and to ensure that the sample contains tumor cells, a portion of the tissue specimen is placed in a well-marked container on dry ice and transported to the laboratory.

Specimens are dispersed into single-cell suspension using collagenase-digestion Ficoll gradient purification method. The cells are washed twice in Dulbecco's phosphate-buffered saline (PBS) (pH 7.6) by sedimentation at 500×g for 30 seconds at room temperature (RT). The cells are then fixed for 15 minutes at RT in 4% paraformaldehyde in phosphate-buffered saline (PBS) buffered to pH 7.2. They are washed three times in PBS and resuspended in PBS with 3% bovine serum albumin (BSA) and divided into 1.5 ml microcentrifuge tubes at a density of approximately $10^5$ cells per tube.

Primary anti-human GLUT3 antibody (Chemicon International, Inc., Temecula, Calif.) is added at 1:60 dilution to each tube and incubated overnight at 4° C. After incubation with primary antibody, the cells are washed twice by centrifugation at 500×g for 30 seconds in PBS. The cell pellets are resuspended in R-phycoerythrin-labeled goat anti-rabbit IgG (Fisher Scientific) and incubated for 1 hour at 4° C. with occasional shaking. After two washes by centrifugations at 500×g for 30 seconds in PBS, the cells are resuspended in 500 μl of PBS.

IgG binding is determined by flow cytometry performed on a FACScan (Becton Dickinson) flow cytometer. Cell populations are gated to exclude dead cells. Depending on the source of tissue specimen and reagents, this assay method will require titration of optimal parameters. Parameters that may be varied include the dilution of primary antibody, the time and temperature of incubation with primary antibody, and stringency of washes after incubation with the primary antibody. The proportion of cells staining positive for each specimen is determined and may be compared with negative control samples. In an embodiment, the flow cytometry results are displayed as cell number vs. staining intensity (e.g., number of transporters) and the distribution for the sample compared to those of a survey population.

Although the present invention has been described in detail with reference to specific embodiments, those of skill in the art will recognize that modifications and improvements are within the scope and spirit of the invention, as set forth in the claims which follow. All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

What is claimed is:

1. A method for determining whether pancreatic islet cell carcinoma in an individual patient is susceptible to treatment with an anti-neoplastic agent transported by a glucose transporter, wherein the anti-neoplastic agent comprises either a glucose moiety or a glucose analog moiety selected from the group consisting of D-(+)-2-deoxy-glucose, D-(+)-2-amino-2-deoxy-glucose, N-acetyl D-(+)-2-amino-2-deoxy-glucose, D-mannose, D-3-amino-3-deoxy-glucose, D-2-amino-2-deoxy-glucose, D-galactose, D-2-deoxy-D-galactose, D-4-amino-4-deoxy-galactose, D-2-amino-2-deoxy-galactose, and fructose, comprising the steps of:
 (a) obtaining a sample of the pancreatic islet cell carcinoma from the patient;
 (b) measuring the level of the glucose transporter in the sample;
 (c) comparing the measured level of the glucose transporter in the sample to the level of the glucose transporter in a sample of non-tumor pancreatic tissue; and
 (d) determining that the pancreatic islet cell carcinoma is susceptible to treatment with the anti-neoplastic agent if the measured level of the glucose transporter in the sample is greater than the level of the glucose transporter in the sample of non-tumor pancreatic tissue.

2. The method of claim 1, wherein the glucose analog moiety is fructose.

3. The method of claim 1, wherein the glucose transporter is a Class I GLUT comprising an amino acid sequence selected from the group consisting of SEQ ID NO:1, SEQ ID NO:2, SEQ ID NO:3, SEQ ID NO:4, SEQ ID NO:13, and SEQ ID NO:14.

4. The method of claim 1, wherein the glucose transporter is a Class II GLUT comprising an amino acid sequence selected from the group consisting of SEQ ID NO:5, SEQ ID NO:8, and SEQ ID NO:10.

5. The method of claim 1, wherein the glucose transporter is a Class III GLUT comprising an amino acid sequence selected from the group consisting of SEQ ID NO:6, SEQ ID NO:7, SEQ ID NO:9, SEQ ID NO:11, and SEQ ID NO:12.

6. The method of claim 1, further comprising measuring the level of at least one additional glucose transporter in the sample.

7. The method of claim 6 wherein the levels of at least one Class I GLUT comprising an amino acid sequence selected from the group consisting of SEQ ID NO:1, SEQ ID NO:2, SEQ ID NO:3, SEQ ID NO:4, SEQ ID NO:13, and SEQ ID NO:14, at least one Class II GLUT comprising an amino acid sequence selected from the group consisting of SEQ ID NO:5, SEQ ID NO:8, and SEQ ID NO:10, and at least one Class III GLUT comprising an amino acid sequence selected from the group consisting of SEQ ID NO:6, SEQ ID NO:7, SEQ ID NO:9, SEQ ID NO:11, and SEQ ID NO:12 are measured.

8. The method of claim 1, wherein the anti-neoplastic agent is streptozotocin.

9. The method of claim 8 wherein the glucose transporter is a polypeptide comprising the amino acid sequence of SEQ ID NO:2.

10. The method of claim 1, wherein the anti-neoplastic agent is glufosfamide.

11. The method of claim 10, wherein the glucose transporter is a Na+-dependent glucose transporter.

12. The method of claim 1, wherein the anti-neoplastic agent is a glyco-S-nitrosothiol.

13. The method of claim 12, wherein the glucose transporter is a polypeptide comprising the amino acid sequence of SEQ ID NO:1.

14. The method of claim 1, wherein the level of glucose transporter in the sample is measured by an immunological assay.

15. The method of claim 1, wherein the level of glucose transporter in the sample is measured by an amplification of an RNA or cDNA.

16. The method of claim 1 wherein the glucose transporter is a polypeptide comprising the amino acid sequence of SEQ ID NO:2, and the anti-neoplastic agent is streptozotocin, glufosfamide, or a gluSNAP compound.

17. The method of claim 1, wherein the non-tumor pancreatic tissue sample is non-tumor pancreatic tissue derived from the patient.

* * * * *

SEQUENCE LISTING

<160> NUMBER OF SEQ ID NOS: 100

<210> SEQ ID NO 1
<211> LENGTH: 492
<212> TYPE: PRT
<213> ORGANISM: Homo sapiens

<400> SEQUENCE: 1

```
Met Glu Pro Ser Ser Lys Lys Leu Thr Gly Arg Leu Met Leu Ala Val
1               5                   10                  15

Gly Gly Ala Val Leu Gly Ser Leu Gln Phe Gly Tyr Asn Thr Gly Val
            20                  25                  30

Ile Asn Ala Pro Gln Lys Val Ile Glu Glu Phe Tyr Asn Gln Thr Trp
        35                  40                  45

Val His Arg Tyr Gly Glu Ser Ile Leu Pro Thr Thr Leu Thr Thr Leu
    50                  55                  60

Trp Ser Leu Ser Val Ala Ile Phe Ser Val Gly Gly Met Ile Gly Ser
65                  70                  75                  80

Phe Ser Val Gly Leu Phe Val Asn Arg Phe Gly Arg Arg Asn Ser Met
                85                  90                  95

Leu Met Met Asn Leu Leu Ala Phe Val Ser Ala Val Leu Met Gly Phe
            100                 105                 110

Ser Lys Leu Gly Lys Ser Phe Glu Met Leu Ile Leu Gly Arg Phe Ile
        115                 120                 125

Ile Gly Val Tyr Cys Gly Leu Thr Thr Gly Phe Val Pro Met Tyr Val
    130                 135                 140

Gly Glu Val Ser Pro Thr Ala Phe Arg Gly Ala Leu Gly Thr Leu His
145                 150                 155                 160

Gln Leu Gly Ile Val Gly Ile Leu Ile Ala Gln Val Phe Gly Leu
                165                 170                 175

Asp Ser Ile Met Gly Asn Lys Asp Leu Trp Pro Leu Leu Ser Ile
            180                 185                 190

Ile Phe Ile Pro Ala Leu Leu Gln Cys Ile Val Leu Pro Phe Cys Pro
        195                 200                 205

Glu Ser Pro Arg Phe Leu Leu Ile Asn Arg Asn Glu Glu Asn Arg Ala
    210                 215                 220

Lys Ser Val Leu Lys Lys Leu Arg Gly Thr Ala Asp Val Thr His Asp
225                 230                 235                 240

Leu Gln Glu Met Lys Glu Glu Ser Arg Gln Met Met Arg Glu Lys Lys
                245                 250                 255

Val Thr Ile Leu Glu Leu Phe Arg Ser Pro Ala Tyr Arg Gln Pro Ile
            260                 265                 270

Leu Ile Ala Val Val Leu Gln Leu Ser Gln Gln Leu Ser Gly Ile Asn
        275                 280                 285

Ala Val Phe Tyr Tyr Ser Thr Ser Ile Phe Glu Lys Ala Gly Val Gln
    290                 295                 300

Gln Pro Val Tyr Ala Thr Ile Gly Ser Gly Ile Val Asn Thr Ala Phe
305                 310                 315                 320
```

-continued

```
Thr Val Val Ser Leu Phe Val Val Glu Arg Ala Gly Arg Arg Thr Leu
                325                 330                 335

His Leu Ile Gly Leu Ala Gly Met Ala Gly Cys Ala Ile Leu Met Thr
                340                 345                 350

Ile Ala Leu Ala Leu Leu Glu Gln Leu Pro Trp Met Ser Tyr Leu Ser
                355                 360                 365

Ile Val Ala Ile Phe Gly Phe Val Ala Phe Phe Glu Val Gly Pro Gly
                370                 375                 380

Pro Ile Pro Trp Phe Ile Val Ala Glu Leu Phe Ser Gln Gly Pro Arg
385                 390                 395                 400

Pro Ala Ala Ile Ala Val Ala Gly Phe Ser Asn Trp Thr Ser Asn Phe
                405                 410                 415

Ile Val Gly Met Cys Phe Gln Tyr Val Glu Gln Leu Cys Gly Pro Tyr
                420                 425                 430

Val Phe Ile Ile Phe Thr Val Leu Leu Val Leu Phe Phe Ile Phe Thr
                435                 440                 445

Tyr Phe Lys Val Pro Glu Thr Lys Gly Arg Thr Phe Asp Glu Ile Ala
                450                 455                 460

Ser Gly Phe Arg Gln Gly Gly Ala Ser Gln Ser Asp Lys Thr Pro Glu
465                 470                 475                 480

Glu Leu Phe His Pro Leu Gly Ala Asp Ser Gln Val
                485                 490

<210> SEQ ID NO 2
<211> LENGTH: 524
<212> TYPE: PRT
<213> ORGANISM: Homo sapiens

<400> SEQUENCE: 2

Met Thr Glu Asp Lys Val Thr Gly Thr Leu Val Phe Thr Val Ile Thr
1               5                   10                  15

Ala Val Leu Gly Ser Phe Gln Phe Gly Tyr Asp Ile Gly Val Ile Asn
                20                  25                  30

Ala Pro Gln Gln Val Ile Ile Ser His Tyr Arg His Val Leu Gly Val
                35                  40                  45

Pro Leu Asp Asp Arg Lys Ala Ile Asn Asn Tyr Val Ile Asn Ser Thr
50                  55                  60

Asp Glu Leu Pro Thr Ile Ser Tyr Ser Met Asn Pro Lys Pro Thr Pro
65                  70                  75                  80

Trp Ala Glu Glu Glu Thr Val Ala Ala Ala Gln Leu Ile Thr Met Leu
                85                  90                  95

Trp Ser Leu Ser Val Ser Ser Phe Ala Val Gly Gly Met Thr Ala Ser
                100                 105                 110

Phe Phe Gly Gly Trp Leu Gly Asp Thr Leu Gly Arg Ile Lys Ala Met
                115                 120                 125

Leu Val Ala Asn Ile Leu Ser Leu Val Gly Ala Leu Leu Met Gly Phe
                130                 135                 140

Ser Lys Leu Gly Pro Ser His Ile Leu Ile Ile Ala Gly Arg Ser Ile
145                 150                 155                 160

Ser Gly Leu Tyr Cys Gly Leu Ile Ser Gly Leu Val Pro Met Tyr Ile
                165                 170                 175

Gly Glu Ile Ala Pro Thr Ala Leu Arg Gly Ala Leu Gly Thr Phe His
                180                 185                 190

Gln Leu Ala Ile Val Thr Gly Ile Leu Ile Ser Gln Ile Ile Gly Leu
                195                 200                 205
```

Glu Phe Ile Leu Gly Asn Tyr Asp Leu Trp His Ile Leu Leu Gly Leu
    210                 215                 220

Ser Gly Val Arg Ala Ile Leu Gln Ser Leu Leu Leu Phe Phe Cys Pro
225                 230                 235                 240

Glu Ser Pro Arg Tyr Leu Tyr Ile Lys Leu Asp Glu Glu Val Lys Ala
                245                 250                 255

Lys Gln Ser Leu Lys Arg Leu Arg Gly Tyr Asp Asp Val Thr Lys Asp
            260                 265                 270

Ile Asn Glu Met Arg Lys Glu Arg Glu Ala Ser Ser Glu Gln Lys
        275                 280                 285

Val Ser Ile Ile Gln Leu Phe Thr Asn Ser Ser Tyr Arg Gln Pro Ile
    290                 295                 300

Leu Val Ala Leu Met Leu His Val Ala Gln Gln Phe Ser Gly Ile Asn
305                 310                 315                 320

Gly Ile Phe Tyr Tyr Ser Thr Ser Ile Phe Gln Thr Ala Gly Ile Ser
                325                 330                 335

Lys Pro Val Tyr Ala Thr Ile Gly Val Gly Ala Val Asn Met Val Phe
            340                 345                 350

Thr Ala Val Ser Val Phe Leu Val Glu Lys Ala Gly Arg Arg Ser Leu
        355                 360                 365

Phe Leu Ile Gly Met Ser Gly Met Phe Val Cys Ala Ile Phe Met Ser
    370                 375                 380

Val Gly Leu Val Leu Leu Asn Lys Phe Ser Trp Met Ser Tyr Val Ser
385                 390                 395                 400

Met Ile Ala Ile Phe Leu Phe Val Ser Phe Phe Glu Ile Gly Pro Gly
                405                 410                 415

Pro Ile Pro Trp Phe Met Val Ala Glu Phe Phe Ser Gln Gly Pro Arg
            420                 425                 430

Pro Ala Ala Leu Ala Ile Ala Ala Phe Ser Asn Trp Thr Cys Asn Phe
        435                 440                 445

Ile Val Ala Leu Cys Phe Gln Tyr Ile Ala Asp Phe Cys Gly Pro Tyr
    450                 455                 460

Val Phe Phe Leu Phe Ala Gly Val Leu Leu Ala Phe Thr Leu Phe Thr
465                 470                 475                 480

Phe Phe Lys Val Pro Glu Thr Lys Gly Lys Ser Phe Glu Glu Ile Ala
                485                 490                 495

Ala Glu Phe Gln Lys Lys Ser Gly Ser Ala His Arg Pro Lys Ala Ala
            500                 505                 510

Val Glu Met Lys Phe Leu Gly Ala Thr Glu Thr Val
        515                 520

<210> SEQ ID NO 3
<211> LENGTH: 496
<212> TYPE: PRT
<213> ORGANISM: Homo sapiens

<400> SEQUENCE: 3

Met Gly Thr Gln Lys Val Thr Pro Ala Leu Ile Phe Ala Ile Thr Val
1               5                   10                  15

Ala Thr Ile Gly Ser Phe Gln Phe Gly Tyr Asn Thr Gly Val Ile Asn
            20                  25                  30

Ala Pro Glu Lys Ile Ile Lys Glu Phe Ile Asn Lys Thr Leu Thr Asp
        35                  40                  45

Lys Gly Asn Ala Pro Pro Ser Glu Val Leu Leu Thr Ser Leu Trp Ser

-continued

```
                50                  55                  60
Leu Ser Val Ala Ile Phe Ser Val Gly Gly Met Ile Gly Ser Phe Ser
 65                  70                  75                  80

Val Gly Leu Phe Val Asn Arg Phe Gly Arg Arg Asn Ser Met Leu Ile
                     85                  90                  95

Val Asn Leu Leu Ala Val Thr Gly Gly Cys Phe Met Gly Leu Cys Lys
                100                 105                 110

Val Ala Lys Ser Val Glu Met Leu Ile Leu Gly Arg Leu Val Ile Gly
                115                 120                 125

Leu Phe Cys Gly Leu Cys Thr Gly Phe Val Pro Met Tyr Ile Gly Glu
                130                 135                 140

Ile Ser Pro Thr Ala Leu Arg Gly Ala Phe Gly Thr Leu Asn Gln Leu
145                 150                 155                 160

Gly Ile Val Val Gly Ile Leu Val Ala Gln Ile Phe Gly Leu Glu Phe
                165                 170                 175

Ile Leu Gly Ser Glu Glu Leu Trp Pro Leu Leu Leu Gly Phe Thr Ile
                180                 185                 190

Leu Pro Ala Ile Leu Gln Ser Ala Leu Pro Phe Cys Pro Glu Ser
                195                 200                 205

Pro Arg Phe Leu Leu Ile Asn Arg Lys Glu Glu Asn Ala Lys Gln
210                 215                 220

Ile Leu Gln Arg Leu Trp Gly Thr Gln Asp Val Ser Gln Asp Ile Gln
225                 230                 235                 240

Glu Met Lys Asp Glu Ser Ala Arg Met Ser Gln Glu Lys Gln Val Thr
                245                 250                 255

Val Leu Glu Leu Phe Arg Val Ser Ser Tyr Arg Gln Pro Ile Ile Ile
                260                 265                 270

Ser Ile Val Leu Gln Leu Ser Gln Gln Leu Ser Gly Ile Asn Ala Val
                275                 280                 285

Phe Tyr Tyr Ser Thr Gly Ile Phe Lys Asp Ala Gly Val Gln Glu Pro
                290                 295                 300

Ile Tyr Ala Thr Ile Gly Ala Gly Val Val Asn Thr Ile Phe Thr Val
305                 310                 315                 320

Val Ser Leu Phe Leu Val Glu Arg Ala Gly Arg Arg Thr Leu His Met
                325                 330                 335

Ile Gly Leu Gly Gly Met Ala Phe Cys Ser Thr Leu Met Thr Val Ser
                340                 345                 350

Leu Leu Leu Lys Asp Asn Tyr Asn Gly Met Ser Phe Val Cys Ile Gly
                355                 360                 365

Ala Ile Leu Val Phe Val Ala Phe Phe Glu Ile Gly Pro Gly Pro Ile
                370                 375                 380

Pro Trp Phe Ile Val Ala Glu Leu Phe Ser Gln Gly Pro Arg Pro Ala
385                 390                 395                 400

Ala Met Ala Val Ala Gly Cys Ser Asn Trp Thr Ser Asn Phe Leu Val
                405                 410                 415

Gly Leu Leu Phe Pro Ser Ala Ala His Tyr Leu Gly Ala Tyr Val Phe
                420                 425                 430

Ile Ile Phe Thr Gly Phe Leu Ile Thr Phe Leu Ala Phe Thr Phe Phe
                435                 440                 445

Lys Val Pro Glu Thr Arg Gly Arg Thr Phe Glu Asp Ile Thr Arg Ala
                450                 455                 460

Phe Glu Gly Gln Ala His Gly Ala Asp Arg Ser Gly Lys Asp Gly Val
465                 470                 475                 480
```

Met Glu Met Asn Ser Ile Glu Pro Ala Lys Glu Thr Thr Thr Asn Val
            485                 490                 495

<210> SEQ ID NO 4
<211> LENGTH: 509
<212> TYPE: PRT
<213> ORGANISM: Homo sapiens

<400> SEQUENCE: 4

Met Pro Ser Gly Phe Gln Gln Ile Gly Ser Glu Asp Gly Glu Pro Pro
1               5                   10                  15

Gln Gln Arg Val Thr Gly Thr Leu Val Leu Ala Val Phe Ser Ala Val
                20                  25                  30

Leu Gly Ser Leu Gln Phe Gly Tyr Asn Ile Gly Val Ile Asn Ala Pro
            35                  40                  45

Gln Lys Val Ile Glu Gln Ser Tyr Asn Glu Thr Trp Leu Gly Arg Gln
    50                  55                  60

Gly Pro Glu Gly Pro Ser Ser Ile Pro Pro Gly Thr Leu Thr Thr Leu
65                  70                  75                  80

Trp Ala Leu Ser Val Ala Ile Phe Ser Val Gly Gly Met Ile Ser Ser
                85                  90                  95

Phe Leu Ile Gly Ile Ile Ser Gln Trp Leu Gly Arg Lys Arg Ala Met
            100                 105                 110

Leu Val Asn Asn Val Leu Ala Val Leu Gly Gly Ser Leu Met Gly Leu
        115                 120                 125

Ala Asn Ala Ala Ala Ser Tyr Glu Met Leu Ile Leu Gly Arg Phe Leu
    130                 135                 140

Ile Gly Ala Tyr Ser Gly Leu Thr Ser Gly Leu Val Pro Met Tyr Val
145                 150                 155                 160

Gly Glu Ile Ala Pro Thr His Leu Arg Gly Ala Leu Gly Thr Leu Asn
                165                 170                 175

Gln Leu Ala Ile Val Ile Gly Ile Leu Ile Ala Gln Val Leu Gly Leu
            180                 185                 190

Glu Ser Leu Leu Gly Thr Ala Ser Leu Trp Pro Leu Leu Leu Gly Leu
        195                 200                 205

Thr Val Leu Pro Ala Leu Leu Gln Leu Val Leu Leu Pro Phe Cys Pro
    210                 215                 220

Glu Ser Pro Arg Tyr Leu Tyr Ile Ile Gln Asn Leu Glu Gly Pro Ala
225                 230                 235                 240

Arg Lys Ser Leu Lys Arg Leu Thr Gly Trp Ala Asp Val Ser Gly Val
                245                 250                 255

Leu Ala Glu Leu Lys Asp Glu Lys Arg Lys Leu Glu Arg Glu Arg Pro
            260                 265                 270

Leu Ser Leu Leu Gln Leu Leu Gly Ser Arg Thr His Arg Gln Pro Leu
        275                 280                 285

Ile Ile Ala Val Val Leu Gln Leu Ser Gln Gln Leu Ser Gly Ile Asn
    290                 295                 300

Ala Val Phe Tyr Tyr Ser Thr Ser Ile Phe Glu Thr Ala Gly Val Gly
305                 310                 315                 320

Gln Pro Ala Tyr Ala Thr Ile Gly Ala Gly Val Val Asn Thr Val Phe
                325                 330                 335

Thr Leu Val Ser Val Leu Leu Val Glu Arg Ala Gly Arg Arg Thr Leu
            340                 345                 350

His Leu Leu Gly Leu Ala Gly Met Cys Gly Cys Ala Ile Leu Met Thr

```
                355                 360                 365
Val Ala Leu Leu Leu Glu Arg Val Pro Ala Met Ser Tyr Val Ser
    370                 375                 380

Ile Val Ala Ile Phe Gly Phe Val Ala Phe Glu Ile Gly Pro Gly
385                 390                 395                 400

Pro Ile Pro Trp Phe Ile Val Ala Glu Leu Phe Ser Gln Gly Pro Arg
            405                 410                 415

Pro Ala Ala Met Ala Val Ala Gly Phe Ser Asn Trp Thr Ser Asn Phe
                420                 425                 430

Ile Ile Gly Met Gly Phe Gln Tyr Val Ala Glu Ala Met Gly Pro Tyr
        435                 440                 445

Val Phe Leu Leu Phe Ala Val Leu Leu Leu Gly Phe Phe Ile Phe Thr
    450                 455                 460

Phe Leu Arg Val Pro Glu Thr Arg Gly Arg Thr Phe Asp Gln Ile Ser
465                 470                 475                 480

Ala Ala Phe His Arg Thr Pro Ser Leu Leu Glu Gln Glu Val Lys Pro
                485                 490                 495

Ser Thr Glu Leu Glu Tyr Leu Gly Pro Asp Glu Asn Asp
                500                 505

<210> SEQ ID NO 5
<211> LENGTH: 501
<212> TYPE: PRT
<213> ORGANISM: Homo sapiens

<400> SEQUENCE: 5

Met Glu Gln Gln Asp Gln Ser Met Lys Glu Gly Arg Leu Thr Leu Val
1               5                   10                  15

Leu Ala Leu Ala Thr Leu Ile Ala Ala Phe Gly Ser Ser Phe Gln Tyr
            20                  25                  30

Gly Tyr Asn Val Ala Ala Val Asn Ser Pro Ala Leu Leu Met Gln Gln
        35                  40                  45

Phe Tyr Asn Glu Thr Tyr Tyr Gly Arg Thr Gly Glu Phe Met Glu Asp
    50                  55                  60

Phe Pro Leu Thr Leu Leu Trp Ser Val Thr Val Ser Met Phe Pro Phe
65                  70                  75                  80

Gly Gly Phe Ile Gly Ser Leu Leu Val Gly Pro Leu Val Asn Lys Phe
                85                  90                  95

Gly Arg Lys Gly Ala Leu Leu Phe Asn Asn Ile Phe Ser Ile Val Pro
            100                 105                 110

Ala Ile Leu Met Gly Cys Ser Arg Val Ala Thr Ser Phe Glu Leu Ile
        115                 120                 125

Ile Ile Ser Arg Leu Leu Val Gly Ile Cys Ala Gly Val Ser Ser Asn
    130                 135                 140

Val Val Pro Met Tyr Leu Gly Glu Leu Ala Pro Lys Asn Leu Arg Gly
145                 150                 155                 160

Ala Leu Gly Val Val Pro Gln Leu Phe Ile Thr Val Gly Ile Leu Val
                165                 170                 175

Ala Gln Ile Phe Gly Leu Arg Asn Leu Leu Ala Asn Val Asp Gly Trp
            180                 185                 190

Pro Ile Leu Leu Gly Leu Thr Gly Val Pro Ala Ala Leu Gln Leu Leu
        195                 200                 205

Leu Leu Pro Phe Phe Pro Glu Ser Pro Arg Tyr Leu Leu Ile Gln Lys
    210                 215                 220
```

```
Lys Asp Glu Ala Ala Ala Lys Ala Leu Gln Thr Leu Arg Gly Trp
225                 230                 235                 240

Asp Ser Val Asp Arg Glu Val Ala Glu Ile Arg Gln Glu Asp Glu Ala
            245                 250                 255

Glu Lys Ala Ala Gly Phe Ile Ser Val Leu Lys Leu Phe Arg Met Arg
                260                 265                 270

Ser Leu Arg Trp Gln Leu Leu Ser Ile Ile Val Leu Met Gly Gly Gln
            275                 280                 285

Gln Leu Ser Gly Val Asn Ala Ile Tyr Tyr Tyr Ala Asp Gln Ile Tyr
290                 295                 300

Leu Ser Ala Gly Val Pro Glu Glu His Val Gln Tyr Val Thr Ala Gly
305                 310                 315                 320

Thr Gly Ala Val Asn Val Val Met Thr Phe Cys Ala Val Phe Val Val
                325                 330                 335

Glu Leu Leu Gly Arg Arg Leu Leu Leu Leu Gly Phe Ser Ile Cys
                340                 345                 350

Leu Ile Ala Cys Cys Val Leu Thr Ala Ala Leu Ala Leu Gln Asp Thr
            355                 360                 365

Val Ser Trp Met Pro Tyr Ile Ser Ile Val Cys Val Ile Ser Tyr Val
            370                 375                 380

Ile Gly His Ala Leu Gly Pro Ser Pro Ile Pro Ala Leu Leu Ile Thr
385                 390                 395                 400

Glu Ile Phe Leu Gln Ser Ser Arg Pro Ser Ala Phe Met Val Gly Gly
                405                 410                 415

Ser Val His Trp Leu Ser Asn Phe Thr Val Gly Leu Ile Phe Pro Phe
            420                 425                 430

Ile Gln Glu Gly Leu Gly Pro Tyr Ser Phe Ile Val Phe Ala Val Ile
            435                 440                 445

Cys Leu Leu Thr Thr Ile Tyr Ile Phe Leu Ile Val Pro Glu Thr Lys
450                 455                 460

Ala Lys Thr Phe Ile Glu Ile Asn Gln Ile Phe Thr Lys Met Asn Lys
465                 470                 475                 480

Val Ser Glu Val Tyr Pro Glu Lys Glu Glu Leu Lys Glu Leu Pro Pro
                485                 490                 495

Val Thr Ser Glu Gln
            500

<210> SEQ ID NO 6
<211> LENGTH: 507
<212> TYPE: PRT
<213> ORGANISM: Homo sapiens

<400> SEQUENCE: 6

Met Gln Glu Pro Leu Leu Gly Ala Glu Gly Pro Asp Tyr Asp Thr Phe
1               5                   10                  15

Pro Glu Lys Pro Pro Ser Pro Gly Asp Arg Ala Arg Val Gly Thr
            20                  25                  30

Leu Gln Asn Lys Arg Val Phe Leu Ala Thr Phe Ala Ala Val Leu Gly
            35                  40                  45

Asn Phe Ser Phe Gly Tyr Ala Leu Val Tyr Thr Ser Pro Val Ile Pro
        50                  55                  60

Ala Leu Glu Arg Ser Leu Asp Pro Asp Leu His Leu Thr Lys Ser Gln
65                  70                  75                  80

Ala Ser Trp Phe Gly Ser Val Phe Thr Leu Gly Ala Ala Ala Gly Gly
            85                  90                  95
```

```
Leu Ser Ala Met Ile Leu Asn Asp Leu Leu Gly Arg Lys Leu Ser Ile
                100                 105                 110

Met Phe Ser Ala Val Pro Ser Ala Ala Gly Tyr Ala Leu Met Ala Gly
            115                 120                 125

Ala His Gly Leu Trp Met Leu Leu Gly Arg Thr Leu Thr Gly Phe
        130                 135                 140

Ala Gly Gly Leu Thr Ala Ala Cys Ile Pro Val Tyr Val Ser Glu Ile
145                 150                 155                 160

Ala Pro Pro Gly Val Arg Gly Ala Leu Gly Ala Thr Pro Gln Leu Met
                165                 170                 175

Ala Val Phe Gly Ser Leu Ser Leu Tyr Ala Leu Gly Leu Leu Leu Pro
            180                 185                 190

Trp Arg Trp Leu Ala Val Ala Gly Glu Ala Pro Val Leu Ile Met Ile
        195                 200                 205

Leu Leu Leu Ser Phe Met Pro Asn Ser Pro Arg Phe Leu Leu Ser Arg
    210                 215                 220

Gly Arg Asp Glu Glu Ala Leu Arg Ala Leu Ala Trp Leu Arg Gly Thr
225                 230                 235                 240

Asp Val Asp Val His Trp Glu Phe Glu Gln Ile Gln Asp Asn Val Arg
                245                 250                 255

Arg Gln Ser Ser Arg Val Ser Trp Ala Glu Ala Arg Ala Pro His Val
            260                 265                 270

Cys Arg Pro Ile Thr Val Ala Leu Leu Met Arg Leu Leu Gln Gln Leu
        275                 280                 285

Thr Gly Ile Thr Pro Ile Leu Val Tyr Leu Gln Ser Ile Phe Asp Ser
    290                 295                 300

Thr Ala Val Leu Leu Pro Pro Lys Asp Asp Ala Ala Ile Val Gly Ala
305                 310                 315                 320

Val Arg Leu Leu Ser Val Leu Ile Ala Ala Leu Thr Met Asp Leu Ala
                325                 330                 335

Gly Arg Lys Val Leu Leu Phe Val Ser Ala Ala Ile Met Phe Ala Ala
            340                 345                 350

Asn Leu Thr Leu Gly Leu Tyr Ile His Phe Gly Pro Arg Pro Leu Ser
        355                 360                 365

Pro Asn Ser Thr Ala Gly Leu Glu Ser Glu Ser Trp Gly Asp Leu Ala
    370                 375                 380

Gln Pro Leu Ala Ala Pro Ala Gly Tyr Leu Thr Leu Val Pro Leu Leu
385                 390                 395                 400

Ala Thr Met Leu Phe Ile Met Gly Tyr Ala Val Gly Trp Gly Pro Ile
                405                 410                 415

Thr Trp Leu Leu Met Ser Glu Val Leu Pro Leu Arg Ala Arg Gly Val
            420                 425                 430

Ala Ser Gly Leu Cys Val Leu Ala Ser Trp Leu Thr Ala Phe Val Leu
        435                 440                 445

Thr Lys Ser Phe Leu Pro Val Val Ser Thr Phe Gly Leu Gln Val Pro
    450                 455                 460

Phe Phe Phe Phe Ala Ala Ile Cys Leu Val Ser Leu Val Phe Thr Gly
465                 470                 475                 480

Cys Cys Val Pro Glu Thr Lys Gly Arg Ser Leu Glu Gln Ile Glu Ser
                485                 490                 495

Phe Phe Arg Met Gly Arg Arg Ser Phe Leu Arg
            500                 505
```

<210> SEQ ID NO 7
<211> LENGTH: 477
<212> TYPE: PRT
<213> ORGANISM: Homo sapiens

<400> SEQUENCE: 7

Met Thr Pro Glu Asp Pro Glu Thr Gln Pro Leu Leu Gly Pro Pro
1               5                   10                  15

Gly Gly Ser Ala Pro Arg Gly Arg Val Phe Leu Ala Ala Phe Ala
            20                  25                  30

Ala Ala Leu Gly Pro Leu Ser Phe Gly Phe Ala Leu Gly Tyr Ser Ser
            35                  40                  45

Pro Ala Ile Pro Ser Leu Gln Arg Ala Ala Pro Ala Pro Arg Leu
        50                  55                  60

Asp Asp Ala Ala Ala Ser Trp Phe Gly Ala Val Val Thr Leu Gly Ala
65                  70                  75                  80

Ala Ala Gly Gly Val Leu Gly Gly Trp Leu Val Asp Arg Ala Gly Arg
                85                  90                  95

Lys Leu Ser Leu Leu Cys Ser Val Pro Phe Val Ala Gly Phe Ala
            100                 105                 110

Val Ile Thr Ala Ala Gln Asp Val Trp Met Leu Leu Gly Gly Arg Leu
            115                 120                 125

Leu Thr Gly Leu Ala Cys Gly Val Ala Ser Leu Val Ala Pro Val Tyr
        130                 135                 140

Ile Ser Glu Ile Ala Tyr Pro Ala Val Arg Gly Leu Leu Gly Ser Cys
145                 150                 155                 160

Val Gln Leu Met Val Val Gly Ile Leu Leu Ala Tyr Leu Ala Gly
                165                 170                 175

Trp Val Leu Glu Trp Arg Trp Leu Ala Val Leu Gly Cys Val Pro Pro
            180                 185                 190

Ser Leu Met Leu Leu Met Cys Phe Met Pro Glu Thr Pro Arg Phe
            195                 200                 205

Leu Leu Thr Gln His Arg Arg Gln Glu Ala Met Ala Ala Leu Arg Phe
        210                 215                 220

Leu Trp Gly Ser Glu Gln Gly Trp Glu Asp Pro Pro Ile Gly Ala Glu
225                 230                 235                 240

Gln Ser Phe His Leu Ala Leu Leu Arg Gln Pro Gly Ile Tyr Lys Pro
                245                 250                 255

Phe Ile Ile Gly Val Ser Leu Met Ala Phe Gln Gln Leu Ser Gly Val
            260                 265                 270

Asn Ala Val Met Phe Tyr Ala Glu Thr Ile Phe Glu Glu Ala Lys Phe
            275                 280                 285

Lys Asp Ser Ser Leu Ala Ser Val Val Val Gly Val Ile Gln Val Leu
        290                 295                 300

Phe Thr Ala Val Ala Ala Leu Ile Met Asp Arg Ala Gly Arg Arg Leu
305                 310                 315                 320

Leu Leu Val Leu Ser Gly Val Val Met Val Phe Ser Thr Ser Ala Phe
                325                 330                 335

Gly Ala Tyr Phe Lys Leu Thr Gln Gly Gly Pro Gly Asn Ser Ser His
            340                 345                 350

Val Ala Ile Ser Ala Pro Val Ser Ala Gln Pro Val Asp Ala Ser Val
            355                 360                 365

Gly Leu Ala Trp Leu Ala Val Gly Ser Met Cys Leu Phe Ile Ala Gly
        370                 375                 380

```
Phe Ala Val Gly Trp Gly Pro Ile Pro Trp Leu Leu Met Ser Glu Ile
385                 390                 395                 400

Phe Pro Leu His Val Lys Gly Val Ala Thr Gly Ile Cys Val Leu Thr
            405                 410                 415

Asn Trp Leu Met Ala Phe Leu Val Thr Lys Glu Phe Ser Ser Leu Met
                420                 425                 430

Glu Val Leu Arg Pro Tyr Gly Ala Phe Trp Leu Ala Ser Ala Phe Cys
            435                 440                 445

Ile Phe Ser Val Leu Phe Thr Phe Ser Cys Val Pro Glu Thr Lys Gly
        450                 455                 460

Lys Thr Leu Glu Gln Ile Thr Ala His Phe Glu Gly Arg
465                 470                 475

<210> SEQ ID NO 8
<211> LENGTH: 540
<212> TYPE: PRT
<213> ORGANISM: Homo sapiens

<400> SEQUENCE: 8

Met Ala Arg Lys Gln Asn Arg Asn Ser Lys Glu Leu Gly Leu Val Pro
1               5                   10                  15

Leu Thr Asp Asp Thr Ser His Ala Arg Pro Pro Gly Pro Gly Arg Ala
            20                  25                  30

Leu Leu Glu Cys Asp His Leu Arg Ser Gly Val Pro Gly Gly Arg Arg
        35                  40                  45

Arg Lys Asp Trp Ser Cys Ser Leu Leu Val Ala Ser Leu Ala Gly Ala
    50                  55                  60

Phe Gly Ser Ser Phe Leu Tyr Gly Tyr Asn Leu Ser Val Val Asn Ala
65                  70                  75                  80

Pro Thr Pro Tyr Ile Lys Ala Phe Tyr Asn Glu Ser Trp Glu Arg Arg
                85                  90                  95

His Gly Arg Pro Ile Asp Pro Asp Thr Leu Thr Leu Leu Trp Ser Val
            100                 105                 110

Thr Val Ser Ile Phe Ala Ile Gly Gly Leu Val Gly Thr Leu Ile Val
        115                 120                 125

Lys Met Ile Gly Lys Val Leu Gly Arg Lys His Thr Leu Leu Ala Asn
    130                 135                 140

Asn Gly Phe Ala Ile Ser Ala Ala Leu Leu Met Ala Cys Ser Leu Gln
145                 150                 155                 160

Ala Gly Ala Phe Glu Met Leu Ile Val Gly Arg Phe Ile Met Gly Ile
                165                 170                 175

Asp Gly Gly Val Ala Leu Ser Val Leu Pro Met Tyr Leu Ser Glu Ile
            180                 185                 190

Ser Pro Lys Glu Ile Arg Gly Ser Leu Gly Gln Val Thr Ala Ile Phe
        195                 200                 205

Ile Cys Ile Gly Val Phe Thr Gly Gln Leu Leu Gly Leu Pro Glu Leu
    210                 215                 220

Leu Gly Lys Glu Ser Thr Trp Pro Tyr Leu Phe Gly Val Ile Val Val
225                 230                 235                 240

Pro Ala Val Val Gln Leu Leu Ser Leu Pro Phe Leu Pro Asp Ser Pro
                245                 250                 255

Arg Tyr Leu Leu Leu Glu Lys His Asn Glu Ala Arg Ala Val Lys Ala
            260                 265                 270

Phe Gln Thr Phe Leu Gly Lys Ala Asp Val Ser Gln Glu Val Glu Glu
```

-continued

```
            275                 280                 285
Val Leu Ala Glu Ser Arg Val Gln Arg Ser Ile Arg Leu Val Ser Val
    290                 295                 300

Leu Glu Leu Leu Arg Ala Pro Tyr Val Arg Trp Gln Val Val Thr Val
305                 310                 315                 320

Ile Val Thr Met Ala Cys Tyr Gln Leu Cys Gly Leu Asn Ala Ile Trp
                325                 330                 335

Phe Tyr Thr Asn Ser Ile Phe Gly Lys Ala Gly Ile Pro Leu Ala Lys
                340                 345                 350

Ile Pro Tyr Val Thr Leu Ser Thr Gly Gly Ile Glu Thr Leu Ala Ala
                355                 360                 365

Val Phe Ser Gly Leu Val Ile Glu His Leu Gly Arg Arg Pro Leu Leu
    370                 375                 380

Ile Gly Gly Phe Gly Leu Met Gly Leu Phe Phe Gly Thr Leu Thr Ile
385                 390                 395                 400

Thr Leu Thr Leu Gln Asp His Ala Pro Trp Val Pro Tyr Leu Ser Ile
                405                 410                 415

Val Gly Ile Leu Ala Ile Ile Ala Ser Phe Cys Ser Gly Pro Gly Gly
                420                 425                 430

Ile Pro Phe Ile Leu Thr Gly Glu Phe Phe Gln Gln Ser Gln Arg Pro
                435                 440                 445

Ala Ala Phe Ile Ile Ala Gly Thr Val Asn Trp Leu Ser Asn Phe Ala
    450                 455                 460

Val Gly Leu Leu Phe Pro Phe Ile Gln Lys Ser Leu Asp Thr Tyr Cys
465                 470                 475                 480

Phe Leu Val Phe Ala Thr Ile Cys Ile Thr Gly Ala Ile Tyr Leu Tyr
                485                 490                 495

Phe Val Leu Pro Glu Thr Lys Asn Arg Thr Tyr Ala Glu Ile Ser Gln
                500                 505                 510

Ala Phe Ser Lys Arg Asn Lys Ala Tyr Pro Pro Glu Lys Ile Asp
                515                 520                 525

Ser Ala Val Thr Asp Gly Lys Ile Asn Gly Arg Pro
    530                 535                 540
```

<210> SEQ ID NO 9
<211> LENGTH: 541
<212> TYPE: PRT
<213> ORGANISM: Homo sapiens

<400> SEQUENCE: 9

```
Met Gly His Ser Pro Val Leu Pro Leu Cys Ala Ser Val Ser Leu
1               5                   10                  15

Leu Gly Gly Leu Thr Phe Gly Tyr Glu Leu Ala Val Ile Ser Gly Ala
                20                  25                  30

Leu Leu Pro Leu Gln Leu Asp Phe Gly Leu Ser Cys Leu Glu Gln Glu
                35                  40                  45

Phe Leu Val Gly Ser Leu Leu Gly Ala Leu Leu Ala Ser Leu Val
    50                  55                  60

Gly Gly Phe Leu Ile Asp Cys Tyr Gly Arg Lys Gln Ala Ile Leu Gly
65                  70                  75                  80

Ser Asn Leu Val Leu Leu Ala Gly Ser Leu Thr Leu Gly Leu Ala Gly
                85                  90                  95

Ser Leu Ala Trp Leu Val Leu Gly Arg Ala Val Val Gly Phe Ala Ile
                100                 105                 110
```

```
Ser Leu Ser Ser Met Ala Cys Cys Ile Tyr Val Ser Glu Leu Val Gly
            115                 120                 125

Pro Arg Gln Arg Gly Val Leu Val Ser Leu Tyr Glu Ala Gly Ile Thr
        130                 135                 140

Val Gly Ile Leu Leu Ser Tyr Ala Leu Asn Tyr Ala Leu Ala Gly Thr
145                 150                 155                 160

Pro Trp Gly Trp Arg His Met Phe Gly Trp Ala Thr Ala Pro Ala Val
                165                 170                 175

Leu Gln Ser Leu Ser Leu Leu Phe Leu Pro Ala Gly Thr Asp Glu Thr
                180                 185                 190

Ala Thr His Lys Asp Leu Ile Pro Leu Gln Gly Gly Glu Ala Pro Lys
            195                 200                 205

Leu Gly Pro Gly Arg Pro Arg Tyr Ser Phe Leu Asp Leu Phe Arg Ala
        210                 215                 220

Arg Asp Asn Met Arg Gly Arg Thr Thr Val Gly Leu Gly Leu Val Leu
225                 230                 235                 240

Phe Gln Gln Leu Thr Gly Gln Pro Asn Val Leu Cys Tyr Ala Ser Thr
                245                 250                 255

Ile Phe Ser Ser Val Gly Phe His Gly Gly Ser Ser Ala Val Leu Ala
            260                 265                 270

Ser Val Gly Leu Gly Ala Val Lys Val Ala Ala Thr Leu Thr Ala Met
        275                 280                 285

Gly Leu Val Asp Arg Ala Gly Arg Arg Ala Leu Leu Leu Ala Gly Cys
        290                 295                 300

Ala Leu Met Ala Leu Ser Val Ser Gly Ile Gly Leu Val Ser Phe Ala
305                 310                 315                 320

Val Pro Met Asp Ser Gly Pro Ser Cys Leu Ala Val Pro Asn Ala Thr
                325                 330                 335

Gly Gln Thr Gly Leu Pro Gly Asp Ser Gly Leu Leu Gln Asp Ser Ser
            340                 345                 350

Leu Pro Pro Ile Pro Arg Thr Asn Glu Asp Gln Arg Glu Pro Ile Leu
        355                 360                 365

Ser Thr Ala Lys Lys Thr Lys Pro His Pro Arg Ser Gly Asp Pro Ser
370                 375                 380

Ala Pro Pro Arg Leu Ala Leu Ser Ser Ala Leu Pro Gly Pro Pro Leu
385                 390                 395                 400

Pro Ala Arg Gly His Ala Leu Leu Arg Trp Thr Ala Leu Leu Cys Leu
                405                 410                 415

Met Val Phe Val Ser Ala Phe Ser Phe Gly Phe Gly Pro Val Thr Trp
                420                 425                 430

Leu Val Leu Ser Glu Ile Tyr Pro Val Glu Ile Arg Gly Arg Ala Phe
            435                 440                 445

Ala Phe Cys Asn Ser Phe Asn Trp Ala Ala Asn Leu Phe Ile Ser Leu
        450                 455                 460

Ser Phe Leu Asp Leu Ile Gly Thr Ile Gly Leu Ser Trp Thr Phe Leu
465                 470                 475                 480

Leu Tyr Gly Leu Thr Ala Val Leu Gly Leu Gly Phe Ile Tyr Leu Phe
                485                 490                 495

Val Pro Glu Thr Lys Gly Gln Ser Leu Ala Glu Ile Asp Gln Gln Phe
            500                 505                 510

Gln Lys Arg Arg Phe Thr Leu Ser Phe Gly His Arg Gln Asn Ser Thr
        515                 520                 525

Gly Ile Pro Tyr Ser Arg Ile Glu Ile Ser Ala Ala Ser
```

-continued

```
                530                 535                 540

<210> SEQ ID NO 10
<211> LENGTH: 496
<212> TYPE: PRT
<213> ORGANISM: Homo sapiens

<400> SEQUENCE: 10

Met Arg Ala Leu Arg Leu Ile Gln Gly Arg Ile Leu Leu Leu Thr
1               5                   10                  15

Ile Cys Ala Ala Gly Ile Gly Gly Thr Phe Gln Phe Gly Tyr Asn Leu
                20                  25                  30

Ser Ile Ile Asn Ala Pro Thr Leu His Ile Gln Glu Phe Thr Asn Glu
            35                  40                  45

Thr Trp Gln Ala Arg Thr Gly Glu Pro Leu Pro Asp His Leu Val Leu
    50                  55                  60

Leu Met Trp Ser Leu Ile Val Ser Leu Tyr Pro Leu Gly Gly Leu Phe
65                  70                  75                  80

Gly Ala Leu Leu Ala Gly Pro Leu Ala Ile Thr Leu Gly Arg Lys Lys
                85                  90                  95

Ser Leu Leu Val Asn Asn Ile Phe Val Val Ser Ala Ala Ile Leu Phe
            100                 105                 110

Gly Phe Ser Arg Lys Ala Gly Ser Phe Glu Met Ile Met Leu Gly Arg
        115                 120                 125

Leu Leu Val Gly Val Asn Ala Gly Val Ser Met Asn Ile Gln Pro Met
130                 135                 140

Tyr Leu Gly Glu Ser Ala Pro Lys Glu Leu Arg Gly Ala Val Ala Met
145                 150                 155                 160

Ser Ser Ala Ile Phe Thr Ala Leu Gly Ile Val Met Gly Gln Val Val
                165                 170                 175

Gly Leu Arg Glu Leu Leu Gly Gly Pro Gln Ala Trp Pro Leu Leu Leu
            180                 185                 190

Ala Ser Cys Leu Val Pro Gly Ala Leu Gln Leu Ala Ser Leu Pro Leu
        195                 200                 205

Leu Pro Glu Ser Pro Arg Tyr Leu Leu Ile Asp Cys Gly Asp Thr Glu
210                 215                 220

Ala Cys Leu Ala Ala Leu Arg Arg Leu Arg Gly Ser Gly Asp Leu Ala
225                 230                 235                 240

Gly Glu Leu Glu Glu Leu Glu Glu Glu Arg Ala Ala Cys Gln Gly Cys
                245                 250                 255

Arg Ala Arg Arg Pro Trp Glu Leu Phe Gln His Arg Ala Leu Arg Arg
            260                 265                 270

Gln Val Thr Ser Leu Val Val Leu Gly Ser Ala Met Glu Leu Cys Gly
        275                 280                 285

Asn Asp Ser Val Tyr Ala Tyr Ala Ser Ser Val Phe Arg Lys Ala Gly
290                 295                 300

Val Pro Glu Ala Lys Ile Gln Tyr Ala Ile Ile Gly Thr Gly Ser Cys
305                 310                 315                 320

Glu Leu Leu Thr Ala Val Val Ser Cys Val Val Ile Glu Arg Val Gly
                325                 330                 335

Arg Arg Val Leu Leu Ile Gly Gly Tyr Ser Leu Met Thr Cys Trp Gly
            340                 345                 350

Ser Ile Phe Thr Val Ala Leu Cys Leu Gln Ser Ser Phe Pro Trp Thr
        355                 360                 365
```

-continued

Leu Tyr Leu Ala Met Ala Cys Ile Phe Ala Phe Ile Leu Ser Phe Gly
    370                 375                 380

Ile Gly Pro Ala Gly Val Thr Gly Ile Leu Ala Thr Glu Leu Phe Asp
385                 390                 395                 400

Gln Met Ala Arg Pro Ala Ala Cys Met Val Cys Gly Ala Leu Met Trp
                405                 410                 415

Ile Met Leu Ile Leu Val Gly Leu Gly Phe Pro Phe Ile Met Glu Ala
            420                 425                 430

Leu Ser His Phe Leu Tyr Val Pro Phe Leu Gly Val Cys Val Cys Gly
        435                 440                 445

Ala Ile Tyr Thr Gly Leu Phe Leu Pro Glu Thr Lys Gly Lys Thr Phe
    450                 455                 460

Gln Glu Ile Ser Lys Glu Leu His Arg Leu Asn Phe Pro Arg Arg Ala
465                 470                 475                 480

Gln Gly Pro Thr Trp Arg Ser Leu Glu Val Ile Gln Ser Thr Glu Leu
                485                 490                 495

<210> SEQ ID NO 11
<211> LENGTH: 617
<212> TYPE: PRT
<213> ORGANISM: Homo sapiens

<400> SEQUENCE: 11

Met Val Pro Val Glu Asn Thr Glu Gly Pro Ser Leu Leu Asn Gln Lys
1               5                   10                  15

Gly Thr Ala Val Glu Thr Glu Gly Ser Gly Ser Arg His Pro Pro Trp
            20                  25                  30

Ala Arg Gly Cys Gly Met Phe Thr Phe Leu Ser Val Thr Ala Ala
        35                  40                  45

Val Ser Gly Leu Leu Val Gly Tyr Glu Leu Gly Ile Ile Ser Gly Ala
    50                  55                  60

Leu Leu Gln Ile Lys Thr Leu Leu Ala Leu Ser Cys His Glu Gln Glu
65                  70                  75                  80

Met Val Val Ser Ser Leu Val Ile Gly Ala Leu Leu Ala Ser Leu Thr
                85                  90                  95

Gly Gly Val Leu Ile Asp Arg Tyr Gly Arg Arg Thr Ala Ile Ile Leu
            100                 105                 110

Ser Ser Cys Leu Leu Gly Leu Gly Ser Leu Val Leu Ile Leu Ser Leu
        115                 120                 125

Ser Tyr Thr Val Leu Ile Val Gly Arg Ile Ala Ile Gly Val Ser Ile
    130                 135                 140

Ser Leu Ser Ser Ile Ala Thr Cys Val Tyr Ile Ala Glu Ile Ala Pro
145                 150                 155                 160

Gln His Arg Arg Gly Leu Leu Val Ser Leu Asn Glu Leu Met Ile Val
                165                 170                 175

Ile Gly Ile Leu Ser Ala Tyr Ile Ser Asn Tyr Ala Phe Ala Asn Val
            180                 185                 190

Phe His Gly Trp Lys Tyr Met Phe Gly Leu Val Ile Pro Leu Gly Val
        195                 200                 205

Leu Gln Ala Ile Ala Met Tyr Phe Leu Pro Pro Ser Pro Arg Phe Leu
    210                 215                 220

Val Met Lys Gly Gln Glu Gly Ala Ala Ser Lys Val Leu Gly Arg Leu
225                 230                 235                 240

Arg Ala Leu Ser Asp Thr Thr Glu Glu Leu Thr Val Ile Lys Ser Ser
                245                 250                 255

```
Leu Lys Asp Glu Tyr Gln Tyr Ser Phe Trp Asp Leu Phe Arg Ser Lys
        260                 265                 270

Asp Asn Met Arg Thr Arg Ile Met Ile Gly Leu Thr Leu Val Phe Phe
            275                 280                 285

Val Gln Ile Thr Gly Gln Pro Asn Ile Leu Phe Tyr Ala Ser Thr Val
        290                 295                 300

Leu Lys Ser Val Gly Phe Gln Ser Asn Glu Ala Ala Ser Leu Ala Ser
305                 310                 315                 320

Thr Gly Val Gly Val Lys Val Ile Ser Thr Ile Pro Ala Thr Leu
                325                 330                 335

Leu Val Asp His Val Gly Ser Lys Thr Phe Leu Cys Ile Gly Ser Ser
            340                 345                 350

Val Met Ala Ala Ser Leu Val Thr Met Gly Ile Val Asn Leu Asn Ile
        355                 360                 365

His Met Asn Phe Thr His Ile Cys Arg Ser His Asn Ser Ile Asn Gln
    370                 375                 380

Ser Leu Asp Glu Ser Val Ile Tyr Gly Pro Gly Asn Leu Ser Thr Asn
385                 390                 395                 400

Asn Asn Thr Leu Arg Asp His Phe Lys Gly Ile Ser Ser His Ser Arg
                405                 410                 415

Ser Ser Leu Met Pro Leu Arg Asn Asp Val Asp Lys Arg Gly Glu Thr
            420                 425                 430

Thr Ser Ala Ser Leu Leu Asn Ala Gly Leu Ser His Thr Glu Tyr Gln
        435                 440                 445

Ile Val Thr Asp Pro Gly Asp Val Pro Ala Phe Leu Lys Trp Leu Ser
    450                 455                 460

Leu Ala Ser Leu Leu Val Tyr Val Ala Ala Phe Ser Ile Gly Leu Gly
465                 470                 475                 480

Pro Met Pro Trp Leu Val Leu Ser Glu Ile Phe Pro Gly Gly Ile Arg
                485                 490                 495

Gly Arg Ala Met Ala Leu Thr Ser Ser Met Asn Trp Gly Ile Asn Leu
            500                 505                 510

Leu Ile Ser Leu Thr Phe Leu Thr Val Thr Asp Leu Ile Gly Leu Pro
        515                 520                 525

Trp Val Cys Phe Ile Tyr Thr Ile Met Ser Leu Ala Ser Leu Leu Phe
    530                 535                 540

Val Val Met Phe Ile Pro Glu Thr Lys Gly Cys Ser Leu Glu Gln Ile
545                 550                 555                 560

Ser Met Glu Leu Ala Lys Val Asn Tyr Val Lys Asn Asn Ile Cys Phe
                565                 570                 575

Met Ser His His Gln Glu Glu Leu Val Pro Lys Gln Pro Gln Lys Arg
            580                 585                 590

Lys Pro Gln Glu Gln Leu Leu Glu Cys Asn Lys Leu Cys Gly Arg Gly
        595                 600                 605

Gln Ser Arg Gln Leu Ser Pro Glu Thr
    610                 615

<210> SEQ ID NO 12
<211> LENGTH: 629
<212> TYPE: PRT
<213> ORGANISM: Homo sapiens
<220> FEATURE:
<221> NAME/KEY: misc_feature
<222> LOCATION: (227)..(227)
<223> OTHER INFORMATION: Xaa can be any naturally occurring amino acid
```

```
<220> FEATURE:
<221> NAME/KEY: misc_feature
<222> LOCATION: (436)..(436)
<223> OTHER INFORMATION: Xaa can be any naturally occurring amino acid

<400> SEQUENCE: 12
```

| | | | | | | | | | | | | | | | |
|---|---|---|---|---|---|---|---|---|---|---|---|---|---|---|---|
| Met | Gly | Glu | Arg | Arg | Lys | Gln | Pro | Glu | Pro | Asp | Ala | Ala | Ser | Ala | |
| 1 | | | | 5 | | | | | 10 | | | | | 15 | |
| Ala | Gly | Glu | Cys | Ser | Leu | Leu | Ala | Ala | Glu | Ser | Ser | Thr | Ser | Leu | |
| | | | 20 | | | | | 25 | | | | | 30 | | |
| Gln | Ser | Ala | Gly | Ala | Gly | Gly | Gly | Val | Gly | Asp | Leu | Glu | Arg | Ala | |
| | | 35 | | | | | 40 | | | | | 45 | | | |
| Ala | Arg | Arg | Gln | Phe | Gln | Gln | Asp | Glu | Thr | Pro | Ala | Phe | Val | Tyr | Val |
| 50 | | | | | 55 | | | | | 60 | | | | | |
| Val | Ala | Val | Phe | Ser | Ala | Leu | Gly | Gly | Phe | Leu | Phe | Gly | Tyr | Asp | Thr |
| 65 | | | | | 70 | | | | | 75 | | | | | 80 |
| Gly | Val | Val | Ser | Gly | Ala | Met | Leu | Leu | Leu | Lys | Arg | Gln | Leu | Ser | Leu |
| | | | | 85 | | | | | 90 | | | | | 95 | |
| Asp | Ala | Leu | Trp | Gln | Glu | Leu | Leu | Val | Ser | Ser | Thr | Val | Gly | Ala | Ala |
| | | | 100 | | | | | 105 | | | | | 110 | | |
| Ala | Val | Ser | Ala | Leu | Ala | Gly | Gly | Ala | Leu | Asn | Gly | Val | Phe | Gly | Arg |
| | | 115 | | | | | 120 | | | | | 125 | | | |
| Arg | Ala | Ala | Ile | Leu | Leu | Ala | Ser | Ala | Leu | Phe | Thr | Ala | Gly | Ser | Ala |
| | 130 | | | | | 135 | | | | | 140 | | | | |
| Val | Leu | Ala | Ala | Ala | Asn | Asn | Lys | Glu | Thr | Leu | Leu | Ala | Gly | Arg | Leu |
| 145 | | | | | 150 | | | | | 155 | | | | | 160 |
| Val | Val | Gly | Leu | Gly | Ile | Gly | Ile | Ala | Ser | Met | Thr | Val | Pro | Val | Tyr |
| | | | | 165 | | | | | 170 | | | | | 175 | |
| Ile | Ala | Glu | Val | Ser | Pro | Pro | Asn | Leu | Arg | Gly | Arg | Leu | Val | Thr | Ile |
| | | | 180 | | | | | 185 | | | | | 190 | | |
| Asn | Thr | Leu | Phe | Ile | Thr | Gly | Gly | Gln | Phe | Phe | Ala | Ser | Val | Val | Asp |
| | | | | 195 | | | | | 200 | | | | | 205 | |
| Gly | Ala | Phe | Ser | Tyr | Leu | Gln | Lys | Asp | Gly | Trp | Arg | Tyr | Met | Leu | Gly |
| | 210 | | | | | 215 | | | | | 220 | | | | |
| Leu | Ala | Xaa | Val | Pro | Ala | Val | Ile | Gln | Phe | Phe | Gly | Phe | Leu | Phe | Leu |
| 225 | | | | | 230 | | | | | 235 | | | | | 240 |
| Pro | Glu | Ser | Pro | Arg | Trp | Leu | Ile | Gln | Lys | Gly | Gln | Thr | Gln | Lys | Ala |
| | | | | 245 | | | | | 250 | | | | | 255 | |
| Arg | Arg | Ile | Leu | Ser | Gln | Met | Arg | Gly | Asn | Gln | Thr | Ile | Asp | Glu | Glu |
| | | | 260 | | | | | 265 | | | | | 270 | | |
| Tyr | Asp | Ser | Ile | Lys | Asn | Asn | Ile | Glu | Glu | Glu | Lys | Glu | Val | Gly | |
| | | 275 | | | | | 280 | | | | | 285 | | | |
| Ser | Ala | Gly | Pro | Val | Ile | Cys | Arg | Met | Leu | Ser | Tyr | Pro | Pro | Thr | Arg |
| | 290 | | | | | 295 | | | | | 300 | | | | |
| Arg | Ala | Leu | Ile | Val | Gly | Cys | Gly | Leu | Gln | Met | Phe | Gln | Gln | Leu | Ser |
| 305 | | | | | 310 | | | | | 315 | | | | | 320 |
| Gly | Ile | Asn | Thr | Ile | Met | Tyr | Tyr | Ser | Ala | Thr | Ile | Leu | Gln | Met | Ser |
| | | | | 325 | | | | | 330 | | | | | 335 | |
| Gly | Val | Glu | Asp | Asp | Arg | Leu | Ala | Ile | Trp | Leu | Ala | Ser | Val | Thr | Ala |
| | | | 340 | | | | | 345 | | | | | 350 | | |
| Phe | Thr | Asn | Phe | Ile | Phe | Thr | Leu | Val | Gly | Val | Trp | Leu | Val | Glu | Lys |
| | | 355 | | | | | 360 | | | | | 365 | | | |
| Val | Gly | Arg | Arg | Lys | Leu | Thr | Phe | Gly | Ser | Leu | Ala | Gly | Thr | Thr | Val |
| | 370 | | | | | 375 | | | | | 380 | | | | |

```
Ala Leu Ile Ile Leu Ala Leu Gly Phe Val Leu Ser Ala Gln Val Ser
385                 390                 395                 400

Pro Arg Ile Thr Phe Lys Pro Ile Ala Pro Ser Gly Gln Asn Ala Thr
            405                 410                 415

Cys Thr Arg Tyr Ser Tyr Cys Asn Glu Cys Met Leu Asp Pro Asp Cys
            420                 425                 430

Gly Phe Cys Xaa Lys Met Asn Lys Ser Thr Val Ile Asp Ser Ser Cys
            435                 440                 445

Val Pro Val Asn Lys Ala Ser Thr Asn Glu Ala Ala Trp Gly Arg Cys
        450                 455                 460

Glu Asn Glu Thr Lys Phe Lys Thr Glu Asp Ile Phe Trp Ala Tyr Asn
465                 470                 475                 480

Phe Cys Pro Thr Pro Tyr Ser Trp Thr Ala Leu Leu Gly Leu Ile Leu
            485                 490                 495

Tyr Leu Val Phe Phe Ala Pro Gly Met Gly Pro Met Pro Trp Thr Val
            500                 505                 510

Asn Ser Glu Ile Tyr Pro Leu Trp Ala Arg Ser Thr Gly Asn Ala Cys
            515                 520                 525

Ser Ser Gly Ile Asn Trp Ile Phe Asn Val Leu Val Ser Leu Thr Phe
        530                 535                 540

Leu His Thr Ala Glu Tyr Leu Thr Tyr Tyr Gly Ala Phe Phe Leu Tyr
545                 550                 555                 560

Ala Gly Phe Ala Ala Val Gly Leu Leu Phe Ile Tyr Gly Cys Leu Pro
            565                 570                 575

Glu Thr Lys Gly Lys Lys Leu Glu Glu Ile Glu Ser Leu Phe Asp Asn
            580                 585                 590

Arg Leu Cys Thr Cys Gly Thr Ser Asp Ser Asp Glu Gly Arg Tyr Ile
            595                 600                 605

Glu Tyr Ile Arg Val Lys Gly Ser Asn Tyr His Leu Ser Asp Asn Asp
        610                 615                 620

Ala Ser Asp Val Glu
625

<210> SEQ ID NO 13
<211> LENGTH: 497
<212> TYPE: PRT
<213> ORGANISM: Homo sapiens

<400> SEQUENCE: 13

Met Asp Asn Arg Gln Asn Val Thr Pro Ala Leu Ile Phe Ala Ile Thr
1               5                   10                  15

Val Ala Thr Ile Gly Ser Phe Gln Phe Gly Tyr Asn Thr Gly Val Ile
            20                  25                  30

Asn Ala Pro Glu Thr Ile Ile Lys Glu Phe Ile Asn Lys Thr Leu Thr
            35                  40                  45

Asp Lys Ala Asn Ala Pro Pro Ser Glu Val Leu Leu Thr Asn Leu Trp
        50                  55                  60

Ser Leu Ser Val Ala Ile Phe Ser Val Gly Gly Met Ile Gly Ser Phe
65                  70                  75                  80

Ser Val Gly Leu Phe Val Asn Arg Phe Gly Arg Arg Asn Ser Met Leu
            85                  90                  95

Ile Val Asn Leu Leu Ala Ala Thr Gly Gly Cys Leu Met Gly Leu Cys
            100                 105                 110

Lys Ile Ala Glu Ser Val Glu Met Leu Ile Leu Gly Arg Leu Val Ile
            115                 120                 125
```

```
Gly Leu Phe Cys Gly Leu Cys Thr Gly Phe Val Pro Met Tyr Ile Gly
            130                 135                 140

Glu Ile Ser Pro Thr Ala Leu Arg Gly Ala Phe Gly Thr Leu Asn Gln
145                 150                 155                 160

Leu Gly Ile Val Ile Gly Ile Leu Val Ala Gln Ile Phe Gly Leu Glu
                165                 170                 175

Leu Ile Leu Gly Ser Glu Glu Leu Trp Pro Val Leu Leu Gly Phe Thr
            180                 185                 190

Ile Leu Pro Ala Ile Leu Gln Ser Ala Ala Leu Pro Cys Cys Pro Glu
        195                 200                 205

Ser Pro Arg Phe Leu Leu Ile Asn Arg Lys Lys Glu Glu Asn Ala Thr
    210                 215                 220

Arg Ile Leu Gln Arg Leu Trp Gly Thr Gln Asp Val Ser Gln Asp Ile
225                 230                 235                 240

Gln Glu Met Lys Asp Glu Ser Ala Arg Met Ser Gln Glu Lys Gln Val
                245                 250                 255

Thr Val Leu Glu Leu Phe Arg Val Ser Ser Tyr Arg Gln Pro Ile Ile
            260                 265                 270

Ile Ser Ile Val Leu Gln Leu Ser Gln Gln Leu Ser Gly Ile Asn Ala
        275                 280                 285

Val Phe Tyr Tyr Ser Thr Gly Ile Phe Lys Asp Ala Gly Val Gln Gln
    290                 295                 300

Pro Ile Tyr Ala Thr Ile Ser Ala Gly Val Val Asn Thr Ile Phe Thr
305                 310                 315                 320

Leu Leu Ser Leu Phe Leu Val Glu Arg Ala Gly Arg Arg Thr Leu His
                325                 330                 335

Met Ile Gly Leu Gly Gly Met Ala Phe Cys Ser Thr Leu Met Thr Val
            340                 345                 350

Ser Leu Leu Leu Lys Asn His Tyr Asn Gly Met Ser Phe Val Cys Ile
        355                 360                 365

Gly Ala Ile Leu Val Phe Val Ala Cys Phe Glu Ile Gly Pro Gly Pro
    370                 375                 380

Ile Pro Trp Phe Ile Val Ala Glu Leu Phe Ser Gln Gly Pro Arg Pro
385                 390                 395                 400

Ala Ala Met Ala Val Ala Gly Cys Ser Asn Trp Thr Ser Asn Phe Leu
                405                 410                 415

Val Gly Leu Leu Phe Pro Ser Ala Ala Tyr Tyr Leu Gly Ala Tyr Val
            420                 425                 430

Phe Ile Ile Phe Thr Gly Phe Leu Ile Thr Phe Leu Ala Phe Thr Phe
        435                 440                 445

Phe Lys Val Pro Glu Thr Arg Gly Arg Thr Phe Glu Asp Ile Thr Arg
    450                 455                 460

Ala Phe Glu Gly Gln Ala His Gly Ala Asp Arg Ser Gly Lys Asp Gly
465                 470                 475                 480

Val Met Gly Met Asn Ser Ile Glu Pro Ala Lys Glu Thr Thr Thr Asn
                485                 490                 495

Val

<210> SEQ ID NO 14
<211> LENGTH: 520
<212> TYPE: PRT
<213> ORGANISM: Homo sapiens

<400> SEQUENCE: 14
```

Met Glu Phe His Asn Gly Gly His Val Ser Gly Ile Gly Phe Leu
1               5                   10                  15

Val Ser Leu Thr Ser Arg Met Lys Pro His Thr Leu Ala Val Thr Pro
            20                  25                  30

Ala Leu Ile Phe Ala Ile Thr Val Ala Thr Ile Gly Ser Phe Gln Phe
            35                  40                  45

Gly Tyr Asn Thr Gly Val Ile Asn Ala Pro Glu Thr Ile Ile Lys Glu
        50                  55                  60

Phe Ile Asn Lys Thr Leu Thr Asp Lys Ala Asn Ala Pro Pro Ser Glu
65                  70                  75                  80

Val Leu Leu Thr Asn Leu Trp Ser Leu Ser Val Ala Ile Phe Ser Val
                85                  90                  95

Gly Gly Met Ile Gly Ser Phe Ser Val Gly Leu Phe Val Asn Arg Phe
            100                 105                 110

Gly Arg Arg Asn Ser Met Leu Ile Val Asn Leu Leu Ala Ala Thr Gly
            115                 120                 125

Gly Cys Leu Met Gly Leu Cys Lys Ile Ala Glu Ser Val Glu Met Leu
130                 135                 140

Ile Leu Gly Arg Leu Val Ile Gly Leu Phe Cys Gly Leu Cys Thr Gly
145                 150                 155                 160

Phe Val Pro Met Tyr Ile Gly Glu Ile Ser Pro Thr Ala Leu Arg Gly
                165                 170                 175

Ala Phe Gly Thr Leu Asn Gln Leu Gly Ile Val Ile Gly Ile Leu Val
            180                 185                 190

Ala Gln Ile Phe Gly Leu Glu Leu Ile Leu Gly Ser Glu Glu Leu Trp
        195                 200                 205

Pro Val Leu Leu Gly Phe Thr Ile Leu Pro Ala Ile Leu Gln Ser Ala
            210                 215                 220

Ala Leu Pro Cys Cys Pro Glu Ser Pro Arg Phe Leu Leu Ile Asn Arg
225                 230                 235                 240

Lys Lys Glu Glu Asn Ala Thr Arg Ile Leu Gln Arg Leu Trp Gly Thr
                245                 250                 255

Gln Asp Val Ser Gln Asp Ile Gln Glu Met Lys Asp Glu Ser Ala Arg
            260                 265                 270

Met Ser Gln Glu Lys Gln Val Thr Val Leu Glu Leu Phe Arg Val Ser
        275                 280                 285

Ser Tyr Arg Gln Pro Ile Ile Ile Ser Ile Val Leu Gln Leu Ser Gln
        290                 295                 300

Gln Leu Ser Gly Ile Asn Ala Val Phe Tyr Tyr Ser Thr Gly Ile Phe
305                 310                 315                 320

Lys Asp Ala Gly Val Gln Gln Pro Ile Tyr Ala Thr Ile Ser Ala Gly
                325                 330                 335

Val Val Asn Thr Ile Phe Thr Leu Leu Ser Leu Phe Leu Val Glu Arg
            340                 345                 350

Ala Gly Arg Arg Thr Leu His Met Ile Gly Leu Gly Gly Met Ala Phe
        355                 360                 365

Cys Ser Thr Leu Met Thr Val Ser Leu Leu Lys Asn His Tyr Asn
        370                 375                 380

Gly Met Ser Phe Val Cys Ile Gly Ala Ile Leu Val Phe Val Ala Cys
385                 390                 395                 400

Phe Glu Ile Gly Pro Gly Pro Ile Pro Trp Phe Ile Val Ala Glu Leu
                405                 410                 415

```
Phe Ser Gln Gly Pro Arg Pro Ala Ala Met Ala Val Ala Gly Cys Ser
            420                 425                 430

Asn Trp Thr Ser Asn Phe Leu Val Gly Leu Leu Phe Pro Ser Ala Ala
        435                 440                 445

Tyr Tyr Leu Gly Ala Tyr Val Phe Ile Ile Phe Thr Gly Phe Leu Ile
450                 455                 460

Thr Phe Leu Ala Phe Thr Phe Phe Lys Val Pro Glu Thr Arg Gly Arg
465                 470                 475                 480

Thr Phe Glu Asp Ile Thr Arg Ala Phe Glu Gly Gln Ala His Gly Ala
                485                 490                 495

Asp Arg Ser Gly Lys Asp Gly Val Met Gly Met Asn Ser Ile Glu Pro
            500                 505                 510

Ala Lys Glu Thr Thr Thr Asn Val
        515                 520

<210> SEQ ID NO 15
<211> LENGTH: 664
<212> TYPE: PRT
<213> ORGANISM: Homo sapiens

<400> SEQUENCE: 15

Met Asp Ser Ser Thr Trp Ser Pro Lys Thr Thr Ala Val Thr Arg Pro
1               5                   10                  15

Val Glu Thr His Glu Leu Ile Arg Asn Ala Ala Asp Ile Ser Ile Ile
            20                  25                  30

Val Ile Tyr Phe Val Val Met Ala Val Gly Leu Trp Ala Met Phe
        35                  40                  45

Ser Thr Asn Arg Gly Thr Val Gly Gly Phe Phe Leu Ala Gly Arg Ser
    50                  55                  60

Met Val Trp Trp Pro Ile Gly Ala Ser Leu Phe Ala Ser Asn Ile Gly
65                  70                  75                  80

Ser Gly His Phe Val Gly Leu Ala Gly Thr Gly Ala Ala Ser Gly Ile
                85                  90                  95

Ala Ile Gly Gly Phe Glu Trp Asn Ala Leu Val Leu Val Val Val Leu
            100                 105                 110

Gly Trp Leu Phe Val Pro Ile Tyr Ile Lys Ala Gly Val Val Thr Met
        115                 120                 125

Pro Glu Tyr Leu Arg Lys Arg Phe Gly Gly Gln Arg Ile Gln Val Tyr
130                 135                 140

Leu Ser Leu Leu Ser Leu Leu Leu Tyr Ile Phe Thr Lys Ile Ser Ala
145                 150                 155                 160

Asp Ile Phe Ser Gly Ala Ile Phe Ile Asn Leu Ala Leu Gly Leu Asn
                165                 170                 175

Leu Tyr Leu Ala Ile Phe Leu Leu Leu Ala Ile Thr Ala Leu Tyr Thr
            180                 185                 190

Ile Thr Gly Gly Leu Ala Ala Val Ile Tyr Thr Asp Thr Leu Gln Thr
        195                 200                 205

Val Ile Met Leu Val Gly Ser Leu Ile Leu Thr Gly Phe Ala Phe His
210                 215                 220

Glu Val Gly Gly Tyr Asp Ala Phe Met Glu Lys Tyr Met Lys Ala Ile
225                 230                 235                 240

Pro Thr Ile Val Ser Asp Gly Asn Thr Thr Phe Gln Glu Lys Cys Tyr
                245                 250                 255

Thr Pro Arg Ala Asp Ser Phe His Ile Phe Arg Asp Pro Leu Thr Gly
            260                 265                 270
```

```
Asp Leu Pro Trp Pro Gly Phe Ile Phe Gly Met Ser Ile Leu Thr Leu
            275                 280                 285
Trp Tyr Trp Cys Thr Asp Gln Val Ile Val Gln Arg Cys Leu Ser Ala
        290                 295                 300
Lys Asn Met Ser His Val Lys Gly Gly Cys Ile Leu Cys Gly Tyr Leu
305                 310                 315                 320
Lys Leu Met Pro Met Phe Ile Met Val Met Pro Gly Met Ile Ser Arg
                325                 330                 335
Ile Leu Tyr Thr Glu Lys Ile Ala Cys Val Val Pro Ser Glu Cys Glu
            340                 345                 350
Lys Tyr Cys Gly Thr Lys Val Gly Cys Thr Asn Ile Ala Tyr Pro Thr
        355                 360                 365
Leu Val Val Glu Leu Met Pro Asn Gly Leu Arg Gly Leu Met Leu Ser
    370                 375                 380
Val Met Leu Ala Ser Leu Met Ser Ser Leu Thr Ser Ile Phe Asn Ser
385                 390                 395                 400
Ala Ser Thr Leu Phe Thr Met Asp Ile Tyr Ala Lys Val Arg Lys Arg
                405                 410                 415
Ala Ser Glu Lys Glu Leu Met Ile Ala Gly Arg Leu Phe Ile Leu Val
            420                 425                 430
Leu Ile Gly Ile Ser Ile Ala Trp Val Pro Ile Val Gln Ser Ala Gln
        435                 440                 445
Ser Gly Gln Leu Phe Asp Tyr Ile Gln Ser Ile Thr Ser Tyr Leu Gly
    450                 455                 460
Pro Pro Ile Ala Ala Val Phe Leu Leu Ala Ile Phe Trp Lys Arg Val
465                 470                 475                 480
Asn Glu Pro Gly Ala Phe Trp Gly Leu Ile Leu Gly Leu Leu Ile Gly
                485                 490                 495
Ile Ser Arg Met Ile Thr Glu Phe Ala Tyr Gly Thr Gly Ser Cys Met
            500                 505                 510
Glu Pro Ser Asn Cys Pro Thr Ile Ile Cys Gly Val His Tyr Leu Tyr
        515                 520                 525
Phe Ala Ile Ile Leu Phe Ala Ile Ser Phe Ile Thr Ile Val Val Ile
    530                 535                 540
Ser Leu Leu Thr Lys Pro Ile Pro Asp Val His Leu Tyr Arg Leu Cys
545                 550                 555                 560
Trp Ser Leu Arg Asn Ser Lys Glu Glu Arg Ile Asp Leu Asp Ala Glu
                565                 570                 575
Glu Glu Asn Ile Gln Glu Gly Pro Lys Glu Thr Ile Glu Ile Glu Thr
            580                 585                 590
Gln Val Pro Glu Lys Lys Lys Gly Ile Phe Arg Arg Ala Tyr Asp Leu
        595                 600                 605
Phe Cys Gly Leu Glu Gln His Gly Ala Pro Lys Met Thr Glu Glu Glu
    610                 615                 620
Glu Lys Ala Met Lys Met Lys Met Thr Asp Thr Ser Glu Lys Pro Leu
625                 630                 635                 640
Trp Arg Thr Val Leu Asn Val Asn Gly Ile Ile Leu Val Thr Val Ala
                645                 650                 655
Val Phe Cys His Ala Tyr Phe Ala
            660

<210> SEQ ID NO 16
<211> LENGTH: 672
```

```
<212> TYPE: PRT
<213> ORGANISM: Homo sapiens

<400> SEQUENCE: 16

Met Glu Glu His Thr Glu Ala Gly Ser Ala Pro Glu Met Gly Ala Gln
1               5                   10                  15

Lys Ala Leu Ile Asp Asn Pro Ala Asp Ile Leu Val Ile Ala Ala Tyr
                20                  25                  30

Phe Leu Leu Val Ile Gly Val Gly Leu Trp Ser Met Cys Arg Thr Asn
                35                  40                  45

Arg Gly Thr Val Gly Gly Tyr Phe Leu Ala Gly Arg Ser Met Val Trp
        50                  55                  60

Trp Pro Val Gly Ala Ser Leu Phe Ala Ser Asn Ile Gly Ser Gly His
65                  70                  75                  80

Phe Val Gly Leu Ala Gly Thr Gly Ala Ala Ser Gly Leu Ala Val Ala
                85                  90                  95

Gly Phe Glu Trp Asn Ala Leu Phe Val Val Leu Leu Leu Gly Trp Leu
            100                 105                 110

Phe Ala Pro Val Tyr Leu Thr Ala Gly Val Ile Thr Met Pro Gln Tyr
        115                 120                 125

Leu Arg Lys Arg Phe Gly Gly Arg Arg Ile Arg Leu Tyr Leu Ser Val
130                 135                 140

Leu Ser Leu Phe Leu Tyr Ile Phe Thr Lys Ile Ser Val Asp Met Phe
145                 150                 155                 160

Ser Gly Ala Val Phe Ile Gln Gln Ala Leu Gly Trp Asn Ile Tyr Ala
                165                 170                 175

Ser Val Ile Ala Leu Leu Gly Ile Thr Met Ile Tyr Thr Val Thr Gly
                180                 185                 190

Gly Leu Ala Ala Leu Met Tyr Thr Asp Thr Val Gln Thr Phe Val Ile
            195                 200                 205

Leu Gly Gly Ala Cys Ile Leu Met Gly Tyr Ala Phe His Glu Val Gly
        210                 215                 220

Gly Tyr Ser Gly Leu Phe Asp Lys Tyr Leu Gly Ala Ala Thr Ser Leu
225                 230                 235                 240

Thr Val Ser Glu Asp Pro Ala Val Gly Asn Ile Ser Ser Phe Cys Tyr
                245                 250                 255

Arg Pro Arg Pro Asp Ser Tyr His Leu Leu Arg His Pro Val Thr Gly
                260                 265                 270

Asp Leu Pro Trp Pro Ala Leu Leu Leu Gly Leu Thr Ile Val Ser Gly
            275                 280                 285

Trp Tyr Trp Cys Ser Asp Gln Val Ile Val Gln Arg Cys Leu Ala Gly
        290                 295                 300

Lys Ser Leu Thr His Ile Lys Ala Gly Cys Ile Leu Cys Gly Tyr Leu
305                 310                 315                 320

Lys Leu Thr Pro Met Phe Leu Met Val Met Pro Gly Met Ile Ser Arg
                325                 330                 335

Ile Leu Tyr Pro Asp Glu Val Ala Cys Val Val Pro Glu Val Cys Arg
                340                 345                 350

Arg Val Cys Gly Thr Glu Val Gly Cys Ser Asn Ile Ala Tyr Pro Arg
            355                 360                 365

Leu Val Val Lys Leu Met Pro Asn Gly Leu Arg Gly Leu Met Leu Ala
        370                 375                 380

Val Met Leu Ala Ala Leu Met Ser Ser Leu Ala Ser Ile Phe Asn Ser
385                 390                 395                 400
```

```
Ser Ser Thr Leu Phe Thr Met Asp Ile Tyr Thr Arg Leu Arg Pro Arg
                405                 410                 415

Ala Gly Asp Arg Glu Leu Leu Val Gly Arg Leu Trp Val Val Phe
        420                 425                 430

Ile Val Val Val Ser Val Ala Trp Leu Pro Val Val Gln Ala Ala Gln
            435                 440                 445

Gly Gly Gln Leu Phe Asp Tyr Ile Gln Ala Val Ser Ser Tyr Leu Ala
    450                 455                 460

Pro Pro Val Ser Ala Val Phe Val Leu Ala Leu Phe Val Pro Arg Val
465                 470                 475                 480

Asn Glu Gln Gly Ala Phe Trp Gly Leu Ile Gly Leu Leu Met Gly
                485                 490                 495

Leu Ala Arg Leu Ile Pro Glu Phe Phe Gly Ser Gly Ser Cys Val
        500                 505                 510

Gln Pro Ser Ala Cys Pro Ala Phe Leu Cys Gly Val His Tyr Leu Tyr
            515                 520                 525

Phe Ala Ile Val Leu Phe Phe Cys Ser Gly Leu Leu Thr Leu Thr Val
    530                 535                 540

Ser Leu Cys Thr Ala Pro Ile Pro Arg Lys His Leu His Arg Leu Val
545                 550                 555                 560

Phe Ser Leu Arg His Ser Lys Glu Glu Arg Glu Asp Leu Asp Ala Asp
                565                 570                 575

Glu Gln Gln Gly Ser Ser Leu Pro Val Gln Asn Gly Cys Pro Glu Ser
                580                 585                 590

Ala Met Glu Met Asn Glu Pro Gln Ala Pro Ala Pro Ser Leu Phe Arg
                595                 600                 605

Gln Cys Leu Leu Trp Phe Cys Gly Met Ser Arg Gly Val Gly Ser
        610                 615                 620

Pro Pro Pro Leu Thr Gln Glu Glu Ala Ala Ala Ala Arg Arg Leu
625                 630                 635                 640

Glu Asp Ile Ser Glu Asp Pro Ser Trp Ala Arg Val Val Asn Leu Asn
                645                 650                 655

Ala Leu Leu Met Met Ala Val Ala Val Phe Leu Trp Gly Phe Tyr Ala
            660                 665                 670

<210> SEQ ID NO 17
<211> LENGTH: 659
<212> TYPE: PRT
<213> ORGANISM: Homo sapiens

<400> SEQUENCE: 17

Met Ala Ser Thr Val Ser Pro Ser Thr Ile Ala Glu Thr Pro Glu Pro
1               5                   10                  15

Pro Pro Leu Ser Asp His Ile Arg Asn Ala Ala Asp Ile Ser Val Ile
                20                  25                  30

Val Ile Tyr Phe Leu Val Val Met Ala Val Gly Leu Trp Ala Met Leu
            35                  40                  45

Lys Thr Asn Arg Gly Thr Ile Gly Gly Phe Phe Leu Ala Gly Arg Asp
        50                  55                  60

Met Ala Trp Trp Pro Met Gly Ala Ser Leu Phe Ala Ser Asn Ile Gly
65                  70                  75                  80

Ser Asn His Tyr Val Gly Leu Ala Gly Thr Gly Ala Ala Ser Gly Val
                85                  90                  95

Ala Thr Val Thr Phe Glu Trp Thr Ser Ser Val Met Leu Leu Ile Leu
```

-continued

```
                    100                 105                 110
Gly Trp Ile Phe Val Pro Ile Tyr Ile Lys Ser Gly Val Met Thr Met
                115                 120                 125
Pro Glu Tyr Leu Lys Lys Arg Phe Gly Gly Glu Arg Leu Gln Val Tyr
            130                 135                 140
Leu Ser Ile Leu Ser Leu Phe Ile Cys Val Val Leu Leu Ile Ser Ala
145                 150                 155                 160
Asp Ile Phe Ala Gly Ala Ile Phe Ile Lys Leu Ala Leu Gly Leu Asp
                        165                 170                 175
Leu Tyr Leu Ala Ile Phe Ile Leu Leu Ala Met Thr Ala Val Tyr Thr
                180                 185                 190
Thr Thr Gly Gly Leu Ala Ser Val Ile Tyr Thr Asp Thr Leu Gln Thr
                195                 200                 205
Ile Ile Met Leu Ile Gly Ser Phe Ile Leu Met Gly Phe Ala Phe Asn
            210                 215                 220
Glu Val Gly Gly Tyr Glu Ser Phe Thr Glu Lys Tyr Val Asn Ala Thr
225                 230                 235                 240
Pro Ser Val Val Glu Gly Asp Asn Leu Thr Ile Ser Ala Ser Cys Tyr
                        245                 250                 255
Thr Pro Arg Ala Asp Ser Phe His Ile Phe Arg Asp Ala Val Thr Gly
                260                 265                 270
Asp Ile Pro Trp Pro Gly Ile Ile Phe Gly Met Pro Ile Thr Ala Leu
            275                 280                 285
Trp Tyr Trp Cys Thr Asn Gln Val Ile Val Gln Arg Cys Leu Cys Gly
            290                 295                 300
Lys Asp Met Ser His Val Lys Ala Ala Cys Ile Met Cys Ala Tyr Leu
305                 310                 315                 320
Lys Leu Leu Pro Met Phe Leu Met Val Met Pro Gly Met Ile Ser Arg
                325                 330                 335
Ile Leu Tyr Thr Asp Met Val Ala Cys Val Val Pro Ser Glu Cys Val
                340                 345                 350
Lys His Cys Gly Val Asp Val Gly Cys Thr Asn Tyr Ala Tyr Pro Thr
                355                 360                 365
Met Val Leu Glu Leu Met Pro Gln Gly Leu Arg Gly Leu Met Leu Ser
                370                 375                 380
Val Met Leu Ala Ser Leu Met Ser Ser Leu Thr Ser Ile Phe Asn Ser
385                 390                 395                 400
Ala Ser Thr Leu Phe Thr Ile Asp Leu Tyr Thr Lys Met Arg Lys Gln
                        405                 410                 415
Ala Ser Glu Lys Glu Leu Leu Ile Ala Gly Arg Ile Phe Val Leu Leu
                420                 425                 430
Leu Thr Val Val Ser Ile Val Trp Val Pro Leu Val Gln Val Ser Gln
                435                 440                 445
Asn Gly Gln Leu Ile His Tyr Thr Glu Ser Ile Ser Ser Tyr Leu Gly
            450                 455                 460
Pro Pro Ile Ala Ala Val Phe Val Leu Ala Ile Phe Cys Lys Arg Val
465                 470                 475                 480
Asn Glu Gln Gly Ala Phe Trp Gly Leu Met Val Gly Leu Ala Met Gly
                        485                 490                 495
Leu Ile Arg Met Ile Thr Glu Phe Ala Tyr Gly Thr Gly Ser Cys Leu
                500                 505                 510
Ala Pro Ser Asn Cys Pro Lys Ile Ile Cys Gly Val His Tyr Leu Tyr
            515                 520                 525
```

```
Phe Ser Ile Val Leu Phe Phe Gly Ser Met Leu Val Thr Leu Gly Ile
    530                 535                 540

Ser Leu Leu Thr Lys Pro Ile Pro Asp Val His Leu Tyr Arg Leu Cys
545                 550                 555                 560

Trp Val Leu Arg Asn Ser Thr Glu Glu Arg Ile Asp Ile Asp Ala Glu
                565                 570                 575

Glu Lys Ser Gln Glu Glu Thr Asp Asp Gly Val Glu Gly Asp Tyr Pro
            580                 585                 590

Glu Lys Ser Arg Gly Cys Leu Lys Lys Ala Tyr Asp Leu Phe Cys Gly
        595                 600                 605

Leu Gln Lys Gly Pro Lys Leu Thr Lys Glu Glu Glu Ala Leu Ser
    610                 615                 620

Lys Lys Leu Thr Asp Thr Ser Glu Arg Pro Ser Trp Arg Thr Ile Val
625                 630                 635                 640

Asn Ile Asn Ala Ile Leu Leu Ala Val Val Phe Ile His Gly
                645                 650                 655

Tyr Tyr Ala
```

<210> SEQ ID NO 18
<211> LENGTH: 15
<212> TYPE: PRT
<213> ORGANISM: Artificial
<220> FEATURE:
<223> OTHER INFORMATION: Synthetic Human GLUT1 exofacial loop fragment

<400> SEQUENCE: 18

```
Thr Trp Asn His Arg Tyr Gly Glu Ser Ile Pro Ser Thr Thr Leu
1               5                   10                  15
```

<210> SEQ ID NO 19
<211> LENGTH: 12
<212> TYPE: PRT
<213> ORGANISM: Artificial
<220> FEATURE:
<223> OTHER INFORMATION: Synthetic Human GLUT 3 C-terminal fragment

<400> SEQUENCE: 19

```
Ser Ile Glu Pro Ala Lys Glu Thr Thr Thr Asn Val
1               5                   10
```

<210> SEQ ID NO 20
<211> LENGTH: 12
<212> TYPE: PRT
<213> ORGANISM: Artificial
<220> FEATURE:
<223> OTHER INFORMATION: Synthetic Human GLUT 5 C-terminal fragment

<400> SEQUENCE: 20

```
Glu Leu Lys Glu Leu Pro Pro Val Thr Ser Glu Gln
1               5                   10
```

<210> SEQ ID NO 21
<211> LENGTH: 21
<212> TYPE: DNA
<213> ORGANISM: Artificial
<220> FEATURE:
<223> OTHER INFORMATION: Synthetic GLUT 1 primer

<400> SEQUENCE: 21
tgaccatcgc gctagcactg c                                            21

```
<210> SEQ ID NO 22
<211> LENGTH: 21
<212> TYPE: DNA
<213> ORGANISM: Artificial
<220> FEATURE:
<223> OTHER INFORMATION: Synthetic GLUT 1 primer

<400> SEQUENCE: 22
tccaccctca ggcatggaac c                                      21

<210> SEQ ID NO 23
<211> LENGTH: 21
<212> TYPE: DNA
<213> ORGANISM: Artificial
<220> FEATURE:
<223> OTHER INFORMATION: Synthetic GLUT 1 primer

<400> SEQUENCE: 23
tggttcatcg tggctgaact c                                      21

<210> SEQ ID NO 24
<211> LENGTH: 21
<212> TYPE: DNA
<213> ORGANISM: Artificial
<220> FEATURE:
<223> OTHER INFORMATION: Synthetic GLUT 1 primer

<400> SEQUENCE: 24
tgagtttgca ggctcccaca g                                      21

<210> SEQ ID NO 25
<211> LENGTH: 21
<212> TYPE: DNA
<213> ORGANISM: Artificial
<220> FEATURE:
<223> OTHER INFORMATION: Synthetic GLUT 1 primer

<400> SEQUENCE: 25
tcataggcct cgctggcatg g                                      21

<210> SEQ ID NO 26
<211> LENGTH: 21
<212> TYPE: DNA
<213> ORGANISM: Artificial
<220> FEATURE:
<223> OTHER INFORMATION: Synthetic GLUT 1 primer

<400> SEQUENCE: 26
agcagtgagt ttgcaggctc c                                      21

<210> SEQ ID NO 27
<211> LENGTH: 21
<212> TYPE: DNA
<213> ORGANISM: Artificial
<220> FEATURE:
<223> OTHER INFORMATION: Synthetic GLUT 2 primer

<400> SEQUENCE: 27
tgtctggtgt gcgagccatc c                                      21

<210> SEQ ID NO 28
<211> LENGTH: 21
<212> TYPE: DNA
<213> ORGANISM: Artificial
<220> FEATURE:
<223> OTHER INFORMATION: Synthetic GLUT 2 primer
```

```
<400> SEQUENCE: 28
gatcagtgct ccagttggtg g                                          21

<210> SEQ ID NO 29
<211> LENGTH: 21
<212> TYPE: DNA
<213> ORGANISM: Artificial
<220> FEATURE:
<223> OTHER INFORMATION: Synthetic GLUT 2 primer

<400> SEQUENCE: 29
tgatgctgca tgtggctcag c                                          21

<210> SEQ ID NO 30
<211> LENGTH: 21
<212> TYPE: DNA
<213> ORGANISM: Artificial
<220> FEATURE:
<223> OTHER INFORMATION: Synthetic GLUT 2 primer

<400> SEQUENCE: 30
tgatcagtgc tccagttggt g                                          21

<210> SEQ ID NO 31
<211> LENGTH: 21
<212> TYPE: DNA
<213> ORGANISM: Artificial
<220> FEATURE:
<223> OTHER INFORMATION: Synthetic GLUT 2 primer

<400> SEQUENCE: 31
tgtctggtgt gcgagccatc c                                          21

<210> SEQ ID NO 32
<211> LENGTH: 21
<212> TYPE: DNA
<213> ORGANISM: Artificial
<220> FEATURE:
<223> OTHER INFORMATION: Synthetic GLUT 2 primer

<400> SEQUENCE: 32
acagcagctt ttggcctgtg g                                          21

<210> SEQ ID NO 33
<211> LENGTH: 21
<212> TYPE: DNA
<213> ORGANISM: Artificial
<220> FEATURE:
<223> OTHER INFORMATION: Synthetic GLUT 3 primer

<400> SEQUENCE: 33
agtggccggc tgctccaact g                                          21

<210> SEQ ID NO 34
<211> LENGTH: 21
<212> TYPE: DNA
<213> ORGANISM: Artificial
<220> FEATURE:
<223> OTHER INFORMATION: Synthetic GLUT 3 primer

<400> SEQUENCE: 34
agacggagtc tcgccctgtg g                                          21

<210> SEQ ID NO 35
<211> LENGTH: 21
```

<212> TYPE: DNA
<213> ORGANISM: Artificial
<220> FEATURE:
<223> OTHER INFORMATION: Synthetic GLUT 3 primer

<400> SEQUENCE: 35
agtccctgag acccgtggca g                                              21

<210> SEQ ID NO 36
<211> LENGTH: 21
<212> TYPE: DNA
<213> ORGANISM: Artificial
<220> FEATURE:
<223> OTHER INFORMATION: Synthetic GLUT 3 primer

<400> SEQUENCE: 36
acaaacctgc acattcggca c                                              21

<210> SEQ ID NO 37
<211> LENGTH: 21
<212> TYPE: DNA
<213> ORGANISM: Artificial
<220> FEATURE:
<223> OTHER INFORMATION: Synthetic GLUT 4 primer

<400> SEQUENCE: 37
tgggcctcac agtgctacct g                                              21

<210> SEQ ID NO 38
<211> LENGTH: 21
<212> TYPE: DNA
<213> ORGANISM: Artificial
<220> FEATURE:
<223> OTHER INFORMATION: Synthetic GLUT 4 primer

<400> SEQUENCE: 38
aagttgctcg tccagttgga g                                              21

<210> SEQ ID NO 39
<211> LENGTH: 21
<212> TYPE: DNA
<213> ORGANISM: Artificial
<220> FEATURE:
<223> OTHER INFORMATION: Synthetic GLUT 4 primer

<400> SEQUENCE: 39
tggagtccct cctgggcact g                                              21

<210> SEQ ID NO 40
<211> LENGTH: 21
<212> TYPE: DNA
<213> ORGANISM: Artificial
<220> FEATURE:
<223> OTHER INFORMATION: Synthetic GLUT 4 primer

<400> SEQUENCE: 40
tggctgaaga gctcggccac g                                              21

<210> SEQ ID NO 41
<211> LENGTH: 21
<212> TYPE: DNA
<213> ORGANISM: Artificial
<220> FEATURE:
<223> OTHER INFORMATION: Synthetic GLUT 4 primer

<400> SEQUENCE: 41

```
tggagtccct cctgggcact g                                              21

<210> SEQ ID NO 42
<211> LENGTH: 21
<212> TYPE: DNA
<213> ORGANISM: Artificial
<220> FEATURE:
<223> OTHER INFORMATION: Synthetic GLUT 4 primer

<400> SEQUENCE: 42
aagttgctcg tccagttgga g                                              21

<210> SEQ ID NO 43
<211> LENGTH: 21
<212> TYPE: DNA
<213> ORGANISM: Artificial
<220> FEATURE:
<223> OTHER INFORMATION: Synthetic GLUT 5 primer

<400> SEQUENCE: 43
tgccctggca accctgatag c                                              21

<210> SEQ ID NO 44
<211> LENGTH: 21
<212> TYPE: DNA
<213> ORGANISM: Artificial
<220> FEATURE:
<223> OTHER INFORMATION: Synthetic GLUT 5 primer

<400> SEQUENCE: 44
tatggcatcc aggacactgt g                                              21

<210> SEQ ID NO 45
<211> LENGTH: 21
<212> TYPE: DNA
<213> ORGANISM: Artificial
<220> FEATURE:
<223> OTHER INFORMATION: Synthetic GLUT 5 primer

<400> SEQUENCE: 45
gatggctggc cgatcctgct g                                              21

<210> SEQ ID NO 46
<211> LENGTH: 21
<212> TYPE: DNA
<213> ORGANISM: Artificial
<220> FEATURE:
<223> OTHER INFORMATION: Synthetic GLUT 5 primer

<400> SEQUENCE: 46
agccacgtta ccaggagcca c                                              21

<210> SEQ ID NO 47
<211> LENGTH: 21
<212> TYPE: DNA
<213> ORGANISM: Artificial
<220> FEATURE:
<223> OTHER INFORMATION: Synthetic GLUT 5 primer

<400> SEQUENCE: 47
gggtacaacg tggctgctgt c                                              21

<210> SEQ ID NO 48
<211> LENGTH: 21
<212> TYPE: DNA
<213> ORGANISM: Artificial
```

-continued

```
<220> FEATURE:
<223> OTHER INFORMATION: Synthetic GLUT 5 primer

<400> SEQUENCE: 48
tatggcatcc aggacactgt g                                              21

<210> SEQ ID NO 49
<211> LENGTH: 21
<212> TYPE: DNA
<213> ORGANISM: Artificial
<220> FEATURE:
<223> OTHER INFORMATION: Synthetic GLUT 6 primer

<400> SEQUENCE: 49
acagctgcct gcatcccggt g                                              21

<210> SEQ ID NO 50
<211> LENGTH: 21
<212> TYPE: DNA
<213> ORGANISM: Artificial
<220> FEATURE:
<223> OTHER INFORMATION: Synthetic GLUT 6 primer

<400> SEQUENCE: 50
tgaacaccag gctcaccaag c                                              21

<210> SEQ ID NO 51
<211> LENGTH: 21
<212> TYPE: DNA
<213> ORGANISM: Artificial
<220> FEATURE:
<223> OTHER INFORMATION: Synthetic GLUT 6 primer

<400> SEQUENCE: 51
tcgatgtcca ctgggagttc g                                              21

<210> SEQ ID NO 52
<211> LENGTH: 21
<212> TYPE: DNA
<213> ORGANISM: Artificial
<220> FEATURE:
<223> OTHER INFORMATION: Synthetic GLUT 6 primer

<400> SEQUENCE: 52
agcagtgcta cctgtcccga g                                              21

<210> SEQ ID NO 53
<211> LENGTH: 21
<212> TYPE: DNA
<213> ORGANISM: Artificial
<220> FEATURE:
<223> OTHER INFORMATION: Synthetic GLUT 6 primer

<400> SEQUENCE: 53
accaaatccc aggcatcctg g                                              21

<210> SEQ ID NO 54
<211> LENGTH: 21
<212> TYPE: DNA
<213> ORGANISM: Artificial
<220> FEATURE:
<223> OTHER INFORMATION: Synthetic GLUT 6 primer

<400> SEQUENCE: 54
tggctggaca gcagtgctac c                                              21
```

<210> SEQ ID NO 55
<211> LENGTH: 21
<212> TYPE: DNA
<213> ORGANISM: Artificial
<220> FEATURE:
<223> OTHER INFORMATION: Synthetic GLUT 8 primer

<400> SEQUENCE: 55
tccaggtgct gttcacagct g                                              21

<210> SEQ ID NO 56
<211> LENGTH: 21
<212> TYPE: DNA
<213> ORGANISM: Artificial
<220> FEATURE:
<223> OTHER INFORMATION: Synthetic GLUT 8 primer

<400> SEQUENCE: 56
accgcaggtc tgcaaagctc g                                              21

<210> SEQ ID NO 57
<211> LENGTH: 21
<212> TYPE: DNA
<213> ORGANISM: Artificial
<220> FEATURE:
<223> OTHER INFORMATION: Synthetic GLUT 8 primer

<400> SEQUENCE: 57
tcgtgggtgt catccaggtg c                                              21

<210> SEQ ID NO 58
<211> LENGTH: 21
<212> TYPE: DNA
<213> ORGANISM: Artificial
<220> FEATURE:
<223> OTHER INFORMATION: Synthetic GLUT 8 primer

<400> SEQUENCE: 58
agcttggagt cacaggcttg c                                              21

<210> SEQ ID NO 59
<211> LENGTH: 21
<212> TYPE: DNA
<213> ORGANISM: Artificial
<220> FEATURE:
<223> OTHER INFORMATION: Synthetic GLUT 8 primer

<400> SEQUENCE: 59
tccaggtgct gttcacagct g                                              21

<210> SEQ ID NO 60
<211> LENGTH: 21
<212> TYPE: DNA
<213> ORGANISM: Artificial
<220> FEATURE:
<223> OTHER INFORMATION: Synthetic GLUT 8 primer

<400> SEQUENCE: 60
tccatagggc ctgaggacct c                                              21

<210> SEQ ID NO 61
<211> LENGTH: 21
<212> TYPE: DNA
<213> ORGANISM: Artificial
<220> FEATURE:
<223> OTHER INFORMATION: Synthetic GLUT 9 primer -continued

<400> SEQUENCE: 61
tggctctagg gctggcacca g    21

<210> SEQ ID NO 62
<211> LENGTH: 21
<212> TYPE: DNA
<213> ORGANISM: Artificial
<220> FEATURE:
<223> OTHER INFORMATION: Synthetic GLUT 9 primer

<400> SEQUENCE: 62
agccacggat ctccttgggt g    21

<210> SEQ ID NO 63
<211> LENGTH: 21
<212> TYPE: DNA
<213> ORGANISM: Artificial
<220> FEATURE:
<223> OTHER INFORMATION: Synthetic GLUT 9 primer

<400> SEQUENCE: 63
tcgccatcgg tggacttgtg g    21

<210> SEQ ID NO 64
<211> LENGTH: 21
<212> TYPE: DNA
<213> ORGANISM: Artificial
<220> FEATURE:
<223> OTHER INFORMATION: Synthetic GLUT 9 primer

<400> SEQUENCE: 64
tcacggtgac cacctgccag c    21

<210> SEQ ID NO 65
<211> LENGTH: 21
<212> TYPE: DNA
<213> ORGANISM: Artificial
<220> FEATURE:
<223> OTHER INFORMATION: Synthetic GLUT 10 primer

<400> SEQUENCE: 65
actcaggccc aagctgtctg g    21

<210> SEQ ID NO 66
<211> LENGTH: 21
<212> TYPE: DNA
<213> ORGANISM: Artificial
<220> FEATURE:
<223> OTHER INFORMATION: Synthetic GLUT 10 primer

<400> SEQUENCE: 66
tggttgcatg cgcctgtagt c    21

<210> SEQ ID NO 67
<211> LENGTH: 21
<212> TYPE: DNA
<213> ORGANISM: Artificial
<220> FEATURE:
<223> OTHER INFORMATION: Synthetic GLUT 10 primer

<400> SEQUENCE: 67
acggttcacc ctgagctttg g    21

<210> SEQ ID NO 68

```
<211> LENGTH: 21
<212> TYPE: DNA
<213> ORGANISM: Artificial
<220> FEATURE:
<223> OTHER INFORMATION: Synthetic GLUT 10 primer

<400> SEQUENCE: 68
tggcaaagcc agctccagca c                                              21

<210> SEQ ID NO 69
<211> LENGTH: 21
<212> TYPE: DNA
<213> ORGANISM: Artificial
<220> FEATURE:
<223> OTHER INFORMATION: Synthetic GLUT 11 primer

<400> SEQUENCE: 69
tctttacggc tctggggatc g                                              21

<210> SEQ ID NO 70
<211> LENGTH: 21
<212> TYPE: DNA
<213> ORGANISM: Artificial
<220> FEATURE:
<223> OTHER INFORMATION: Synthetic GLUT 11 primer

<400> SEQUENCE: 70
agcaggtcat caggctgtac c                                              21

<210> SEQ ID NO 71
<211> LENGTH: 21
<212> TYPE: DNA
<213> ORGANISM: Artificial
<220> FEATURE:
<223> OTHER INFORMATION: Synthetic GLUT 11 primer

<400> SEQUENCE: 71
tccttacggc ctcggacgca g                                              21

<210> SEQ ID NO 72
<211> LENGTH: 21
<212> TYPE: DNA
<213> ORGANISM: Artificial
<220> FEATURE:
<223> OTHER INFORMATION: Synthetic GLUT 11 primer

<400> SEQUENCE: 72
agtcccgatg atcgcgtact g                                              21

<210> SEQ ID NO 73
<211> LENGTH: 21
<212> TYPE: DNA
<213> ORGANISM: Artificial
<220> FEATURE:
<223> OTHER INFORMATION: Synthetic GLUT 11 primer

<400> SEQUENCE: 73
agctcctagg tggccctcag g                                              21

<210> SEQ ID NO 74
<211> LENGTH: 21
<212> TYPE: DNA
<213> ORGANISM: Artificial
<220> FEATURE:
<223> OTHER INFORMATION: Synthetic GLUT 11 primer

<400> SEQUENCE: 74
```
acagctctgt ggccaggatc c                                           21

<210> SEQ ID NO 75
<211> LENGTH: 21
<212> TYPE: DNA
<213> ORGANISM: Artificial
<220> FEATURE:
<223> OTHER INFORMATION: Synthetic GLUT 11 primer

<400> SEQUENCE: 75
tggagcactg cttgcaggtc c                                           21

<210> SEQ ID NO 76
<211> LENGTH: 21
<212> TYPE: DNA
<213> ORGANISM: Artificial
<220> FEATURE:
<223> OTHER INFORMATION: Synthetic GLUT 11 primer

<400> SEQUENCE: 76
tccatggcac tgcccagaac c                                           21

<210> SEQ ID NO 77
<211> LENGTH: 21
<212> TYPE: DNA
<213> ORGANISM: Artificial
<220> FEATURE:
<223> OTHER INFORMATION: Synthetic GLUT 12 primer

<400> SEQUENCE: 77
acgcattgcc ataggggtct c                                           21

<210> SEQ ID NO 78
<211> LENGTH: 21
<212> TYPE: DNA
<213> ORGANISM: Artificial
<220> FEATURE:
<223> OTHER INFORMATION: Synthetic GLUT 12 primer

<400> SEQUENCE: 78
tctcgctgag caccagccag g                                           21

<210> SEQ ID NO 79
<211> LENGTH: 21
<212> TYPE: DNA
<213> ORGANISM: Artificial
<220> FEATURE:
<223> OTHER INFORMATION: Synthetic GLUT 12 primer

<400> SEQUENCE: 79
tccactgggg ttggagtcgt c                                           21

<210> SEQ ID NO 80
<211> LENGTH: 21
<212> TYPE: DNA
<213> ORGANISM: Artificial
<220> FEATURE:
<223> OTHER INFORMATION: Synthetic GLUT 12 primer

<400> SEQUENCE: 80
tgggcagttg tccacactgt g                                           21

<210> SEQ ID NO 81
<211> LENGTH: 21
<212> TYPE: DNA

```
<213> ORGANISM: Artificial
<220> FEATURE:
<223> OTHER INFORMATION: Synthetic GLUT 12 primer

<400> SEQUENCE: 81
tccactgggg ttggagtcgt c                                              21

<210> SEQ ID NO 82
<211> LENGTH: 21
<212> TYPE: DNA
<213> ORGANISM: Artificial
<220> FEATURE:
<223> OTHER INFORMATION: Synthetic GLUT 12 primer

<400> SEQUENCE: 82
tctcgctgag caccagccag g                                              21

<210> SEQ ID NO 83
<211> LENGTH: 21
<212> TYPE: DNA
<213> ORGANISM: Artificial
<220> FEATURE:
<223> OTHER INFORMATION: Synthetic SGLT1 primer

<400> SEQUENCE: 83
aggttggctg taccaacatc g                                              21

<210> SEQ ID NO 84
<211> LENGTH: 21
<212> TYPE: DNA
<213> ORGANISM: Artificial
<220> FEATURE:
<223> OTHER INFORMATION: Synthetic SGLT1 primer

<400> SEQUENCE: 84
agttgctggg ctccatgcag c                                              21

<210> SEQ ID NO 85
<211> LENGTH: 21
<212> TYPE: DNA
<213> ORGANISM: Artificial
<220> FEATURE:
<223> OTHER INFORMATION: Synthetic SGLT1 primer

<400> SEQUENCE: 85
tggtggccga ttggagcctc c                                              21

<210> SEQ ID NO 86
<211> LENGTH: 21
<212> TYPE: DNA
<213> ORGANISM: Artificial
<220> FEATURE:
<223> OTHER INFORMATION: Synthetic SGLT1 primer

<400> SEQUENCE: 86
tgctgactgc acaatgggca c                                              21

<210> SEQ ID NO 87
<211> LENGTH: 21
<212> TYPE: DNA
<213> ORGANISM: Artificial
<220> FEATURE:
<223> OTHER INFORMATION: Synthetic SGLT1 primer

<400> SEQUENCE: 87
tggagctcat gcccaatgga c                                              21
```

<210> SEQ ID NO 88
<211> LENGTH: 21
<212> TYPE: DNA
<213> ORGANISM: Artificial
<220> FEATURE:
<223> OTHER INFORMATION: Synthetic SGLT1 primer

<400> SEQUENCE: 88
tcccttcaac accacaggac g                                              21

<210> SEQ ID NO 89
<211> LENGTH: 21
<212> TYPE: DNA
<213> ORGANISM: Artificial
<220> FEATURE:
<223> OTHER INFORMATION: Synthetic SGLT2 primer

<400> SEQUENCE: 89
tgggcggcta cttcctggca g                                              21

<210> SEQ ID NO 90
<211> LENGTH: 21
<212> TYPE: DNA
<213> ORGANISM: Artificial
<220> FEATURE:
<223> OTHER INFORMATION: Synthetic SGLT2 primer

<400> SEQUENCE: 90
acacgcgcct gcacacctca g                                              21

<210> SEQ ID NO 91
<211> LENGTH: 21
<212> TYPE: DNA
<213> ORGANISM: Artificial
<220> FEATURE:
<223> OTHER INFORMATION: Synthetic SGLT2 primer

<400> SEQUENCE: 91
tgccacagta cctgcgcaag c                                              21

<210> SEQ ID NO 92
<211> LENGTH: 21
<212> TYPE: DNA
<213> ORGANISM: Artificial
<220> FEATURE:
<223> OTHER INFORMATION: Synthetic SGLT2 primer

<400> SEQUENCE: 92
accgttgggc atgagcttca c                                              21

<210> SEQ ID NO 93
<211> LENGTH: 21
<212> TYPE: DNA
<213> ORGANISM: Artificial
<220> FEATURE:
<223> OTHER INFORMATION: Synthetic SGLT2 primer

<400> SEQUENCE: 93
tgcagcgacc aggtcatcgt g                                              21

<210> SEQ ID NO 94
<211> LENGTH: 21
<212> TYPE: DNA
<213> ORGANISM: Artificial
<220> FEATURE:

<223> OTHER INFORMATION: Synthetic SGLT2 primer

<400> SEQUENCE: 94
agccaggcca ccgacactac c    21

<210> SEQ ID NO 95
<211> LENGTH: 21
<212> TYPE: DNA
<213> ORGANISM: Artificial
<220> FEATURE:
<223> OTHER INFORMATION: Synthetic SGLT5 primer

<400> SEQUENCE: 95
tcgcagcttt tgaccagatc g    21

<210> SEQ ID NO 96
<211> LENGTH: 21
<212> TYPE: DNA
<213> ORGANISM: Artificial
<220> FEATURE:
<223> OTHER INFORMATION: Synthetic SGLT5 primer

<400> SEQUENCE: 96
tgctcgttgg cacgtcgcca g    21

<210> SEQ ID NO 97
<211> LENGTH: 21
<212> TYPE: DNA
<213> ORGANISM: Artificial
<220> FEATURE:
<223> OTHER INFORMATION: Synthetic SGLT5 primer

<400> SEQUENCE: 97
tgcaccgacc aggtcatcgt g    21

<210> SEQ ID NO 98
<211> LENGTH: 21
<212> TYPE: DNA
<213> ORGANISM: Artificial
<220> FEATURE:
<223> OTHER INFORMATION: Synthetic SGLT5 primer

<400> SEQUENCE: 98
actcacgccg atgagtgcca c    21

<210> SEQ ID NO 99
<211> LENGTH: 21
<212> TYPE: DNA
<213> ORGANISM: Artificial
<220> FEATURE:
<223> OTHER INFORMATION: Synthetic SGLT5 primer

<400> SEQUENCE: 99
tgccacgtac agacgccatg c    21

<210> SEQ ID NO 100
<211> LENGTH: 21
<212> TYPE: DNA
<213> ORGANISM: Artificial
<220> FEATURE:
<223> OTHER INFORMATION: Synthetic SGLT5 primer

<400> SEQUENCE: 100
agttgcccgc tgttggagtc c    21